United States Patent
Huck et al.

(10) Patent No.: US 9,586,938 B2
(45) Date of Patent: *Mar. 7, 2017

(54) CYCLIC AMINE AZAHETEROCYCLIC CARBOXAMIDES

(75) Inventors: Bayard R. Huck, Sudbury, MA (US); Xiaoling Chen, Chestnut Hill, MA (US); Constantin Neagu, Belmont, MA (US); Reinaldo Jones, Lowell, MA (US); Yufang Xiao, Lexington, MA (US); Igor Mochalkin, San Diego, CA (US)

(73) Assignee: Merck Patent GmbH, Darmstadt (DE)

( * ) Notice: Subject to any disclaimer, the term of this patent is extended or adjusted under 35 U.S.C. 154(b) by 252 days.

This patent is subject to a terminal disclaimer.

(21) Appl. No.: 13/810,860

(22) PCT Filed: Jul. 28, 2011

(86) PCT No.: PCT/US2011/045658
§ 371 (c)(1),
(2), (4) Date: Mar. 19, 2013

(87) PCT Pub. No.: WO2012/016001
PCT Pub. Date: Feb. 2, 2012

(65) Prior Publication Data
US 2013/0217709 A1   Aug. 22, 2013

Related U.S. Application Data

(60) Provisional application No. 61/368,972, filed on Jul. 29, 2010.

(51) Int. Cl.
| | |
|---|---|
| *A01N 43/54* | (2006.01) |
| *C07D 239/42* | (2006.01) |
| *C07D 401/04* | (2006.01) |
| *A01N 43/42* | (2006.01) |
| *A61K 31/47* | (2006.01) |
| *C07D 403/12* | (2006.01) |
| *C07D 233/90* | (2006.01) |
| *C07D 401/12* | (2006.01) |
| *C07D 401/14* | (2006.01) |
| *C07D 403/10* | (2006.01) |
| *C07D 405/12* | (2006.01) |
| *C07D 405/14* | (2006.01) |
| *A61K 31/4709* | (2006.01) |
| *A61K 31/517* | (2006.01) |
| *A61K 45/06* | (2006.01) |
| *C07D 403/14* | (2006.01) |

(52) U.S. Cl.
CPC ........ *C07D 403/12* (2013.01); *A61K 31/4709* (2013.01); *A61K 31/517* (2013.01); *A61K 45/06* (2013.01); *C07D 233/90* (2013.01); *C07D 401/04* (2013.01); *C07D 401/12* (2013.01); *C07D 401/14* (2013.01); *C07D 403/10* (2013.01); *C07D 403/14* (2013.01); *C07D 405/12* (2013.01); *C07D 405/14* (2013.01)

(58) Field of Classification Search
CPC .. A61K 31/4709; A61K 31/517; A61K 45/06; C07D 233/90; C07D 401/04; C07D 401/12; C07D 401/14; C07D 403/10; C07D 403/12; C07D 403/14; C07D 405/12; C07D 405/14; A47J 27/56
USPC .......... 514/256, 313; 544/284, 293; 546/162
See application file for complete search history.

(56) References Cited

U.S. PATENT DOCUMENTS

2006/0009460 A1   1/2006   Dickson et al.

FOREIGN PATENT DOCUMENTS

| EP | 0339768 A1 | 11/1989 |
|---|---|---|
| WO | 99/09024 A1 | 2/1999 |
| WO | 03/064397 A1 | 8/2003 |
| WO | 2004/014861 A1 | 2/2004 |
| WO | 2004/092154 A1 | 10/2004 |
| WO | 2005/033086 A1 | 4/2005 |
| WO | 2005/039506 A2 | 5/2005 |
| WO | 2005/054237 A1 | 6/2005 |
| WO | 2005/056014 A1 | 6/2005 |
| WO | 2005/117909 A2 | 12/2005 |
| WO | 2005/120509 A1 | 12/2005 |
| WO | 2006/071819 A1 | 7/2006 |
| WO | 2006/120573 A2 | 11/2006 |
| WO | 2006/131835 A2 | 12/2006 |
| WO | 2006/136821 A1 | 12/2006 |
| WO | 2008049047 A2 | 4/2008 |
| WO | 2008/140947 A1 | 11/2008 |
| WO | 2010051549 A1 | 5/2010 |
| WO | 2010093419 A1 | 8/2010 |
| WO | 2012/013282 A1 | 2/2012 |

OTHER PUBLICATIONS

Wolff, Some consideration for prodrug design, Burgers Medicinal Chemistry and Drug Discovery, 5th Edition, vol. I Principles and Practice, pp. 975-977, 1995.*
Banker et al., Prodrugs, Modern Pharmaceutics, Third Edition and Expanded, pp. 451 and 596 (1996).*
Bärlund, Maarit, et al., Multiple Genes at 17q23 Undergo Amplification and Overexpression in Breast Cancer, Cancer Research, 2000, pp. 5340-5344, vol. 60.
Couch, Fergus J., et al., Localization of PS6K to Chromosomal Region 17q23 and Determination of Its Amplification in Breast Cancer, Cancer Research, 1999, pp. 1408-1411, vol. 59.

(Continued)

*Primary Examiner* — Uma Ramachandran
(74) *Attorney, Agent, or Firm* — Dwight D. Kim; EMD Serono Research and Development Institute

(57) ABSTRACT

The invention provides novel cyclic amine azaheterocyclic carboxamide according to Formula (I), Formula (II) and Formula (III) their manufacture and use for the treatment of hyperproliferative diseases, such as cancer.

5 Claims, No Drawings

(56) References Cited

OTHER PUBLICATIONS

Garcia-Bustos, Jose F., PIK 1, an essential phosphatidylinositol 4-kinase associated with the yeast nucleus, The EMBO Journal, 1994, pp. 2352-2361, vol. 13.
Hanks, Steven K., et al., The eukaryotic protein kinase superfamily: kinase (catalytic) domain structure and classification, The FASEB Journal, 1995, pp. 576-596, vol. 9.
Hardie, G., et al., The Protein Kinase Facts Book I and II, 1995, Academic Press, San Diego, CA.
Hiles, Ian D. et al., Phosphatidylinositol 3-Kinase: Structure and Expression of the 110 kd Catalytic Subunit, Cell, 1992, 419-429, vol. 70.
Knighton, Daniel R., et al. Crystal Structure of the Catalytic Subunit of Cyclic Adenosine Monophosphate-Dependent Protein Kinase, 1991, pp. 407-414, vol. 253.
Kunz, Jeannette et al., Target of Rapamycin in Yeast, TOR2, Is an Essential Phosphatidylinositol Kinase Homolog Required for G1 Progression, Cell, 1993, pp. 585-596, vol. 73.
Wu, Guo-Jun, et al., 17q23 Amplifications in Breast Cancer Involve the PAT1, RAD51C, PS6K, and SIGMA1B Genes, Cancer Research, 2000, pp. 5371-5375, vol. 60.

* cited by examiner

CYCLIC AMINE AZAHETEROCYCLIC CARBOXAMIDES

FIELD OF THE INVENTION

The invention relates to a series of cyclic amine azaheterocyclic carboxamide compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

SUMMARY OF THE RELATED ART

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Protein kinase 70S6K, the 70 kDa ribosomal protein kinase p70S6K (also known as SK6, p70/p85 S6 kinase, p70/p85 ribosomal S6 kinase and pp70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKCζ. Akt directly phosphorylates and inactivates TSC2, thereby activating mTOR. In addition, studies with mutant alleles of p70S6K that inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidine tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on it participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M. Barlund, O. Monni, J. Kononen, R. Cornelison, J. Torhorst, G. Sauter, O.-P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375).

The p70S6K gene has been identified as a target of amplification and overexpression in this region, and statistically significant association between amplification and poor prognosis has been observed.

Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported.

In response to energy stress, the tumor suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations.

p70S6K has been implicated in metabolic diseases and disorders. It was reported that the absence of p70S6K protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

Compounds described as suitable for p70S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/131835, WO 08/140947 and PCT/US10/000313.

DESCRIPTION OF THE INVENTION

It is the object of the present invention to provide novel p70S6K inhibitors useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

As a result, this invention provides novel, cyclic amine azaheterocylic carboxamide compounds and pharmaceutically acceptable salts, solvates or prodrugs thereof, that are kinase inhibitors and useful in the treatment of the above mentioned diseases.

The compounds are defined by Formula (I):

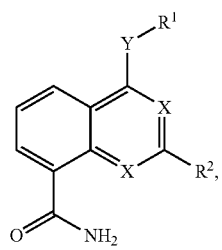

(I)

and pharmaceutically acceptable salts, solvates, solvates of salts, or prodrugs thereof,
wherein:
X is N or C—$R^3$,
Y is N, NH or is absent,
$R^1$ is $L^1$-$R^4$-$L^2$-$R^5$-$L^3$-$R^6$, $L^1$-$R^4$-$L^2$-$R^5$ or $L^1$-$R^4$,
$R^2$ is A, Hal, OH, OA, SH, CN, $NH_2$, $NO_2$, NHA, NH-$L^1$-Ar, NHCOA, NHCO-$L^1$-Ar, $NHSO_2A$, $NHSO_2$-$L^1$-Ar, NHCONHA, NHCONH-$L^1$-Ar, $L^1$-Ar, O-$L^1$-Ar, $L^1$-$R^4$ or H,
$L^1$, $L^3$ each, independently of one another is a single bond, methylene, or methyl substituted methylene, wherein the methylene, or the methyl group of the methyl substituted methylene may be unsubstituted or mono- or disubstituted with Hal, OH, CN, $NH_2$, NH(LA), $N(LA)_2$, $NO_2$, COOH, $N_3$, ethenyl or ethynyl, and/or monosubstituted with $R^4$, and in which one or two $CH_2$ groups may be replaced by an O or S atom or by an —NH—, —N(LA)-, —CONH—, —N(LA)COO—, —$SO_2$— or —NHCO— group,
$R^3$ is H, A, Hal, OH, COOH, SH, $NH_2$, $NO_2$ or CN,
$R^4$, $R^5$, $R^6$ each, independently of one another, are Ar, or cyclic A which may be mono- or disubstituted by Hal or LA,
$L^2$ is —NHCO—, —NHCOO—, —NHCONH—, —NHCONA-, —NHCOA-, —O—, —S—, —NH—, —$NHSO_2$—, —$SO_2NH$—, —CONH—, —CONHCONH—, —NHCONHCO—, or -A-, Ar is a mono- or bicyclic aromatic homo- or heterocycle having 0, 1, 2, 3 or 4 N, O and/or S atoms and 5, 6, 7, 8, 9, or 10 skeleton atoms, which may be unsubstituted or, independently of one another, mono-, di- or trisubstituted by Hal, A, OH, SH, OA, $NH_2$, NHA, $NA_2$, $NO_2$, CN, OCN, SCN, COOH, COOA, $CONH_2$, CONHA, $CONA_2$, NHCOA, NHCONHA, $NHCONH_2$, $NHSO_2A$, CHO, COA, $SO_2NH_2$, $SO_2A$ and/or $SO_2Hal$, and in which a ring N-atom may be substituted by an O-atom to form an N-oxide group,
and in which in the case of a bicyclic aromatic cycle on of the two rings may be partly saturated,
A is unbranched or branched linear or cyclic alkyl having 1, 2, 3, 4, 5, 6, 7 or 8 C atoms, in which one or two $CH_2$ groups may be replaced by an O or S atom and/or by an —NH—, —CO—, —NHCOO—, —NHCONH—. —N(LA)-, —CONH—, —NHCO— or —CH=CH— group, and in which 1-3 H atoms may be replaced by Hal, and in which one or two $CH_3$ groups may be replaced by OH, SH, $NH_2$, NH(LA), $N(LA)_2$, NHCOOH, $NHCONH_2$ or CN,
LA is unbranched or branched, linear alkyl having 1, 2, 3 or 4 C atoms, wherein 1, 2 or 3 H atoms may be replaced by Hal and
Hal is F, Cl, Br or I.

In general, all residues which occur more than once may be identical or different, i.e. are independent of one another. Above and below, the residues and parameters have the meanings indicated for the Formula (I), unless expressly indicated otherwise.

Accordingly, the invention relates, in particular, to the compounds of the Formula (I) in which at least one of the said residues has one of the preferred meanings indicated below.

"Hal" denotes fluorine, chlorine, bromine or iodine, in particular fluorine or chlorine.

"A" denotes, for example, methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. "A" further denotes alkyl as defined above, in which one or two $CH_2$ groups may be replaced by O or S atoms and/or by NH, N(LA), CONH, NHCO or —CH=CH— groups and/or in addition 1-3 H atoms may be replaced by F and/or Cl, such as, for example, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy.

In other examples of "A", one or two $CH_3$ groups is replaced by OH, SH, $NH_2$, N(LA)H, $N(LA)_2$ or CN, such as, for example, N,N'-dimethylaminoalkyl, 2-aminoethyl, 3-aminopropyl, 4-aminobutyl, 5-aminopentyl, 3-aminomethylcyclobutyl or cyanoalkyl. Cyclic A preferably denotes cyclopropyl, cyclobutyl, cyclopentyl, cyclohexyl or cycloheptyl.

"LA" denotes unbranched or branched, linear alkyl having 1, 2, 3 or 4 C atoms, wherein 1, 2 or 3 H atoms may be replaced by Hal, e.g. methyl, ethyl, trifluoromethyl, difluoromethyl, 1,1,1-trifluoroethyl, propyl, isopropyl, butyl, isobutyl, sec-butyl or tert-butyl.

"Ar" denotes, for example, unsubstituted phenyl, naphthyl or biphenyl, furthermore preferably, for example, phenyl, naphthyl or biphenyl, each of which is mono-, di- or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

"Ar" furthermore denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)-phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl, (4-methoxyphenyl)methyl, (3-methoxyphenyl)methyl, (4-methoxyphenyl)ethyl, (3-methoxyphenyl)ethyl. "Ar" furthermore preferably denotes 2-, 3- or 4-phenyl, 2-, 3- or 4-phenylmethyl, 2-, 3- or 4-phenylethyl, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 3- or 4-pyridylmethyl, 2-, 3- or 4-pyridylethyl, 2-, 4-, 5- or 6-pyrimidinyl, 2-, 3-, 5-, or 6-pyrazin-1- or 4-yl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-oxadiazol-2-yl, 1,3,4-thiadiazol-2- or -5-yl, 1,2,4-thiadiazol-3- or -5-yl, 1,2,3-thiadiazol-4- or -5-yl, 3- or 4-pyridazinyl, 1-, 2-, 3-, 4-, 5-, 6- or 7-indolyl, 2-, 3-, 4- or 5-isoindolyl, 2-, 6, - or 8-purinyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, quinoxalin-2-, 3-, 4- or 5-yl, 4-, 5-, or 6-phthalazinyl, 2-, 3-, 5-, 6-, 7- or 8-2H-benzo-1,4-oxazinyl, further preferably 1,3-benzodioxol-2-, 4- or 5-yl, thiophen-2- or 3-yl, 1,4-benzodioxan-6-yl, 2,1,3-benzothiadiazol-4- or -5-yl or 2,1,3-benzoxadiazol-5-yl, furan-2- or 3-yl, 2,3-dihydro-benzofuran-2-, 3-, 4- or 5-yl, each of which is unsubstituted or may be mono-, di- or trisubstituted, for example, by carbonyl oxygen, F, Cl, Br, methyl, ethyl, propyl, phenyl, benzyl, —CH$_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methylsulfonyl.

In those cases where $R^1$ is $L^1$-$R^4$-$L^2$-$R^5$, residue $R^4$ obviously has a bridging function, and is substituted by linkers $L^1$ and $L^2$, independently of any further substitutions it may have.

The term "substituted" preferably relates to the substitution by the above-mentioned substituents, where a plurality of different degrees of substitution are possible, unless indicated otherwise.

All physiologically acceptable salts, derivatives, solvates, solvates of salts, and stereoisomers of these compounds, including mixtures thereof in all ratios, are also in accordance with the invention.

The compounds of the Formula (I) may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

In a preferred group of compounds of Formula (I) the variables and substituents have the following meanings:

X is N,
Y is NH,
$R^1$ is $L^1$-$R^4$-$L^2$-$R^5$,
$R^2$ is LA, Hal, OH, O(LA), SH, CN, NH$_2$, NO$_2$, NH(LA), NHCO(LA), NHSO$_2$(LA), NHCONH(LA),
$L^1$, $L^3$ is methyl substituted methylene, wherein the methyl group of the methyl substituted methylene is monosubstituted with NH$_2$ or NH(LA), N(LA)$_2$, or cyclic A which may be mono- or disubstituted by Hal or LA,
$R^4$, $R^5$ is a monocyclic aromatic homo- or heterocycle having 0, 1 or 2 N, O and/or S atoms and 5 or 6 skeleton atoms, which may be unsubstituted or, independently of one another, mono-, di- or trisubstituted by Hal, A, OH, SH, OA, NH$_2$, NHA, NA$_2$, NO$_2$, CN, OCN, SCN, COOH, COOA, CONH$_2$, CONHA, CONA$_2$, NHCOA, NHCONHA, NHCONH₂, NHSO₂A, CHO, COA, SO₂NH₂, SO₂A and/or SO₂Hal, L² is —NHCO—, —NHCOO—, —NHCONH—, —NHCONA-, —NHCOA-, —O—, —S—, —NH—, —NHSO₂—, —SO₂NH—, —CONH—, —CONHCONH—, —NHCONHCO—, or -A-, A is unbranched or branched linear or cyclic alkyl having 1, 2, 3, 4, 5, 6, 7 or 8 C atoms, in which one or two CH₂ groups may be replaced by an O or S atom and/or by an —NH—, —CO—, —NHCOO—, —NHCONH—, —N(LA)-, —CONH—, —NHCO— or —CH=CH— group, and in which 1-3 H atoms may be replaced by Hal, and in which one or two CH₃ groups may be replaced by OH, SH, NH₂, NH(LA), N(LA)₂, NHCOOH, NHCONH₂ or CN, LA is unbranched or branched, linear alkyl having 1, 2, 3 or 4 C atoms, wherein 1, 2 or 3 H atoms may be replaced by Hal and Hal is F, Cl, Br or I.

In preferred embodiments, the compounds of the present invention are described by Formula (II) and Formula (III), and pharmaceutically acceptable salts, solvates, solvates of salts, or prodrugs thereof, in which the residue identifiers which overlap with Formula (I) have the same definitions as in Formula (I), i.e., X and R², while the balance of the residue identifiers, i.e., Y', Z and Z', are defined below:

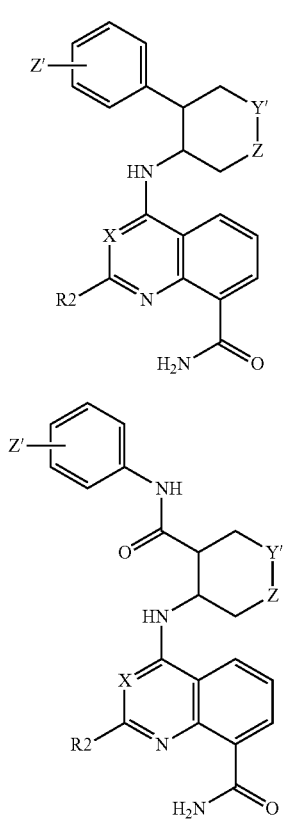

wherein,

Y' is CH2 or NH such that when Y' is NH, Z is CH2 (or absent) and when Y' is CH2, Z is NH, Z is CH2, NH or is absent such that when Z is CH2 (or absent), Y is NH and when Z is NH, Y is CH2 and Z' is Ar, alkyl, halogen, OR, NRR, CF3, CN, OCF3, SR or H (mono, di, or tri-substituted with any above combination).

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

"Solvates" means solvent additions forms that contain either stoichiometric or non stoichiometric amounts of solvent. Many compounds have a tendency to trap a fixed molar ratio of solvent molecules in the crystalline solid state, thus forming a solvate. For example, if the solvent is water the solvate formed is a hydrate, when the solvent is alcohol, the solvate formed is an alcoholate, if the solvent is an ether, the solvate formed is an etherate. Specific examples of solvates include mono- or dihydrates, methanolates, ethanolates or diethyletherates.

Those skilled in the art appreciate that in many cases the solvates of pharmaceutical active ingredients, or their pharmaceutically acceptable salts, are used in pharmaceutical compositions, and know how to obtain such solvates.

Furthermore, the present invention relates to pharmaceutical compositions comprising a compound of the present invention, or a prodrug compound thereof, or a pharmaceutically acceptable salt or solvate, or a solvate of such salt, as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other p70S6K inhibitors.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogenous leukemia, myeloid cell leukemia, glioma, Kaposi's sarcoma, or any other type of solid or liquid tumors. Preferably, the cancer to be treated is chosen from breast, colorectal, lung, prostate or pancreatic cancer or glioblastoma.

The invention also relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or solvate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and sclerodema, diabetes, diabetic retinopathy, retinopathy of prematurity and age-related macular degeneration.

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, such as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils.

Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of:

a) an effective amount of a compound according to the invention or a physiologically acceptable salt, solvate or prodrug thereof, and b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

EXPERIMENTAL SECTION

Some abbreviations that may appear in this application are as follows:

| Abbreviations | |
|---|---|
| Designation | |
| ACN | acetonitrile |
| ATP | Adenosine triphosphate |
| b | Broad peak |
| d | Doublet |
| DMSO | dimethylsulfoxide |
| DIEA | N,N-Diisopropylethylamine |
| DTT | dithiothreitol |
| EDTA | Ethylenediaminetetraacetic acid |
| equiv. | equivalents |
| Et | ethyl |
| h | hour |
| HEPES | 4-(2-hydroxyethyl)-1-piperazineethanesulfonic acid |
| HPLC | High pressure liquid chromatography |
| LC/MS | Liquid chromatography coupled to mass spectrometry |
| m | multiplet |
| M | Molecular ion |
| m/z | Mass-to-charge ratio |
| Me | methyl |
| min | minute |
| MS | Mass spectrometry |
| N | Normal (unit of concentration) |
| NMO | 4-methylmorpholine N-oxide |
| NMR | Nuclear Magnetic Resonance |
| PG | Protecting group |
| psi | Pounds per square inch |
| q | Quartette (or quartet) |
| Rf | Retention factor |
| RT | Room temperature |
| Rt. | Retention time |
| s | Singlet |
| Tert | Tertiary |
| TEA | Triethylamine |
| TFA | Trifluoroacetic acid |
| THAB | Tetrahexylammonium bromide |
| THF | Tetrahydrofuran |
| UV | ultraviolet |
| VIS | visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above. Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of Formula (I), Formula (II) and Formula (III) according to the hereinafter described schemes and working examples.

In particular, the present invention relates to a process for the manufacture of compounds of Formula (I), wherein X is N and Y is NH, and all other substituents have the meaning as defined for Formula (I) in Claim 1, wherein a carboxylic acid ester of Formula (IV)

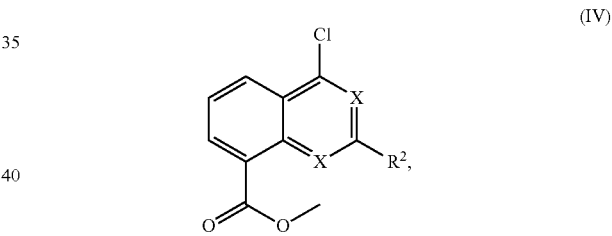

is reacted with a compound of Formula (V)

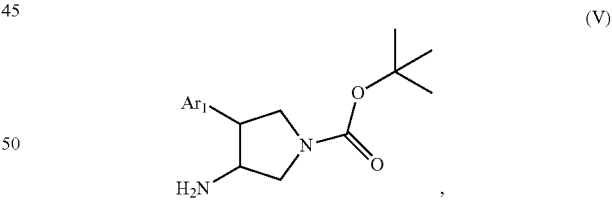

to yield a compound of Formula (VI)

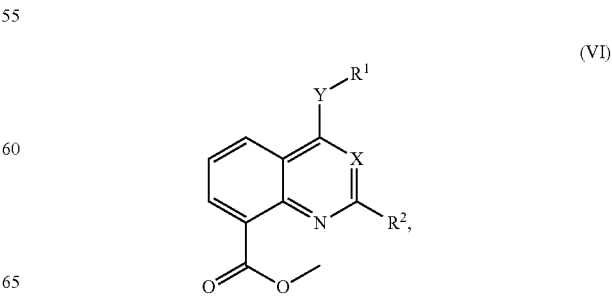

which is finally converted into the carboxylic amide of Formula (I)

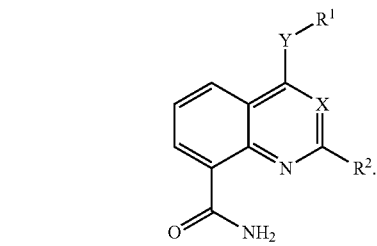

General Synthetic Procedures

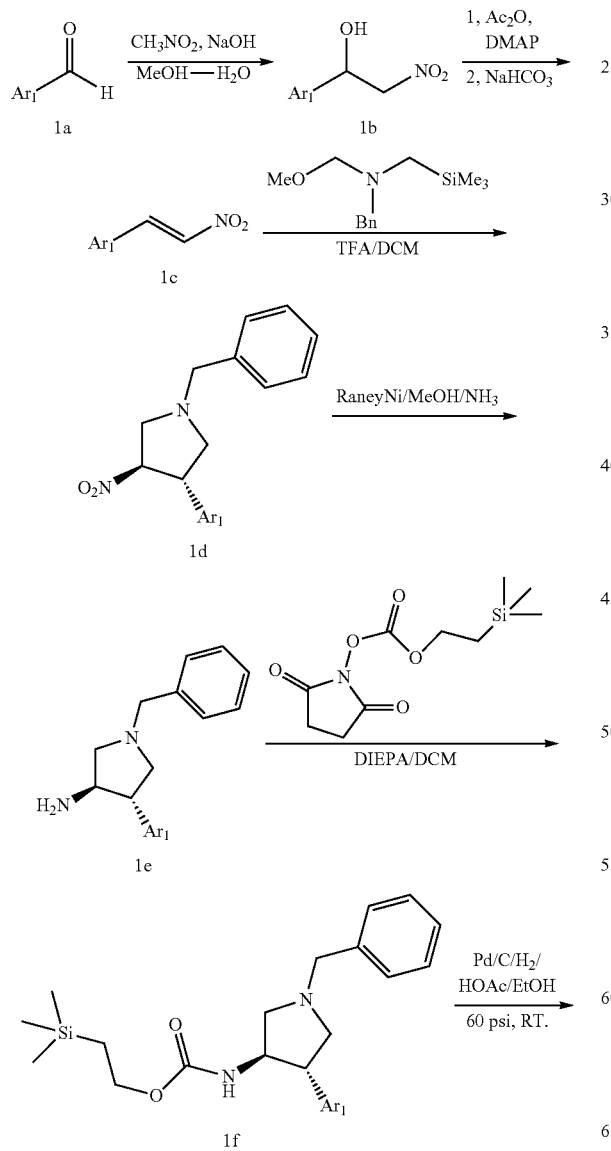

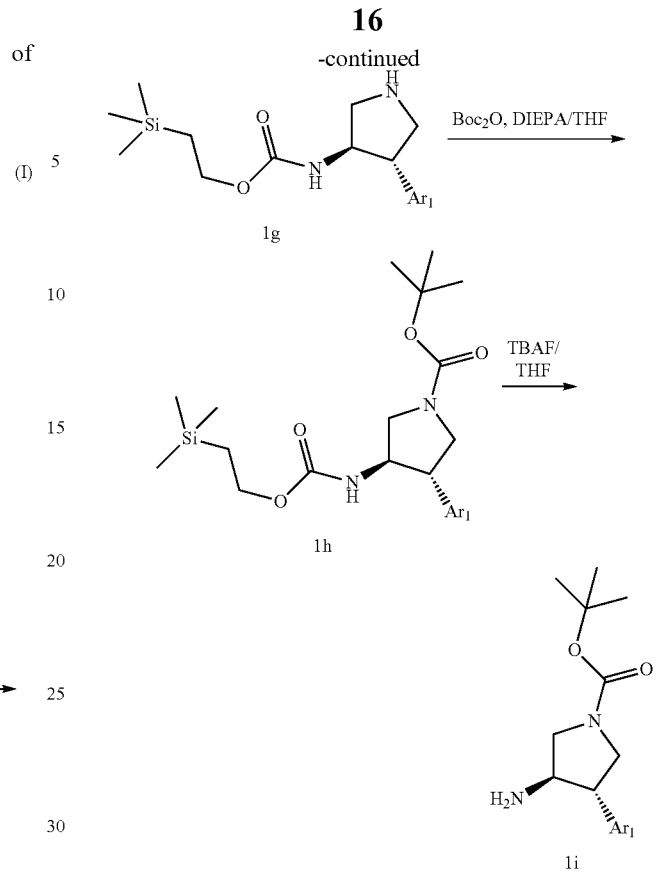

Arylaldehyde 1a was reacted with nitro methane under basic conditions to provide the hydroxyl derivative 1b, which was converted to the alkene 1c under acetic anhydride promoted elimination conditions. Cyclization of 1c with N-benzyl-1-methoxy-N-((trimethylsilyl)methyl)methanamine gave pyrrolidine derivative 1d. Reduction of the nitro group in 1d using Raney nickel as a catalyst, followed by the Teoc protection of the resulting amino moiety with N-[2-(trimethylsilyl)ethoxycarbonyloxy]succinimide gave 1f. The N-benzyl group of 1f was removed under hydrogenation conditions, and protected with di-tert-butyl dicarbonate to provide 1h. The Teoc protected primary amine in 1h was released upon treatment with tetra-n-butylammonium fluoride to provide 1i.

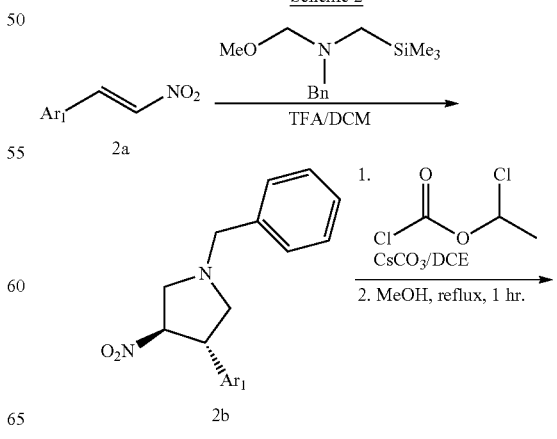

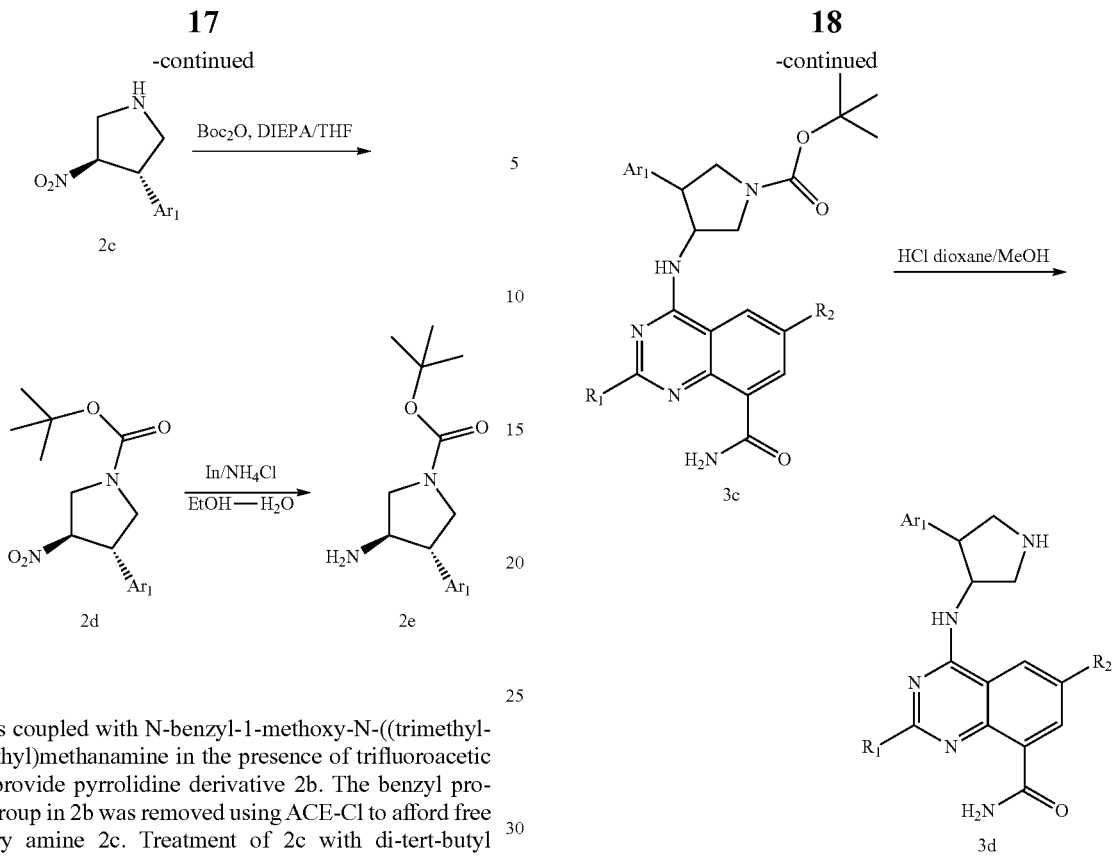

2a was coupled with N-benzyl-1-methoxy-N-((trimethylsilyl)methyl)methanamine in the presence of trifluoroacetic acid to provide pyrrolidine derivative 2b. The benzyl protecting group in 2b was removed using ACE-Cl to afford free secondary amine 2c. Treatment of 2c with di-tert-butyl dicarbonate, followed by indium promoted reduction of the nitro moiety gave compound 2e.

Scheme 3

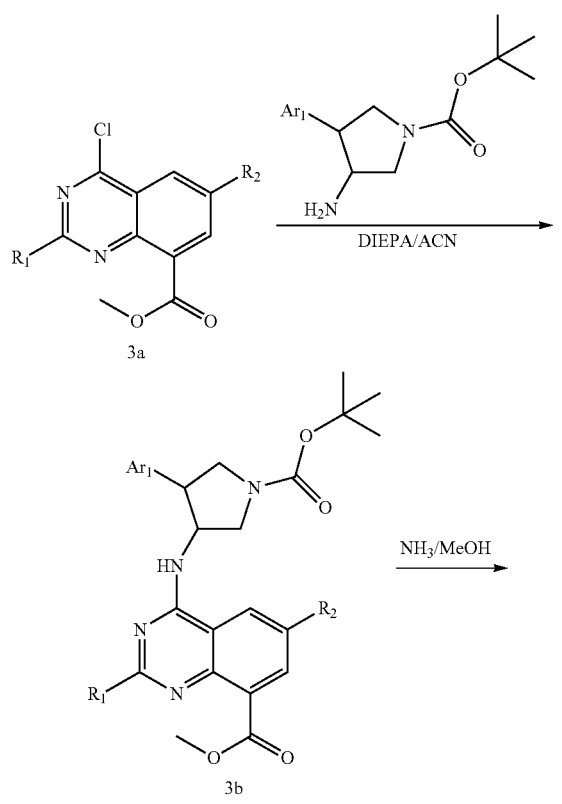

3a was coupled with 3-amino-4-aryl pyrrolidine to provide 3b. The methyl ester in 3b was converted to amide 3c by reacting with ammonia in methanol. Treatment of 3c with HCl in dioxane removed the Boc protecting group to give 3d.

Scheme 4

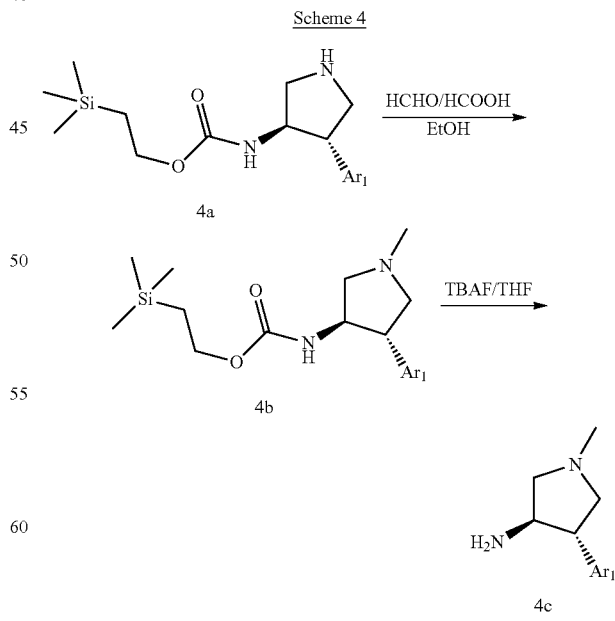

The pyrrolidine derivative 4a was treated with formaldehyde and formic acid to provide the N-methylpyrrolidine 4b.

The Teoc protected primary amine in 4b was release upon treatment with tetra-n-butylammonium fluoride to provide 4c.
The 3-amino-4-aryl pyrrolidine was reacted with 4-chloroquinoline-8-carbonitrile 5a under basic conditions to generate 5b, which was hydrolyzed to give amide 5c. Subsequent protecting group removal provided 5d.
Scheme 5
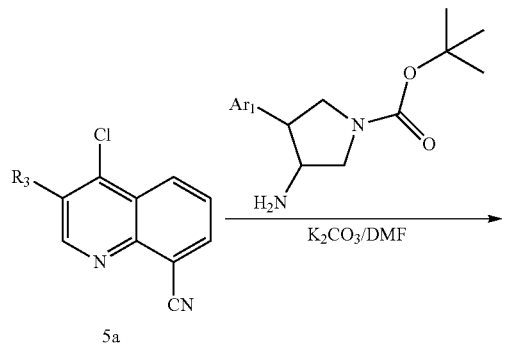
5a
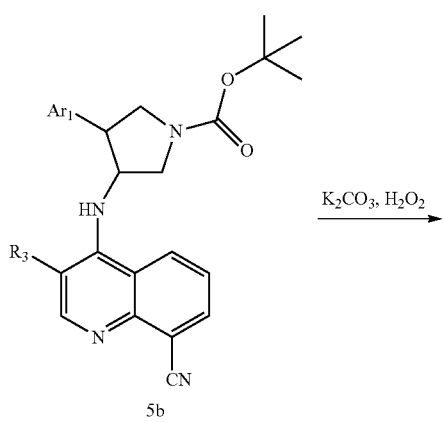
5b
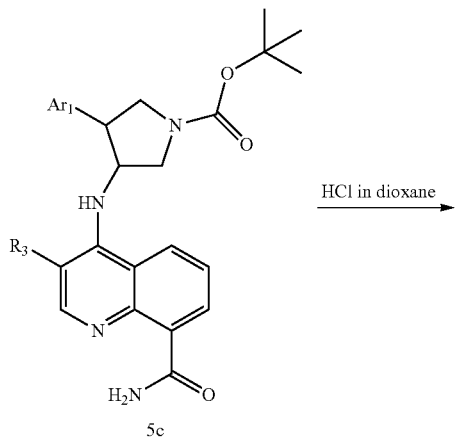
5c
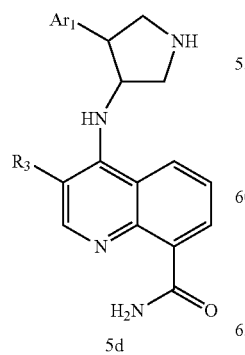
5d
Scheme 6
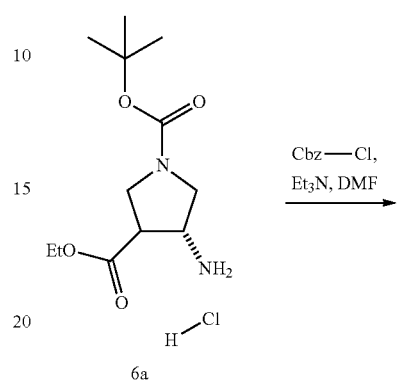
6a
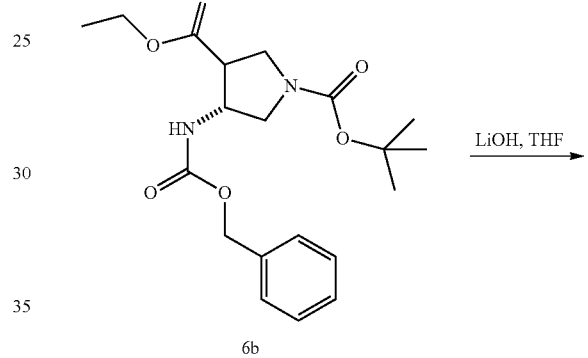
6b
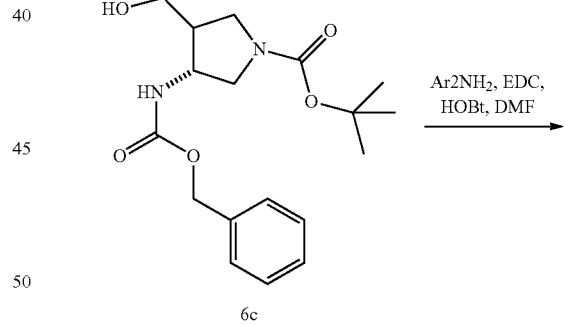
6c
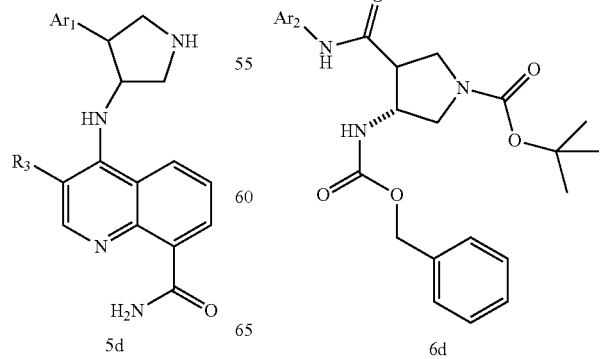
6d
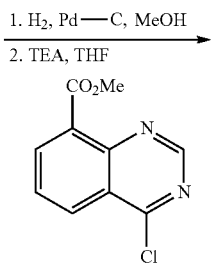

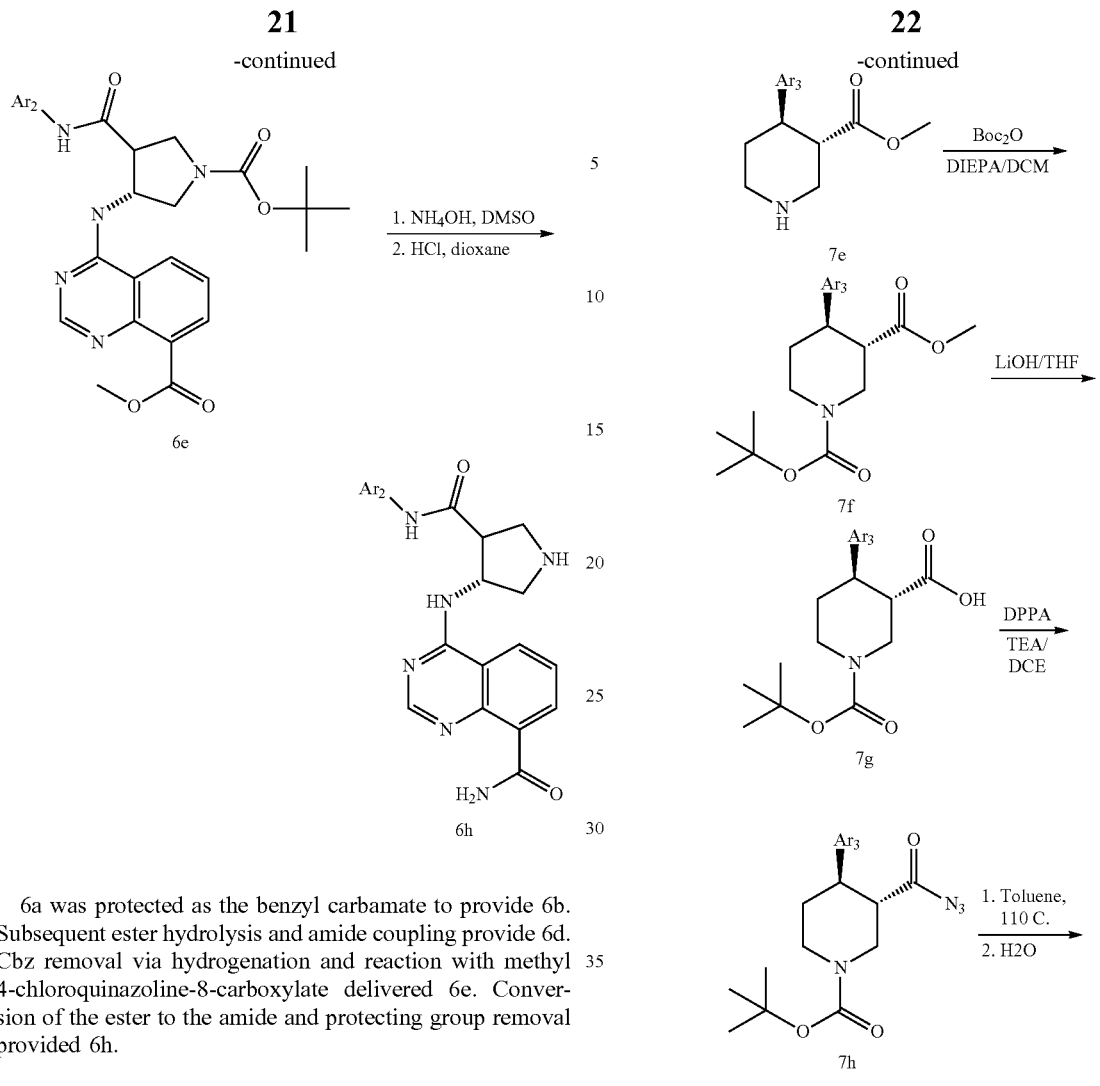

6a was protected as the benzyl carbamate to provide 6b. Subsequent ester hydrolysis and amide coupling provide 6d. Cbz removal via hydrogenation and reaction with methyl 4-chloroquinazoline-8-carboxylate delivered 6e. Conversion of the ester to the amide and protecting group removal provided 6h.

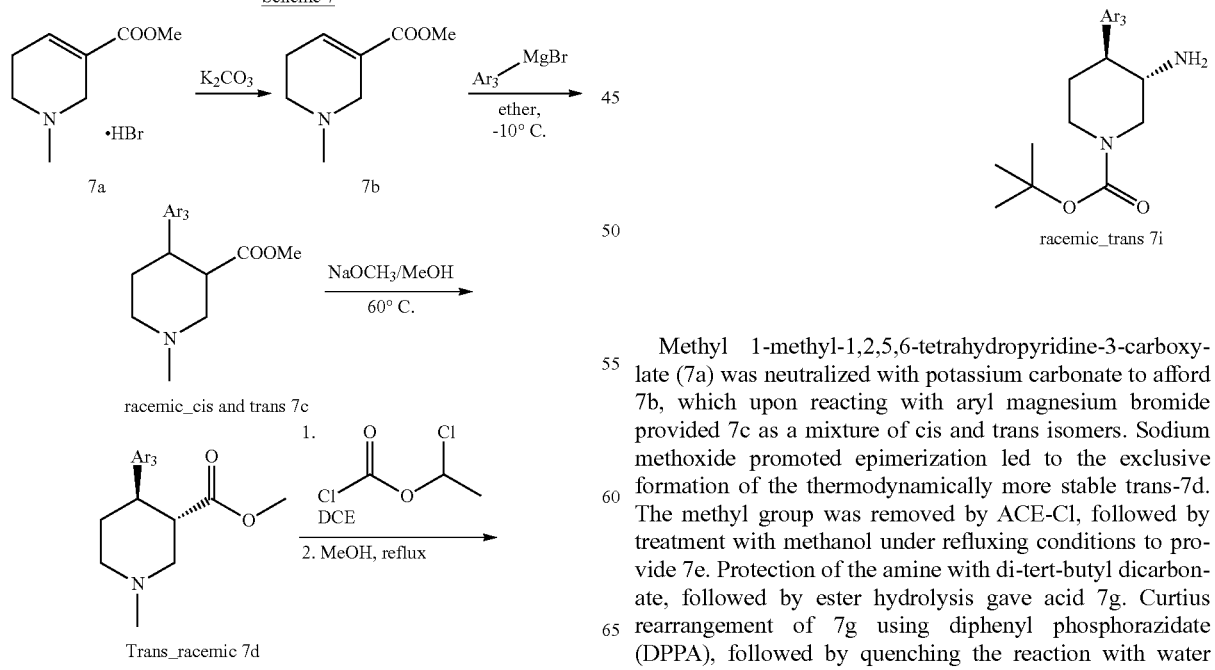

Methyl 1-methyl-1,2,5,6-tetrahydropyridine-3-carboxylate (7a) was neutralized with potassium carbonate to afford 7b, which upon reacting with aryl magnesium bromide provided 7c as a mixture of cis and trans isomers. Sodium methoxide promoted epimerization led to the exclusive formation of the thermodynamically more stable trans-7d. The methyl group was removed by ACE-Cl, followed by treatment with methanol under refluxing conditions to provide 7e. Protection of the amine with di-tert-butyl dicarbonate, followed by ester hydrolysis gave acid 7g. Curtius rearrangement of 7g using diphenyl phosphorazidate (DPPA), followed by quenching the reaction with water provided 7i.

Scheme 8
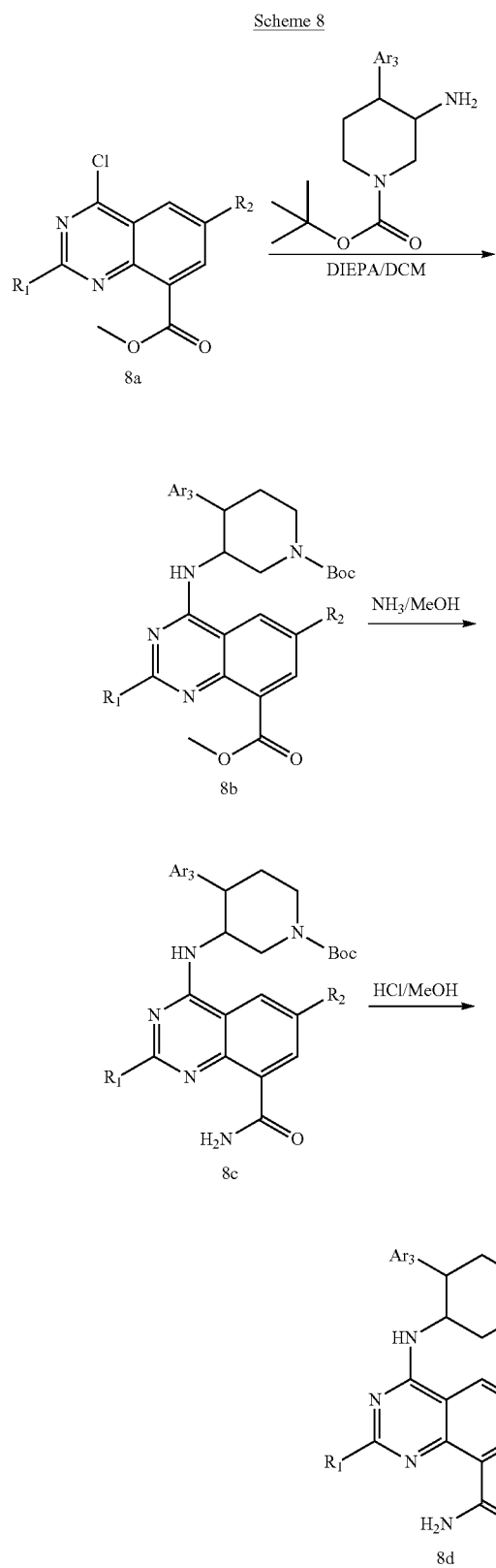
8a was coupled with 3-amino-4-aryl piperidine to generate 8b. Methyl ester aminolysis with ammonia in methanol, followed by the amine deprotection provided 8d.
Scheme 9
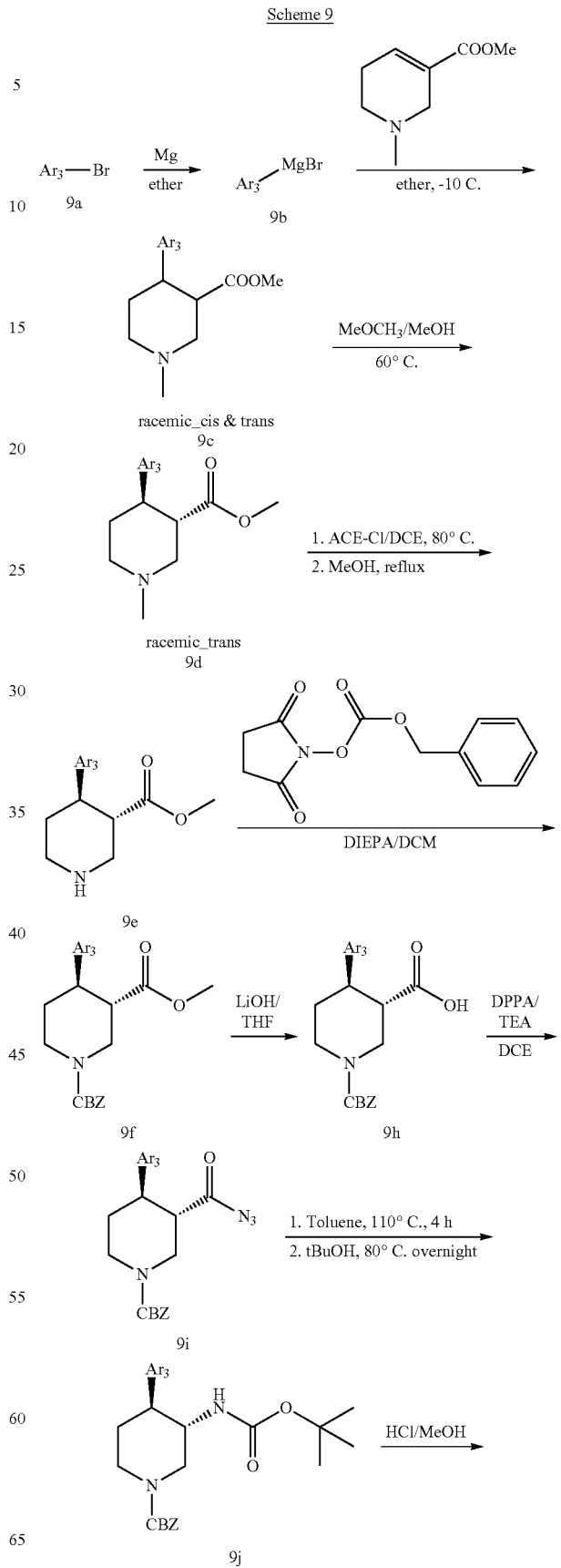

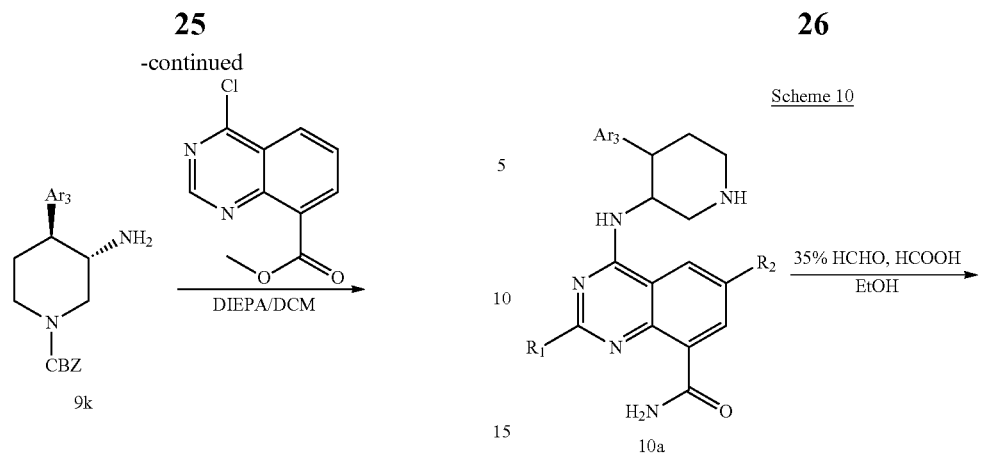

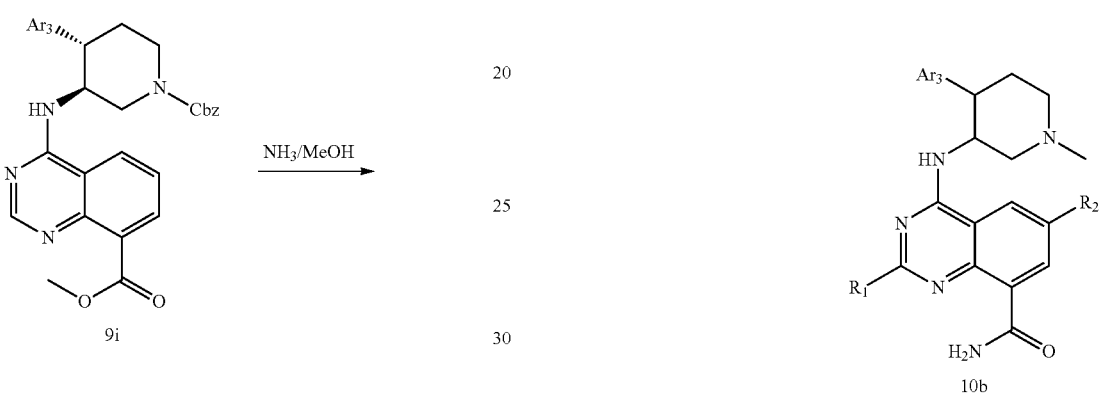

Addition of grignar reagent 9b to methyl 1-methyl-1,2,5,6-tetrahydropyridine-3-carboxylate gave 9c as a cis and trans mixture. Sodium methoxide promoted epimerization led to the exclusive formation of the thermodynamically more stable trans-9d. The methyl group was removed by using ACE-Cl, followed by treatment with methanol under refluxing conditions to provide 9e. Protection of the secondary amine as a benzyl carbamate, followed by ester hydrolysis gave 9h. Curtius rearrangement of 9h using diphenyl phosphorazidate (DPPA), followed by quenching the reaction with t-butanol provided Boc protected piperidine 9j. Boc removal under acidic conditions provided 9k, which was coupled with methyl 4-chloroquinazoline-8-carboxylate to give 9l. Aminolysis of the methyl ester with ammonia in methanol, followed by the Cbz removal provided desired 9n.

Scheme 10

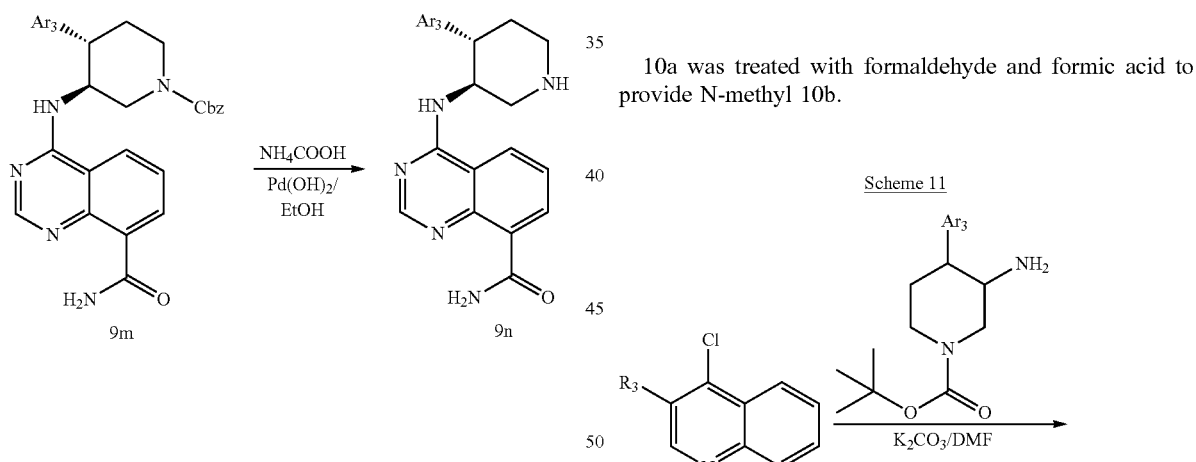

10a was treated with formaldehyde and formic acid to provide N-methyl 10b.

Scheme 11

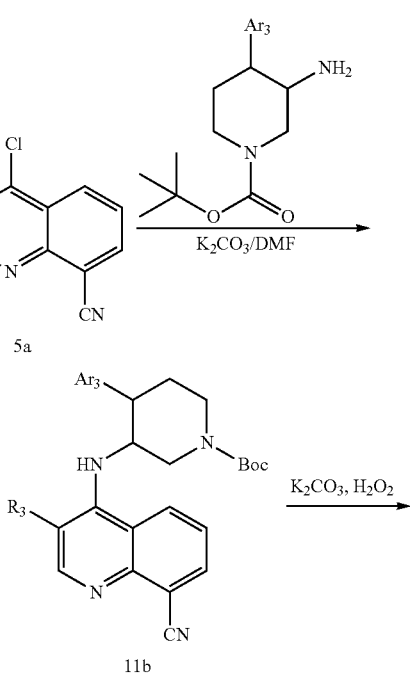

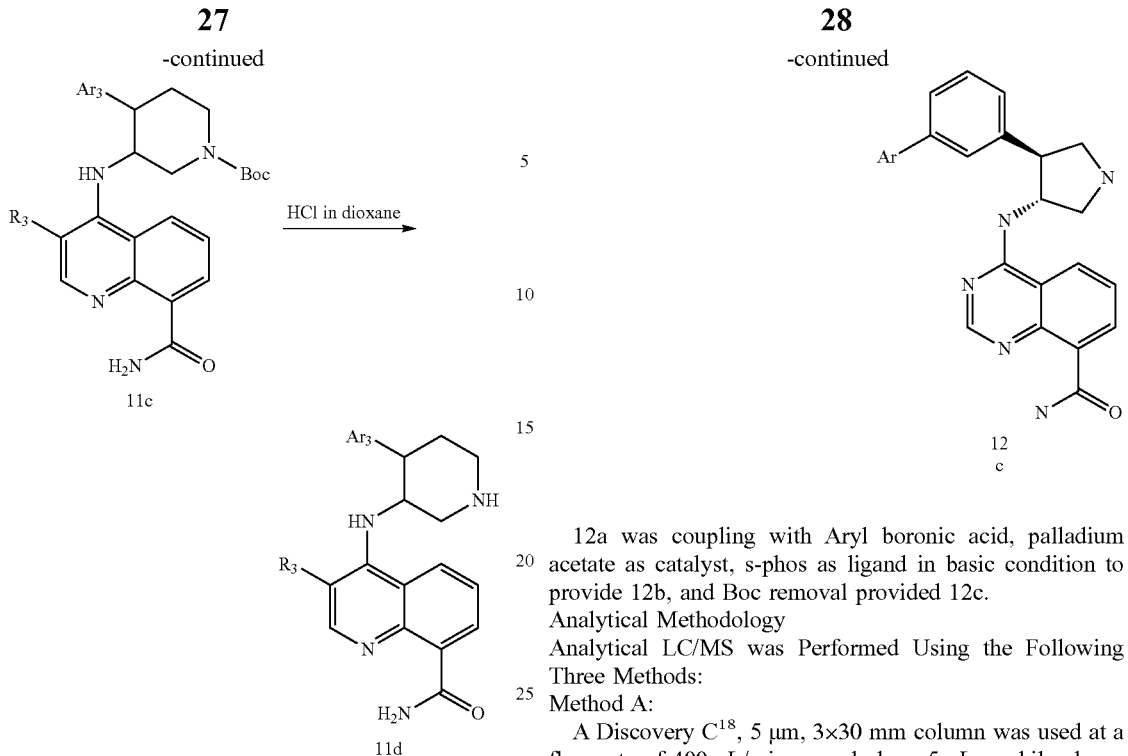

11c

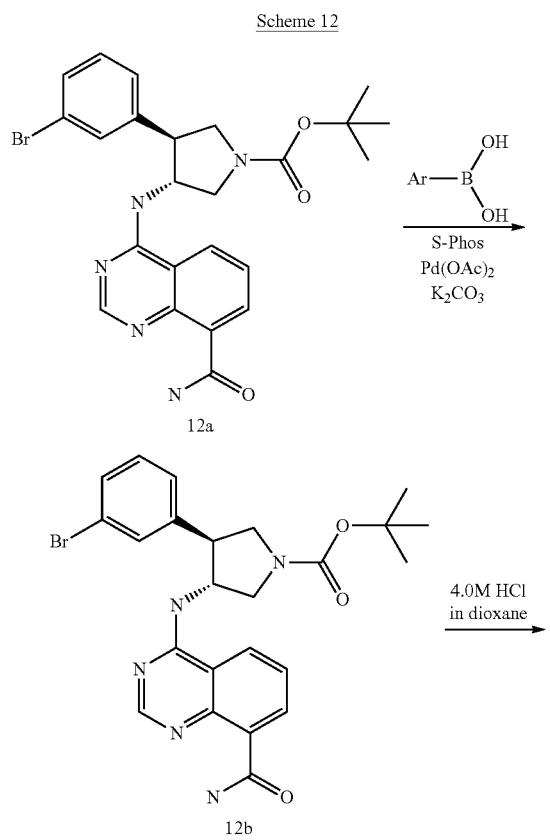

11d

As in Scheme 5, 5a was combined with 3-amino-4-aryl piperidine derivative to provide 11b. Nitrile hydrolysis and Boc removal provided 11d.

12c 12a was coupling with Aryl boronic acid, palladium acetate as catalyst, s-phos as ligand in basic condition to provide 12b, and Boc removal provided 12c.

Analytical Methodology

Analytical LC/MS was Performed Using the Following Three Methods:

Method A:

A Discovery $C^{18}$, 5 μm, 3×30 mm column was used at a flow rate of 400 μL/min, sample loop 5 μL, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+ modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B:

A Waters Symmetry $C^{18}$, 3.5 μm, 4.6×75 mm column at a flow rate of 1 mL/min, sample loop 10 μL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+ mode with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

Method C:

Gradient: 4.2 min/Flow: 2 ml/min 99:01-0:100 Water+ 0.1% (Vol.) TFA; Acetonitril+0.1% (Vol.) TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

Analytical Chiral HPLC

Analytical chiral HPLC was performed using a ChiralPak AD-H column (250×4.6 mm) from Daicel Chemical Industries, Ltd. on an Agilent 1100 Series system. The method used a 5.0 μL injection volume, with a flow rate of 1 mL/min of 100% methanol for 15 min at 25° C., and UV-detection at 254 and 280 nm.

Preparative HPLC

Preparative HPLC was performed using either a Waters Atlantis $dC_{18}$ OBD™ 10 μM (30×250 mm) column or a Waters Sunfire Prep $C_{18}$ OBD 10 μM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

EXAMPLES

The working examples presented below are intended to illustrate particular embodiments of the invention, and are not intended to limit the scope of the specification or the claims in any way.
Chemical Synthesis
In this section experimental details are provided for a number of Example compounds according to Formula (I), and synthesis intermediates thereof.
Synthesis Intermediates

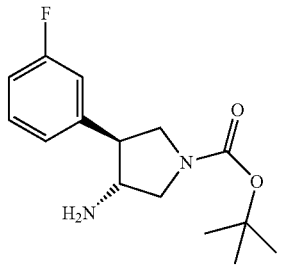

tert-Butyl 3-amino-4-(3-fluorophenyl)pyrrolidine-1-carboxylate (1)

1-(3-Fluoro-phenyl)-2-nitro-ethanol

A solution of 3-fluorobenzaldehyde (21.37 ml; 201.43 mmol; 1.00 eq.) and nitromethane (13.06 ml; 241.71 mmol; 1.20 eq.) in MeOH (40 ml) was cooled to −10° C. A solution of NaOH (8.46 g; 211.50 mmol; 1.05 eq.) in $H_2O$ (20 ml) was added over 10 min, keeping the temperature below −5° C. The reaction mixture was stirred at −5° C. for 15 min, during which the reaction solution solidified as a white solid. The reaction mixture was warmed to 0° C., and diluted with $H_2O$ (150 ml). Upon dissolution of all of the solids, HCl (4M, 100 ml) was added. The reaction mixture was extracted with DCM (300 ml×2). The combined extracts were washed with brine and concentrated to provide the desired intermediate (34.8 g, yield 93%).

1-Fluoro-3-((E)-2-nitro-vinyl)-benzene

N,N-Dimethylpyridin-4-amine (2.30 g; 18.80 mmol) was added to a solution of 1-(3-fluorophenyl)-2-nitroethanol (34.80 g; 187.95 mmol) in acetic anhydride (35.53 ml; 375.90 mmol) at 0° C., and stirred at RT for 72 h. The reaction mixture was quenched by pouring into a vigorously stirred satd. $NaHCO_3$ solution (400 mL). The desired intermediate was extracted with EtOAc (3×100 mL). The organic extracts were washed with satd. $NaHCO_3$, brine, dried over MgSO4, filtered, and concentrated to provide the desired intermediate (26.0 g, yield 83%).

Trans-1-Benzyl-3-(3-fluoro-phenyl)-4-nitro-pyrrolidine

N-benzyl-1-methoxy-N-[(trimethylsilyl)methyl]methanamine was added to a solution of 1-fluoro-3-[(E)-2-nitrovinyl]benzene (6.00 g; 35.90 mmol) in DCM (50 ml). The reaction solution was cooled to 0° C., TFA (0.30 ml; 3.95 mmol) was added drop wise, and stirred overnight at RT. The reaction solution was washed with $H_2O$ and brine, dried over MgSO4, filtered, and concentrated. The crude material was purified via Biotage (340 g column) eluting with 5% EtOAc in hexane to provide the desired product (5.5 g, yield 51%).

(Trans-1-Benzyl-4-(3-fluoro-phenyl)-pyrrolidin-3-ylamine

Trans-1-benzyl-3-(3-fluorophenyl)-4-nitropyrrolidine (5.50 g; 18.31 mmol) was dissolved in MeOH (300 mL). $NH_3$ (30 ml, 2.0M in MeOH) was added, and the solution was passed through the H cube (flow 1.5 min/min, full $H_2$, at 50° C.). The reaction solution was concentrated to provide the desired intermediate (4.6 g, yield 92%). LC-MS (M+H=271, obsd=271).

[Trans-1-Benzyl-4-(3-fluoro-phenyl)-pyrrolidin-3-yl]-carbamic acid propyl ester 1-({[2-(Trimethylsilyl)ethoxy]carbonyl}oxy)pyrrolidine-2,5-dione (4.5 g; 17.37 mmol) was added to a solution of trans-1-benzyl-4-(3-fluorophenyl)pyrrolidin-3-amine (4.5 g; 16.87 mmol) and DIEA (4.5 ml; 25.30 mmol) in DCM (50 ml) at 0° C., warmed to RT, and stirred for 1 hr at RT. The reaction solution was washed with brine, dried over $MgSO_4$, filtered, and concentrated. The crude material was purified was purified by Biotage eluting with a gradient of 30 to 60% EtOAc in hexane to provide the desired intermediate (6.0 g, yield 99%). LC-MS (M+H=415, obsd=415).

[Trans-4-(3-Fluoro-phenyl)-pyrrolidin-3-yl]-carbamic acid propyl ester

AcOH (2 mL) was added to a solution of 2-(trimethylsilyl)ethyl [trans-benzyl-4-(3-fluorophenyl)pyrrolidin-3-yl] carbamate (2.50 g; 6.03 mmol) in EtOH (150 ml). Pd/C (1.25 g, wet, 10% Pd) was then added, and the reaction mixture was put on a par shaker (60 Psi), and reacted for 2 h. The reaction mixture was filtered, and the filtrate was concentrated to provide the desired product (1.96 g, quantitative yield). LC-MS (M+H=325, obsd=325).

Trans-3-(3-Fluoro-phenyl)-4-propoxycarbonylamino-pyrrolidine-1-carboxylic acid tert-butyl ester Di-tert-butyl dicarbonate (1.27 g; 5.82 mmol) was added to a solution of 2-(trimethylsilyl)ethyl [trans-4-(3-fluorophenyl)pyrrolidin-3-yl]carbamate (1.80 g; 5.55 mmol) and DIEA (2.2 ml; 12.26 mmol) in DCM (100 ml), and stirred overnight at RT. The reaction mixture was concentrated, and the crude product was purified via Biotage eluting with a gradient of 20 to 60% EtOAc in hexanes to provide the desired intermediate (2.0 g, yield 85%). LC-MS (M+H=425, obsd=425).

1-Benzyl-4-(3-fluorophenyl)pyrrolidin-3-amine

Tert-butyl Trans-3-(3-fluorophenyl)-4-({[2-(trimethylsilyl)ethoxy]carbonyl}amino)-pyrrolidine-1-carboxylate (2.4 g; 5.76 mmol) and N,N,N-tributylbutan-1-aminium fluoride (20.00 ml; 1.00 M; 20.00 mmol) was dissolved in MeOH, and stirred overnight at RT. The crude product was purified via Biotage eluting with a gradient of 5 to 10% MeOH in DCM to provide 1 (1.61 g, yield 79%). LC-MS (M+H=281, obsd=281). $^1$HNMR (DMSO-d6) δ 1.39 (s, 9H), 1.55 (s, 1H), 2.90-2.99 (m, 2H), 3.24-3.26 (m, 1H), 3.33-3.37 (m, 1H), 3.55-3.57 (m, 1H), 3.60-3.68 (m, 1H), 3.70-3.72 (m, 1H), 7.05-7.06 (m, 1H), 7.13-7.15 (m, 2H), 7.35-7.36 (m, 1H).

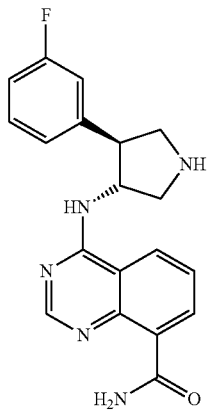

trans racemic 4-((4-(3-fluorophenyl)pyrrolidin-3-yl)amino)quinazoline-8-carboxamide (2)

IC$_{50}$p70S6K [uM]: 0.003

Methyl 4-((1-(tert-butoxycarbonyl)-4-(3-fluorophenyl)pyrrolidin-3-yl)amino)quinazoline-8-carboxylate Methyl 4-chloroquinazoline-8-carboxylate (80.00 mg; 0.36 mmol), DIEA (0.13 ml; 0.72 mmol), and racemic trans tert-butyl 3-amino-4-(3-fluorophenyl)pyrrolidine-1-carboxylate (109 mg; 0.37 mmol) were dissolved in CH$_3$CN, and stirred overnight at RT. The reaction mixture was concentrated, redissolved in methanolic NH$_3$ (1.50 ml; 7.00 M; 10.50 mmol), and stirred for 72 h at RT. The reaction mixture was concentrated to provide the desired intermediate. LC-MS (M+H=452, obsd=452).

4-((4-(3-fluorophenyl)pyrrolidin-3-yl)amino)quinazoline-8-carboxamide

HCl in dioxane (1.5 ml; 4.00 M; 6.00 mmol) was added to a solution of tert-butyl 3-{[8-(aminocarbonyl)quinazolin-4-yl]amino}-4-(3-fluorophenyl)-pyrrolidine-1-carboxylate (162 mg; 0.36 mmol) in MeOH (1.5 ml), and stirred overnight at RT. The resulting precipitate was filtered washed with MeOH and ether, and dried under vacuum to provide 2 (67 mg, 44% yield) as an HCl salt. LC-MS (M+H=352, obsd=352). $^1$HNMR (DMSO-d6) δ 2.86-2.88 (m, 2H), 3.39-3.42 (m, 2H), 4.09-4.11 (d, 1H), 4.81-4.84 (m, 1H), 7.05 (t, 1H), 7.17 (t, 1H), 7.32 (q 1H), 7.62 (t, 1H), 7.81 (d, 1H), 8.52-8.65 (m, 4H), 10.33 (d, 1H).

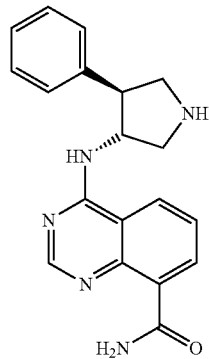

trans racemic 4-((4-phenylpyrrolidin-3-yl)-amino)quinazoline-8-carboxamide (3)

IC$_{50}$p70S6K [uM]: 0.0049

The compound was synthesized according to the procedure described for the preparation of example 2 using trans racemic tert-butyl 3-amino-4-phenylpyrrolidine-1-carboxylate and methyl 4-chloroquinazoline-8-carboxylate. LC-MS (M+H=334, obsd=334). $^1$HNMR (DMSO-d6) δ 3.42-3.45 (m, 2H), 3.78-3.86 (m, 2H), 4.04-4.08 (m, 1H), 5.23 (t, 1H), 7.26-7.32 (m, 1H), 7.32-7.34 (m, 2H), 7.48-7.05 (m, 2H), 7.84 (t, 1H), 8.15 (s, 1H), 8.54 (d, 1H), 8.77 (s, 1H), 8.98 (s, 1H), 9.80 (s, 2H).

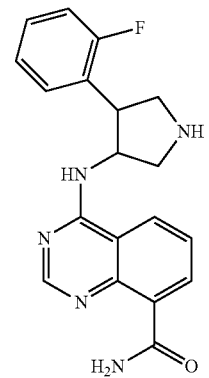 [SMILES: NC(=O)c1cccc2c(NC3CNCC3c3ccccc3F)ncnc12]

4-((4-(2-fluorophenyl)pyrrolidin-3-yl)amino)quinazoline-8-carboxamide (4)

IC$_{50}$p70S6K [uM]: 0.0035

The compound was synthesized according to the procedure described for the preparation of example 2 using trans racemic tert-butyl 3-amino-4-(2-fluorophenyl)pyrrolidine-1-carboxylate and methyl 4-chloroquinazoline-8-carboxylate. LC-MS (M+H=352, obsd=352).

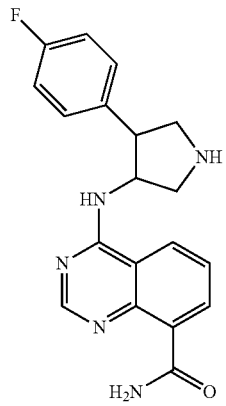 [SMILES: NC(=O)c1cccc2c(NC3CNCC3c3ccc(F)cc3)ncnc12]

4-((4-(4-fluorophenyl)pyrrolidin-3-yl)amino)quinazoline-8-carboxamide (5)

$IC_{50}$p70S6K [uM]: 0.0026

The compound was synthesized according to the procedure described for the preparation of example 2 using tert-butyl 3-amino-4-(4-fluorophenyl)pyrrolidine-1-carboxylate and methyl 4-chloroquinazoline-8-carboxylate. LC-MS (M+H=352, obsd=352).

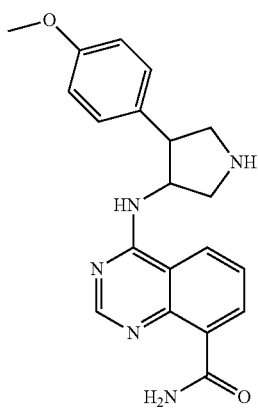 [SMILES: COc1ccc(C2CNCC2Nc2ncnc3c(C(N)=O)cccc23)cc1]

4-((4-(4-methoxyphenyl)pyrrolidin-3-yl)amino)quinazoline-8-carboxamide (6)

$IC_{50}$p70S6K [uM]: 0.002

The compound was synthesized according to the procedure described for the preparation of example 2 using tert-butyl 3-amino-4-(4-methoxyphenyl)-pyrrolidine-1-carboxylate and methyl 4-chloroquinazoline-8-carboxylate. LC-MS (M+H=364, obsd=364).

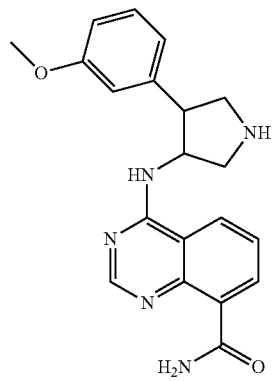 [SMILES: COc1cccc(C2CNCC2Nc2ncnc3c(C(N)=O)cccc23)c1]

4-((4-(3-methoxyphenyl)pyrrolidin-3-yl)amino)quinazoline-8-carboxamide (7)

$IC_{50}$p70S6K [uM]: 0.0026

The compound was synthesized according to the procedure described for the preparation of example 2 using tert-butyl 3-amino-4-(3-methoxyphenyl)-pyrrolidine-1-carboxylate and methyl 4-chloroquinazoline-8-carboxylate.
LC-MS (M+H=364, obsd=364).

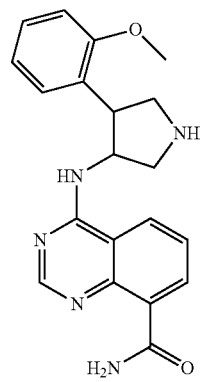 [SMILES: COc1ccccc1C1CNCC1Nc1ncnc2c(C(N)=O)cccc12]

4-((4-(2-methoxyphenyl)pyrrolidin-3-yl)amino)quinazoline-8-carboxamide (8)

$IC_{50}$p70S6K [uM]: 0.018

The compound was synthesized according to the procedure described for the preparation of example 2 using tert-butyl 3-amino-4-(2-methoxyphenyl)-pyrrolidine-1-carboxylate and methyl 4-chloroquinazoline-8-carboxylate.
LC-MS (M+H=364, obsd=364).

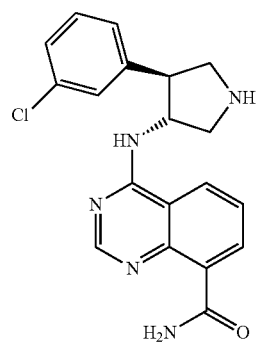

trans, racemic 4-((4-(3-chlorophenyl)pyrrolidin-3-yl)amino)quinazoline-8-carboxamide (9)

IC$_{50}$p70S6K [uM]: 0.0013

The compound was synthesized according to the procedure described for the preparation of example 2 using trans, racemic tert-butyl 3-amino-4-(3-chlorophenyl)pyrrolidine-1-carboxylate and methyl 4-chloroquinazoline-8-carboxylate. LC-MS (M+H=368, obsd=368/370).

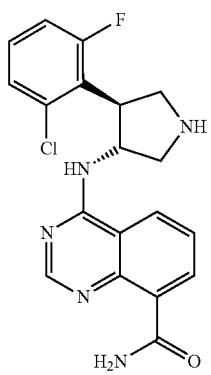

trans, racemic 4-((4-(2-chloro-6-fluorophenyl)pyrrolidin-3-yl)amino)-quinazoline-8-carboxamide (10)

IC$_{50}$p70S6K [uM]: 0.007

The compound was synthesized according to the procedure described for the preparation of example 2 using trans, racemic tert-butyl 3-amino-4-(2-chloro-6-fluorophenyl)pyrrolidine-1-carboxylate and methyl 4-chloro-quinazoline-8-carboxylate. LC-MS (M+H=386, obsd=386/388).

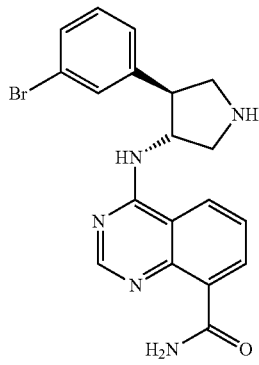

trans, racemic 4-((4-(3-bromophenyl)pyrrolidin-3-yl)amino)quinazoline-8-carboxamide (11)

racemic 1-benzyl-3-(3-bromophenyl)-4-nitropyrrolidine

N-Benzyl-1-methoxy-N-[(trimethylsilyl)methyl]methanamine (5.05 g; 20.00 mmol) was added to a solution of 1-bromo-3-[(E)-2-nitrovinyl]benzene (3.80 g; 16.66 mmol) in DCM (50 ml), and cooled to 0° C. TFA (0.14 ml; 1.83 mmol) was added, and the reaction was stirred overnight at RT. The reaction mixture was washed with water and brine, dried over MgSO$_4$, filtered and concentrated. The crude product was purified via Biotage (100 g column) eluting with 5% EtOAc in hexane to provide the desired intermediate. LC-MS (M+H=362, obsd=360/362).

tert-butyl 3-(3-bromophenyl)-4-nitropyrrolidine-1-carboxylate

Cs$_2$CO$_3$ (0.47 g; 1.45 mmol) and 1-chloroethyl chloridocarbonate (2.00 ml; 18.33 mmol) were added to a solution of (3R,4S)-1-benzyl-3-(3-bromophenyl)-4-nitropyrrolidine (2.62 g; 7.25 mmol) in DCE (100 ml), and stirred at 80° C. for 2 h. The reaction mixture was filtered, the filtrate was concentrated, and the residue was redissolved in MeOH (100 ml). The reaction solution was stirred at 60° C. for 2 h, and concentrated to provide a yellow oil.

The above intermediate, DIEA (3.91 ml; 21.76 mmol), and di-tert-butyl dicarbonate (1.90 g; 8.70 mmol) were dissolved in DCM (100 ml), and stirred overnight at RT. The reaction solution was washed with brine, dried over MgSO$_4$, filtered and concentrated. The crude product was purified via Biotage eluting with a gradient of 10 to 20% EtOAc in hexanes to provide the desired intermediate (1.11 g, 41% yield). LC-MS (M+H=272, obsd=270/272).

tert-butyl 3-amino-4-(3-bromophenyl)pyrrolidine-1-carboxylate tert-Butyl 3-(3-bromophenyl)-4-nitropyrrolidine-1-carboxylate (1.10 g; 2.96 mmol), indium (3.40 g; 29.63 mmol), and ammonium chloride (1.59 g; 29.63 mmol) were dissolved in H$_2$O (70 ml) and EtOH (70 ml) and refluxed for 4 h. The reaction mixture was filtered, and the filtrate was concentrated. The resulting residue was diluted with DCM, washed with brine, dried over MgSO$_4$, filtered, and concentrated. LC-MS (M+H=342, obsd=340/342).

The compound was synthesized according to the procedure described for the preparation of example 2 using the above intermediate, trans racemic tert-butyl 3-amino-4-(3-bromophenyl)pyrrolidine-1-carboxylate, and methyl 4-chloroquinazoline-8-carboxylate. LC-MS (M+H=413, obsd=413).

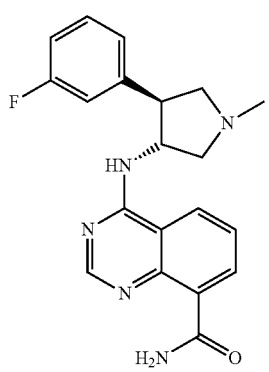

trans, racemic 4-((4-(3-fluorophenyl)-1-methylpyrrolidin-3-yl)amino)quinazoline-8-carboxamide (12)

IC$_{50}$p70S6K [uM]: 0.023

2-(trimethylsilyl)ethyl (4-(3-fluorophenyl)-1-methylpyrrolidin-3-yl)carbamate 2-(Trimethylsilyl)ethyl [4-(3-fluorophenyl)pyrrolidin-3-yl]carbamate (300.00 mg; 0.92 mmol), formic acid (0.10 ml;

2.31 mmol), and formaldehyde (0.09 ml; 1.11 mmol) were dissolved in EtOH, and stirred for 3 h at 80° C. The reaction solution was concentrated to provide the desired intermediate. LC-MS (M+H=339, obsd=339).

4-(3-fluorophenyl)-1-methylpyrrolidin-3-amine 2-(trimethylsilyl)ethyl [4-(3-fluorophenyl)-1-methylpyrrolidin-3-yl]carbamate (300.00 mg; 0.89 mmol), and N,N,N-tributylbutan-1-aminium fluoride (5.00 ml; 1.00 M; 5.00 mmol; 5.64 eq.) were dissolved in MeOH, and stirred at RT for 3 h. The crude product was purified via prep HPLC to provide the desired intermediate (150 mg, 55% yield). LC-MS (M+H=195, obsd=195).

The compound was synthesized according to the procedure described for the preparation of example 2 using the intermediate above, trans, racemic 4-(3-fluorophenyl)-1-methylpyrrolidin-3-amine, and methyl 4-chloroquinazoline-8-carboxylate. LC-MS (M+H=366, obsd=366).

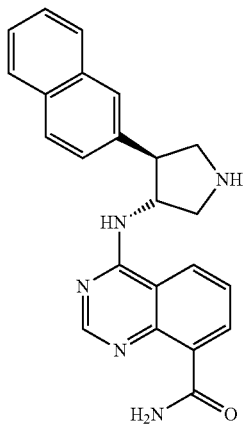

trans, racemic 4-((–4-(naphthalen-2-yl)pyrrolidin-3-yl)amino)quinazoline-8-carboxamide (13)

The compound was synthesized according to the procedure described for the preparation of example 2 using trans, racemic, tert-butyl 3-amino-4-(naphthalen-2-yl)pyrrolidine-1-carboxylate and methyl 4-chloroquinazoline-8-carboxylate. LC-MS (M+H=384, obsd=384).

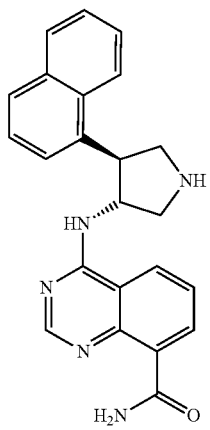

trans, racemic 4-((4-(naphthalen-1-yl)pyrrolidin-3-yl)amino)quinazoline-8-carboxamide (14)

The compound was synthesized according to the procedure described for the preparation of example 2 using trans, racemic tert-butyl 3-amino-4-(naphthalen-1-yl)pyrrolidine-1-carboxylate and methyl 4-chloroquinazoline-8-carboxylate. LC-MS (M+H=384, obsd=384).

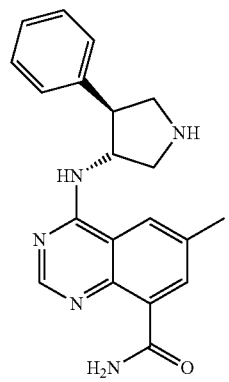

6-methyl-4-((4-phenylpyrrolidin-3-yl)amino)quinazoline-8-carboxamide (15)

IC$_{50}$p70S6K [nM]: 349

The compound was synthesized according to the procedure described for the preparation of example 2 using trans, racemic tert-butyl 3-amino-4-phenylpyrrolidine-1-carboxylate and 4-chloro-6-methylquinazoline-8-carboxamide. LC-MS (M+H=348, obsd=348).

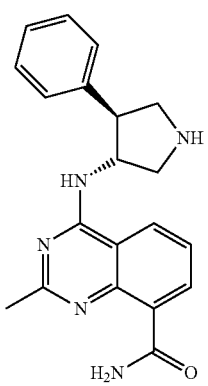

2-methyl-4-((4-phenylpyrrolidin-3-yl)amino)quinazoline-8-carboxamide (16)

IC$_{50}$p70S6K [uM]: 0.006

The compound was synthesized according to the procedure described for the preparation of example 2 using trans, racemic tert-butyl 3-amino-4-phenylpyrrolidine-1-carboxylate and 4-chloro-2-methylquinazoline-8-carboxamide. LC-MS (M+H=348, obsd=348).

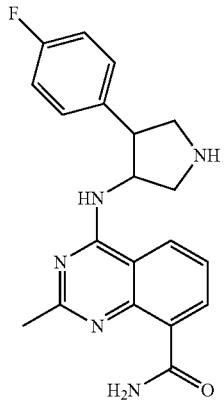 [SMILES: Cc1nc(NC2CNCC2c2ccc(F)cc2)c2cccc(C(N)=O)c2n1]

4-((4-(4-fluorophenyl)pyrrolidin-3-yl)amino)-2-methylquinazoline-8-carboxamide (17)

IC$_{50}$p70S6K [uM]: 0.0024

The compound was synthesized according to the procedure described for the preparation of example 2 using tert-butyl 3-amino-4-(4-fluorophenyl)pyrrolidine-1-carboxylate and 4-chloro-2-methylquinazoline-8-carboxamide.

LC-MS (M+H=366, obsd=366).

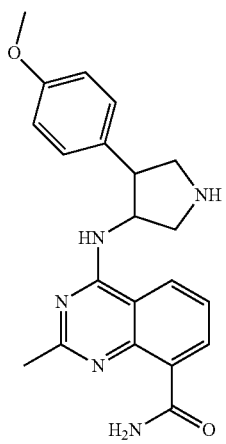 [SMILES: COc1ccc(C2CNCC2Nc2nc(C)nc3c(C(N)=O)cccc23)cc1]

4-((4-(4-methoxyphenyl)pyrrolidin-3-yl)amino)-2-methylquinazoline-8-carboxamide (18)

IC$_{50}$p70S6K [uM]: 0.0018

The compound was synthesized according to the procedure described for the preparation of example 2 using tert-butyl 3-amino-4-(4-methoxyphenyl)pyrrolidine-1-carboxylate and 4-chloro-2-methylquinazoline-8-carboxamide.

LC-MS (M+H=378, obsd=378).

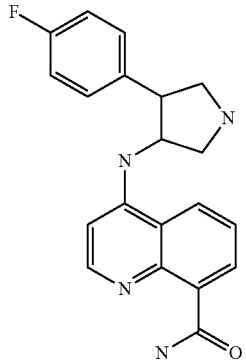 [SMILES: NC(=O)c1cccc2c(NC3CNCC3c3ccc(F)cc3)ccnc12]

4-((4-(4-fluorophenyl)-1-methylpyrrolidin-3-yl)amino)quinoline-8-carboxamide (19)

IC$_{50}$p70S6K [uM]: 0.5

3-(8-Cyano-quinolin-4-ylamino)-4-(4-fluoro-phenyl)-pyrrolidine-1-carboxylic acid tert-butyl ester 4-Chloroquinoline-8-carbonitrile (200 mg; 1.06 mmol), tert-butyl 3-amino-4-(4-fluorophenyl)pyrrolidine-1-carboxylate (386 mg; 1.38 mmol), and K$_2$CO$_3$ (732 mg; 5.30 mmol) were dissolved in DMF (7 mL), and stirred at 80-100° C. for 7 days. The reaction material was purified directly via HPLC to provide the desired intermediate (50 mgs). LC-MS (M+H=433, obsd=433). $^1$H NMR (400 MHz, DMSO-D$_6$): 3.3890 (m, 2H), 3.8405 (m, 2H), 4.1107 (m, 1H), 4.9560 (m, 1H), 6.7967 (m, 1H), 7.1788 (t, 2H), 7.5442 (m, 2H), 7.8425 (m, 1H), 8.2160 (s, 1H), 8.5086 (m, 2H), 8.7933 (m, 1H), 9.1442 (d, 1H), 9.8576 (m, 1H), 9.9730 (m, 1H), 10.0985 (m, 1H).

tert-butyl 3-((8-cyanoquinolin-4-yl)amino)-4-(4-fluorophenyl)pyrrolidine-1-carboxylate tert-Butyl 3-[(8-cyanoquinolin-4-yl)amino]-4-(4-fluorophenyl)pyrrolidine-1-carboxylate (20 mg; 0.05 mmol) and K$_2$CO$_3$ (51 mg; 0.37 mmol) were dissolved in DMSO (5 mL). H$_2$O$_2$ (179 mg; 1.85 mmol) was added drop wise, and the reaction mixture was stirred overnight at 50° C. The crude was purified via prep HPLC to provide the desired intermediate (35 mg). LC-MS (M+H=451, obsd=451).

4-((4-(4-fluorophenyl)-1-methylpyrrolidin-3-yl)amino)quinoline-8-carboxamide tert-Butyl 3-{[8-(aminocarbonyl)quinolin-4-yl]amino}-4-(4-fluorophenyl)pyrrolidine-1-carboxylate (25 mg; 0.02 mmol) was dissolved in HCl in dioxane (0.06 ml; 4.00 M; 0.22 mmol), and stirred for 30 minutes. The resulting precipitate was filtered, washed with ether and then dried under vacuum to provide 14 (21 mg). LC-MS (M+H=351, obsd=351). $^1$H NMR (400 MHz, DMSO-D$_6$): 3.3890 (m, 2H), 3.8405 (m, 2H), 4.1107 (m, 1H), 4.9560 (m, 1H), 6.7967 (m, 1H), 7.1788 (t, 2H), 7.5442 (m, 2H), 7.8425 (m, 1H), 8.2160 (s, 1H), 8.5086 (m, 2H), 8.7933 (m, 1H), 9.1442 (d, 1H), 9.8576 (m, 1H), 9.9730 (m, 1H), 10.0985 (m, 1H).

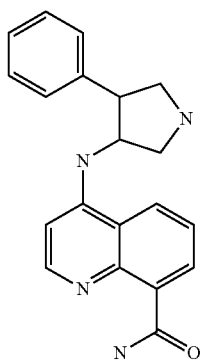 [SMILES: NC(=O)c1cccc2c(NC3CNCC3c3ccccc3)ccnc12]

4-((4-phenylpyrrolidin-3-yl)amino)quinoline-8-carboxamide (20)

The compound was synthesized according to the procedure described for the preparation of example 19 using tert-butyl 3-amino-4-phenyl pyrrolidine-1-carboxylate and methyl 4-chloroquinoline-8-carbonitrile. LC-MS (M+H=333, obsd=333).

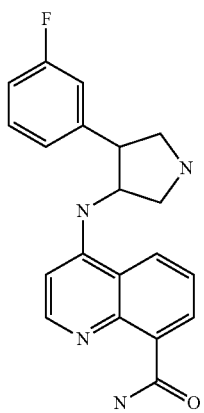 [SMILES: NC(=O)c1cccc2c(NC3CNCC3c3cccc(F)c3)ccnc12]

4-((4-(3-fluorophenyl)pyrrolidin-3-yl)amino)quinoline-8-carboxamide (21)

IC$_{50}$p70S6K [uM]: 0.013
The compound was synthesized according to the procedure described for the preparation of example 19 using tert-butyl 3-amino-4-(3-fluorophenyl)pyrrolidine-1-carboxylate and 4-chloroquinoline-8-carbonitrile. LC-MS (M+H=351, obsd=351).

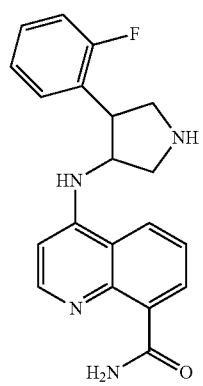

4-((4-(2-fluorophenyl)pyrrolidin-3-yl)amino)quinoline-8-carboxamide (22)

IC$_{50}$p70S6K [uM]: 0.0094
The compound was synthesized according to the procedure described for the preparation of example 19 using tert-butyl 3-amino-4-(2-fluorophenyl)pyrrolidine-1-carboxylate and 4-chloroquinoline-8-carbonitrile. LC-MS (M+H=351, obsd=351).

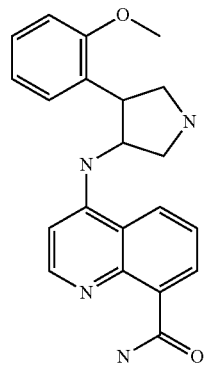 [SMILES: COc1ccccc1C1CNCC1Nc1ccnc2c(C(N)=O)cccc12]

4-((4-(2-methoxyphenyl)pyrrolidin-3-yl)amino)quinoline-8-carboxamide (23)

IC$_{50}$p70S6K [uM]: 0.046
The compound was synthesized according to the procedure described for the preparation of example 19 using tert-butyl 3-amino-4-(2-methoxyphenyl)pyrrolidine-1-carboxylate and methyl 4-chloroquinoline-8-carbonitrile. LC-MS (M+H=363, obsd=363).

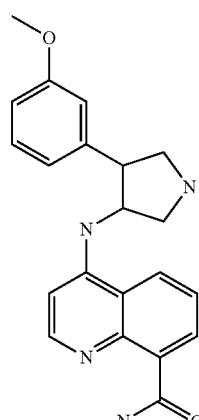

4-((4-(3-methoxyphenyl)pyrrolidin-3-yl)amino)quinoline-8-carboxamide (24)

The compound was synthesized according to the procedure described for the preparation of example 19 using tert-butyl 3-amino-4-(3-methoxyphenyl)pyrrolidine-1-carboxylate and 4-chloroquinoline-8-carbonitrile. LC-MS (M+H=363, obsd=363).

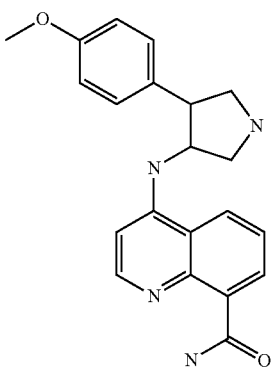 [SMILES: COc1ccc(C2CNCC2Nc2ccnc3c(C(N)=O)cccc23)cc1]

4-((4-(4-methoxyphenyl)pyrrolidin-3-yl)amino)quinoline-8-carboxamide (25)

The compound was synthesized according to the procedure described for the preparation of example 19 using tert-butyl 3-amino-4-(4-methoxyphenyl)pyrrolidine-1-carboxylate and 4-chloroquinoline-8-carbonitrile. LC-MS (M+H=363, obsd=363).

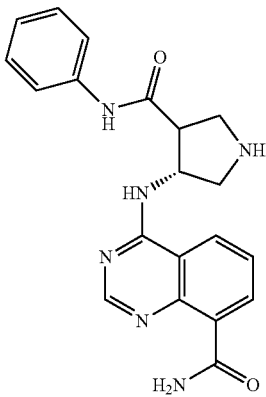 [SMILES: NC(=O)c1cccc2c(N[C@H]3CNCC3C(=O)Nc3ccccc3)ncnc12]

trans-4-(4-Phenylcarbamoyl-pyrrolidin-3-ylamino)-quinazoline-8-carboxylic acid amide (26)

IC$_{50}$p70S6K [uM]: 0.022F (trans)-4-Benzyloxycarbonylamino-pyrrolidine-1,3-dicarboxylic acid 1-tert-butyl ester 3-ethyl ester 1-tert-Butyl 3-ethyl (trans)-4-aminopyrrolidine-1,3-dicarboxylate hydrochloride (500 mg; 1.70 mmol) and DIEA (886 µl; 5.09 mmol) were dissolved in DMF (17 ml). The solution was cooled to 0° C., benzyl chloroformate (358; 2.54 mmol) was added drop wise via syringe, and the reaction was stirred overnight at RT. The reaction was diluted with H$_2$O and extracted with EtOAc (3×10 mL). The organic extracts were dried, concentrated on SiO2, and purified via Biotage (10 g column) using 1% MeOH in DCM to provide the desired intermediate (600 mg, 43% yield. LC-MS: (M-Boc)+H=293, obsd.=293).

(trans)-4-Benzyloxycarbonylamino-pyrrolidine-1,3-dicarboxylic acid 1-tert-butyl ester)

(trans)-4-Benzyloxycarbonylamino-pyrrolidine-1,3-dicarboxylic acid 1-tert-butyl ester 3-ethyl ester (284 mg; 0.72 mmol) was dissolved in THF (5 ml) and then treated with LiOH (0.72 ml; 3.00 M; 2.17 mmol). The reaction was stirred at RT for 2 h. The reaction was diluted with H$_2$O and washed with EtOAc. The aqueous layer was acidified with solid KHSO$_4$ and extracted with EtOAc (3×). The organic extracts were washed with H$_2$O and brine, dried over Na$_2$SO$_4$, filtered and concentrated to provide the desired intermediate (quantitative yield) as a white solid. $^1$H NMR (in DMSO): 1.39 (s, 9H), 2.93 (m, 1H), 3.07 (m, 1H), 3.51-3.55 (m, 3H), 4.23 (m, 1H), 5.03 (s, 2H), 7.32-7.38 (m, 5H), 7.70 (m, 1H), 12.5 (s, 1H). LC-MS: (M-Boc)+H=265, obsd.=265.

(trans)-3-Benzyloxycarbonylamino-4-phenylcarbamoyl-pyrrolidine-1-carboxylic acid tert-butyl ester (trans)-4-Benzyloxycarbonylamino-pyrrolidine-1,3-dicarboxylic acid 1-tert-butyl ester (270 mg; 0.74 mmol) and 1-hydroxybenzotriazole (105 mg, 0.78 mmol) were dissolved into DMF (5 mL), and stirred for 5 minutes until solids dissolved entirely. Aniline (81 µl; 0.89 mmol) and 1-(3-dimethylaminopropyl)-3-ethylcarbodiimide hydrochloride (193 mg, 1.01 mmol) were added, and the yellow solution was stirred for 90 min. at 50° C. The reaction was quenched with H$_2$O (40 mL) and MeOH (5 mL). The resulting precipitate was filtered to provide the desired intermediate (293 mg, 90% yield). LC-MS: (M-Boc)+H=340, obsd.=340.
$^1$HNMR (in DMSO): 1.39 (s, 9H), 3.10 (m, 2H), 3.35 (m, 1H), 3.63-3.67 (m, 2H), 4.27 (m, 1H), 5.01-5.04 (m, 2H), 7.04-7.07 (t, 1H), 7.22-7.32 (m, 7H), 7.56-7.58 (d, 2H), 7.72 (d, 1H), 10.03 (s, 1H).

4-((trans)-1-tert-Butoxycarbonyl-4-phenylcarbamoyl-pyrrolidin-3-ylamino)-quinazoline-8-carboxylic acid methyl ester (trans)-3-Benzyloxycarbonylamino-4-phenylcarbamoyl-pyrrolidine-1-carboxylic acid tert-butyl ester (286 mg; 0.65 mmol) was dissolved in MeOH (15 ml). 10% Pd—C (143 mg) was added, and the reaction mixture was stirred at room temperature under H$_2$ atm (balloon) overnight. The reaction was filtered through celite, and concentrated. The crude material from above, methyl 4-chloroquinazoline-8-carboxylate (138 mg; 0.65 mmol), and DIEA (325; 1.87 mmol) were dissolved in THF (5 ml), and stirred at 60° C. for 4 days. The reaction mixture was concentrated and purified via prep HPLC to afford the desired intermediate (300 mg, 80% yield over 2 steps) as a white solid. LC-MS: M+H=492, obsd.=492. $^1$HNMR (in DMSO): 1.43 (s, 9H), 3.43-3.51 (m, 3H), 3.87-3.91 (m, 2H), 5.17 (d, 1H), 7.03-7.06 (t, 1H), 7.28-7.30 (t, 2H), 7.53-7.55 (d, 2H), 7.83 (t, 1H), 8.08 (s, 1H), 8.55-8.57 (d, 1H), 8.69 (d, 1H), 8.76 (s, 1H), 9.00-9.90 (s, 2H), 10.1 (s, 1H).

4-((trans)-4-Phenylcarbamoyl-pyrrolidin-3-ylamino)-quinazoline-8-carboxylic acid amide 4-((trans)-1-tert-Butoxycarbonyl-4-phenylcarbamoyl-pyrrolidin-3-ylamino)-quinazoline-8-carboxylic acid methyl ester (290 mg; 0.48 mmol) was dissolved in iPrOH (2 ml), DMSO (4 ml), and ammonium hydroxide (4 ml), and stirred overnight at 70° C. The reaction mixture was partially concentrated, diluted with H$_2$O, and extracted with EtOAc (3×). The organic extracts were washed with 1N NaOH and brine, dried over Na$_2$SO$_4$), filtered, and concentrated. The crude material was purified via prep HPLC. The purified material from above (153 mg; 0.26 mmol) was dissolved in dioxane (3 mL) and 4.0M HCl in dioxane (3 mL), and stirred for 90 min. at RT. The reaction mixture was concentrated and washed with MeOH (2×) to provide 26 (114 mg, 98% yield) as a white solid. LC-MS: M+H=377, obsd.=377. ¹HNMR (in DMSO): 3.39-3.87 (m, 5H), 5.21 (t, 1H), 7.05-7.08 (t, 1H), 7.29-7.32 (t, 2H), 7.58-7.63 (d, 2H), 7.84 (t, 1H), 8.10 (s, 1H), 8.58 (d, 1H), 8.77 (s, 1H), 9.07 (s, 1H), 9.54 (s, 1H), 9.66 (s, 1H), 10.6 (s, 1H).

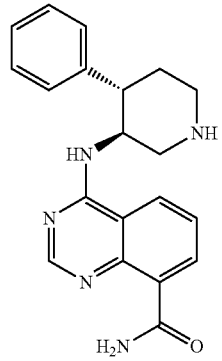 [SMILES: NC(=O)c1cccc2c(N[C@@H]3CNCC[C@H]3c3ccccc3)ncnc12]

trans, racemic 4-((4-phenylpiperidin-3-yl)amino)quinazoline-8-carboxamide (27)

IC$_{50}$p70S6K [uM]: 0.0063 tert-Butyl 3-((8-carbamoylquinazolin-4-yl)amino)-4-phenylpiperidine-1-carboxylate Methyl 4-chloroquinazoline-8-carboxylate (750 mg; 3.37 mmol), DIEA (1.21 ml; 6.74 mmol), and trans, racemic tert-butyl 3-amino-4-phenylpiperidine-1-carboxylate (959.00 mg; 3.47 mmol) were dissolved in CH$_3$CN (5 mL), and stirred at 45° C. for 72 h. The reaction mixture was concentrated.

The crude residue from above was dissolved in methanolic ammonia (4.8 ml; 7.00 M; 33.69 mmol) and stirred overnight at 60 C. The reaction mixture was concentrated, redissolved in HCl in MeOH (5.00 ml; 4.00 M; 20.00 mmol), and stirred overnight at RT. The reaction mixture was filtered, and the precipitate was washed with MeOH and ether to provide 27 (1000 mg, 81% yield). LC-MS (M+H=421, obsd=348). ¹HNMR (DMSC-d6) δ 1.69-1.70 (m, 1H), 1.79 (d, 1H), 2.50-2.51 (m, 1H), 3.00-3.03 (m, 2H), 3.18 (d, 1H), 4.62-4.66 (m, 1H). 7.05 (t, 1H), 7.16 (t, 2H), 7.29 9t, 2H), 7.54 (t, 1H), 7.78 (d, 1H), 8.15 (d, 1H), 8.30 (d, 1H), 8.47-8.49 9d, 2H).

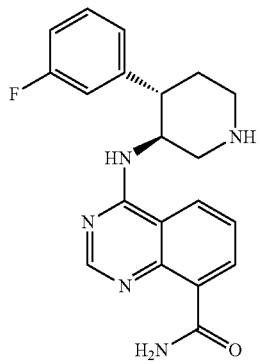

racemic, trans 4-((4-(3-fluorophenyl)piperidin-3-yl)amino)quinazoline-8-carboxamide (28)

IC$_{50}$p70S6K [uM]: 0.0018

The compound was synthesized according to the procedure described for the preparation of example 27 using racemic, trans tert-butyl 3-amino-4-(3-fluorophenyl)piperidine-1-carboxylate and methyl 4-chloroquinazoline-8-carboxylate. LC-MS (M+H=366, obsd=366).

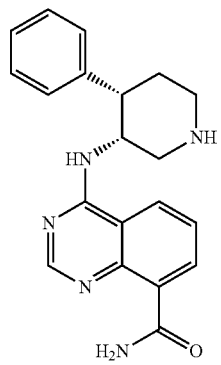 [SMILES: NC(=O)c1cccc2c(N[C@H]3CNCC[C@H]3c3ccccc3)ncnc12]

cis, racemic 4-((4-phenylpiperidin-3-yl)amino)quinazoline-8-carboxamide (29)

The compound was synthesized according to the procedure described for the preparation of example 27 using cis, racemic tert-butyl 3-amino-4-phenylpiperidine-1-carboxylate and methyl 4-chloroquinazoline-8-carboxylate. LC-MS (M+H=348, obsd=348). ¹HNMR (DMSC-d6) δ 1.98-2.20 (d, 1H), 2.60-2.70 (m, 1H), 3.50-3.56 (m, 4H), 5.34 (d, 1H), 6.91 (t, 1H), 7.14-7.21 (m, 3H), 7.76 (t, 1H), 7.98 (s, 1H), 8.52-8.55 (m, 3H), 8.72 (d, 1H), 9.16 9d, 1H).

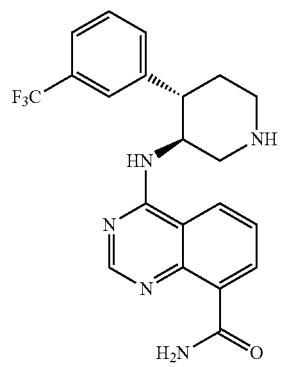 [SMILES: NC(=O)c1cccc2c(N[C@@H]3CNCC[C@H]3c3cccc(C(F)(F)F)c3)ncnc12]

trans, racemic 4-((4-(3-(trifluoromethyl)phenyl)piperidin-3-yl)amino)quinazoline-8-carboxamide (30)

IC$_{50}$p70S6K [uM]: 0.0021

The compound was synthesized according to the procedure described for the preparation of example 27 using trans, racemic tert-butyl 3-amino-4-(3-(trifluoromethyl)phenyl)piperidine-1-carboxylate and methyl 4-chloroquinazoline-8-carboxylate. LC-MS (M+H=416, obsd=416).

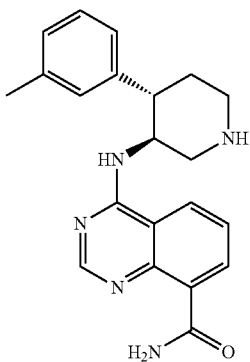 [SMILES: Cc1cccc([C@@H]2CCNC[C@H]2Nc2ncnc3c(C(N)=O)cccc23)c1]

trans, racemic 4-((4-(m-tolyl)piperidin-3-yl)amino)quinazoline-8-carboxamide (31)

IC$_{50}$p70S6K [uM]: 0.0031

The compound was synthesized according to the procedure described for the preparation of example 27 using trans, racemic tert-butyl 3-amino-4-(m-tolyl)piperidine-1-carboxylate and methyl 4-chloroquinazoline-8-carboxylate. LC-MS (M+H=362, obsd=362).

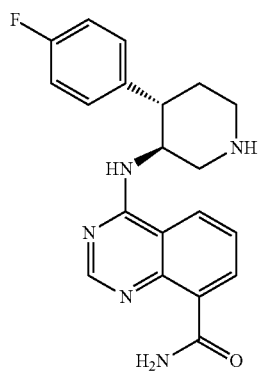 [SMILES: NC(=O)c1cccc2c(N[C@@H]3CNCC[C@H]3c3ccc(F)cc3)ncnc12]

trans, racemic 4-((4-(4-fluorophenyl)piperidin-3-yl)amino)quinazoline-8-carboxamide (32)

IC$_{50}$p70S6K [uM]: 0.0032

The compound was synthesized according to the procedure described for the preparation of example 27 using trans, racemic tert-butyl 3-amino-4-(4-fluorophenyl)piperidine-1-carboxylate and methyl 4-chloroquinazoline-8-carboxylate. LC-MS (M+H=366, obsd=366).

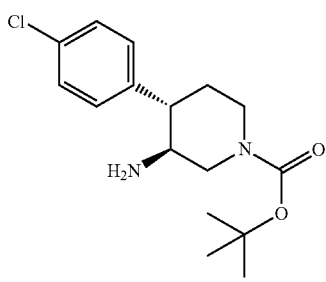 [SMILES: CC(C)(C)OC(=O)N1CC[C@@H](c2ccc(Cl)cc2)[C@H](N)C1]

trans, racemic tert-butyl 3-amino-4-(4-chlorophenyl)piperidine-1-carboxylate (33)

Methyl 1-methyl-1,2,5,6-tetrahydropyridine-3-carboxylate

K$_2$CO$_3$ (50 g; 361.78 mmol) was added to a solution of methyl 1-methyl-1,2,5,6-tetrahydropyridine-3-carboxylate hydrobromide (50 g; 211.77 mmol) in H$_2$O (50 ml) and DCM (250 ml), and stirred at RT for 30 mins. The organic layer was separated, washed with brine, dried over MgSO$_4$, filtered and concentrated to provide the desired intermediate (34 g, quantitative yield).

Methyl 4-(4-chlorophenyl)-1-methylpiperidine-3-carboxylate

Bromo(4-chlorophenyl)magnesium (47 ml; 1.00 M; 47.27 mmol) was added to a solution of methyl 1-methyl-1,2,5,6-tetrahydropyridine-3-carboxylate (5.24 g; 33.76 mmol) in ether (150 ml) at −10° C. over 45 min. The reaction mixture was stirred for 20 min, and then quenched with satd. NH$_4$Cl. The organic layer was washed with brine, dried over MgSO$_4$, filtered, and concentrated. The crude product was purified via Biotage eluting with a gradient of 20 to 60% EtOAc in hexane with 4% TEA to provide the desired intermediate as a mixture of cis and trans isomers (2.8 g).

trans, racemic Methyl 4-(4-chlorophenyl)-1-methylpiperidine-3-carboxylate

Sodium methoxide (4.3 g; 19.83 mmol) was added to a solution of methyl 4-(4-chlorophenyl)-1-methylpiperidine-3-carboxylate (5.3 g; 19.83 mmol) in MeOH (100 ml), and stirred at 60° C. for 6 h. The reaction mixture was concentrated, the residue was diluted with EtOAC (100 ml), washed with satd. NH$_4$Cl and brine, dried over MgSO$_4$, filtered, and concentrated to provide the desired trans intermediate (4.9 g, 92% yield). $^1$HNMR (DMSO-d6) δ 1.91 (m, 1H), 2.20-2.22 (m, 1H), 2.78 (s, 3H) 2.99-3.01 (m, 1H0, 3.06-3.25 (m, 2H), 3.31-3.52 (m, 2H), 3.36 (s, 1H), 7.22 (d, 2H), 7.43 (d, 2H).

trans, racemic 1-tert-Butyl 3-methyl 4-(4-chlorophenyl)piperidine-1,3-dicarboxylate Cs$_2$CO$_3$ (1.19 g; 3.65 mmol) was added to a solution of trans, racemic methyl 4-(4-chlorophenyl)-1-methylpiperidine-3-carboxylate (4.89 g; 18.26 mmol) in DCE (100 ml). 1-chloroethyl chloridocarbonate (2.99 ml; 27.39 mmol) was added drop wise, and the reaction mixture was stirred at 80° C. for 1 h. The reaction was concentrated, the residue was redissolved in MeOH (100 ml), and stirred at 60° C. for 2 h. The reaction mixture was concentrated, and the residue was redissolved in DCM (100 ml). DIEA (9.84 ml; 54.79 mmol) and di-tert-butyl dicarbonate (4.78 g; 21.92 mmol) were added, and the reaction mixture was stirred overnight at RT. The reaction solution was washed with brine, dried over Na$_2$SO$_4$, filtered, and concentrated. The crude material was purified via Biotage eluting with a gradient of 10 to 25% EtOAc in hexane to provide the desired intermediate (4.8 g, 74% yield). LC-MS (M+H=354, obsd=354).

trans, racemic 1-(tert-butoxycarbonyl)-4-(4-chlorophenyl)piperidine-3-carboxylic acid 1-tert-Butyl 3-methyl 4-(4-chlorophenyl)piperidine-1,3-dicarboxylate (4.80 g; 13.57 mmol) and LiOH (0.97 g; 40.70 mmol) were dissolved in THF (20 ml) and H₂O (20 ml), and stirred overnight at 40° C. Acetic acid was added to adjust the pH to 5. The product was extracted with DCM, washed with brine, dried over MgSO₄, filtered and concentrated to provide the desired intermediate (3.66 g, 79% yield). MS [240, fragmentation, M+1 minus C(O)—O-t-Bu].

trans, racemic tert-butyl 3-amino-4-(4-chlorophenyl)piperidine-1-carboxylate 1-(tert-Butoxycarbonyl)-4-(4-chlorophenyl)piperidine-3-carboxylic acid (1.4 g; 4.12 mmol), diphenyl azidophosphate (1.10 ml; 4.94 mmol), and TEA (1.74 ml; 12.36 mmol) were dissolved in DCE (5 ml), and stirred at RT for 3 h. The reaction mixture was diluted with toluene, washed with brine, dried over MgSO₄, filtered, and concentrated. The residue was redissolved in toluene (10 ml), and heated at reflux for 5 h. The reaction mixture was cooled to room temperature, H₂O (445 mg; 24.72 mmol) was added, and the reaction was reheated at reflux for 12 h. The reaction mixture was concentrated, and the crude material was purified by Biotage eluting with a gradient of 20 to 60% EtOAc in hexane to provide 33 (577 mg). LC-MS (M+H=311, obsd=255 and small 311).

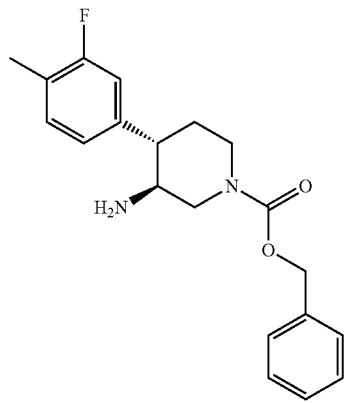 [SMILES: Cc1ccc([C@@H]2CCN(C(=O)OCc3ccccc3)C[C@H]2N)cc1F]

racemic, trans Benzyl 3-amino-4-(3-fluoro-4-methylphenyl)piperidine-1-carboxylate (34)

Methyl 4-(3-fluoro-4-methylphenyl)-1-methylpiperidine-3-carboxylate

A solution of 4-Bromo-2-fluoro-1-methylbenzene (3.70 g; 20 mmol) in ether (25 mL) was added drop wise to a suspension of Mg (0.49 g; 20.75 mmol) in ether (20 ml) over 20 min to maintain gentle reflux, and the reaction mixture was stirred at RT for 2 h. The reaction mixture was cooled to −10° C., and a solution of methyl 1-methyl-1,2,5,6-tetrahydropyridine-3-carboxylate (1.90 g; 10 mmol) in ether (20 ml) was added drop wise over 15 min, and the reaction mixture was stirred for 1 h. The reaction mixture was quenched with satd. aqueous NH₄Cl (35 ml), and diluted with EtOAc (50 mL. The organic layer was isolated, washed NH₄Cl and brine, dried over Na₂SO₄, filtered, and concentrated. The crude material was purified by the Biotage eluting with a gradient of 30 to 50% EtOAc in hexane with 4% TEA to provide the desired product (2.0 g, 62% yield) as a mixture of cis and trans isomers. LC-MS (M+H=311, obsd=266).

trans, racemic methyl 4-(3-fluoro-4-methylphenyl)-1-methylpiperidine-3-carboxylate NaOMe (1.6 g; 7.54 mmol) was added to a solution of methyl 4-(3-fluoro-4-methylphenyl)-1-methylpiperidine-3-carboxylate (2.0 g; 7.54 mmol) in MeOH (30 ml), and stirred for 4 h at 60° C. The reaction mixture was concentrated to provide the desired intermediate (1.64 g, 82% yield).

trans, racemic 1-Benzyl 3-methyl 4-(3-fluoro-4-methylphenyl)piperidine-1,3-dicarboxylate Cs₂CO₃ (0.40 g; 1.23 mmol) was added to a solution of trans, racemic methyl 4-(3-fluoro-4-methylphenyl)-1-methylpiperidine-3-carboxylate (1.64 g, 6.17 mmol) in DCE (100 ml). 1-chloroethyl chloridocarbonate (0.71 ml; 6.48 mmol) was added drop wise, and the reaction mixture was stirred at 80° C. for 1 h. The reaction mixture was concentrated, redissolved in MeOH (100 ml), and stirred overnight at 60° C. The reaction mixture was concentrated, the residue was dissolved in DCM (100 ml), DIEA (2.22 ml; 12.34 mmol) and 1-{[(benzyloxy)carbonyl]oxy}pyrrolidine-2,5-dione (1.61 g; 6.48 mmol) were added, and the reaction mixture was stirred at RT for 3 h. The reaction solution was washed with brine, dried over Na₂SO₄, filtered, and concentrated. The crude material was purified via Biotage eluting with 20% EtOAc in hexane) to provide the desired intermediate (1.2 g, 50% yield, two steps). LC-MS (M+H=386, obsd=386).

trans, racemic, 1-((Benzyloxy)carbonyl)-4-(3-fluoro-4-methylphenyl)piperidine-3-carboxylic acid 1-Benzyl 3-methyl 4-(3-fluoro-4-methylphenyl)piperidine-1,3-dicarboxylate (1.20 g; 3.11 mmol) and LiOH (0.22 g; 9.34 mmol) were dissolved in H₂O (5 ml) and THF (5 ml), and stirred overnight at 40° C. Acetic acid was added to adjust the pH to 5. The product was extracted with DCM (50 ml×2), The combined organic extracts were dried over Na₂SO₄, filtered, and concentrated. The crude material was purified via Biotage eluting with 20 to 50% EtOAc in hexane) to provide the desired intermediate (0.8 g, 70% yield). LC-MS (M+H=372, obsd=372).

trans, racemic Benzyl 3-amino-4-(3-fluoro-4-methylphenyl)piperidine-1-carboxylate 1-[(Benzyloxy)carbonyl]-4-(3-fluoro-4-methylphenyl)piperidine-3-carboxylic acid (457.00 mg; 1.23 mmol) and TEA (0.52 ml; 3.69 mmol) were dissolved in DCE (5 ml). Diphenyl azidophosphate (0.33 ml; 1.48 mmol) was added, and the reaction solution was stirred at RT for 3 h. The reaction solution was diluted with toluene, washed with NaHCO₃ and brine, dried over MgSO₄, filtered, and concentrated. The residue was redissolved in toluene (5 ml), and stirred at 110° C. for 4 h. 2-methylpropan-2-ol (0.33 ml; 3.69 mmol) was added, and the solution was stirred overnight. The reaction mixture was concentrated, the residue was redissolved in MeOH (3 ml), HCl in dioxane (3.00 ml; 4.00 M; 12.00 mmol) was added, and the reaction mixture was stirred for 2 h at RT. The reaction mixture was concentrated, triturated with ether, and filtered to provide 34 (240 mg, 47% yield). LC-MS (M+H=415, obsd=343). ¹HNMR (DMSC-d6) δ 1.68-1.73 (m, 1H), 2.21 (s, 1H), 2.84-2.88 (m, 3H), 3.35-3.39 (m, 1H0<3.56 (3.63 (m, 2H), 4.07 (d, 1H), 4.48 (d, 1H), 5.11 (s, 2H), 7.09 (d, 1H), 7.18-7.26 (m, 2H). 7.39-7.41 (m, 5H), 7.98 (s, 2H).

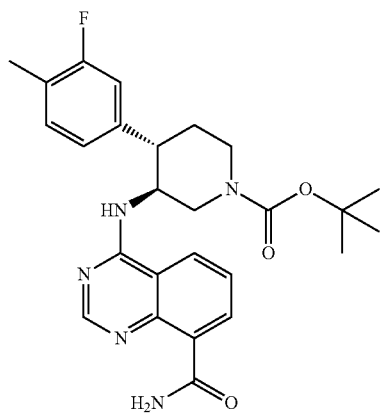 [SMILES: Cc1ccc([C@@H]2CCN(C(=O)OC(C)(C)C)C[C@H]2Nc2ncnc3c(C(N)=O)cccc23)cc1F]

trans, racemic Benzyl 3-((8-carbamoylquinazolin-4-yl)amino)-4-(3-fluoro-4-methylphenyl)piperidine-1-carboxylate (35)

$IC_{50}$p70S6K [nM]: 1000

Methyl 4-chloroquinazoline-8-carboxylate (120 mg; 0.54 mmol), DIEA (0.39 ml; 2.16 mmol), and trans, racemic benzyl 3-amino-4-(3-fluoro-4-methylphenyl)piperidine-1-carboxylate dihydrochloride (230 mg; 0.56 mmol) were dissolved in $CH_3CN$, and stirred at 40° C. 72 h. The reaction mixture was concentrated, redissolved in methanolic ammonia (0.77 ml; 7.00 M; 5.39 mmol), and stirred overnight at 45° C. The reaction mixture was concentrated, and the crude product was purified via prep HPLC to provide 35 (150 mg, 54% yield). LC-MS (M+H=514, obsd=514).

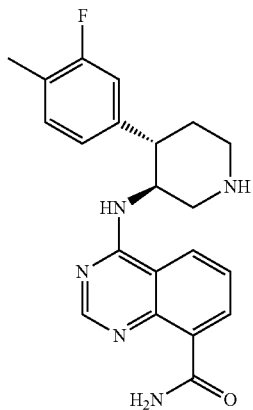 [SMILES: Cc1ccc([C@@H]2CCNC[C@H]2Nc2ncnc3c(C(N)=O)cccc23)cc1F]

racemic, trans 4-((4-(3-fluoro-4-methylphenyl)piperidin-3-yl)amino)quinazoline-8-carboxamide (36)

Benzyl 3-{[8-(aminocarbonyl)quinazolin-4-yl]amino}-4-(3-fluoro-4-methylphenyl)piperidine-1-carboxylate (23 mg; 0.04 mmol) was dissolved in EtOH (1.5 ml). Formic acid ammoniate (28 mg; 0.45 mmol) and $Pd(OH)_2$ (30 mg; 0.02 mmol; 50% wet) were added, and the reaction mixture was stirred at 60° C. for 20 min. The crude product was purified directly via prep HPLC to provide 36. LC-MS (M+H=380, obsd=380). $^1$HNMR (DMSO-d6) δ 2.09 (s, 3H), 2.21 (m, 1H), 3.13-3.24 (m, 2H), 3.52-3.59 (d, 1H), 3.72-2.77 (d, 1H), 4.86-4.90 (m, 2H), 5.20-5.25 (m, 1H), 7.01-7.07 (m, 3H), 7.68 (t, 1H), 8.26-8.29 (d, 1H), 8.54-8.56 (d, 1H), 8.65 (s, 1H).

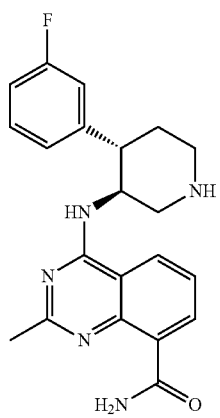 [SMILES: Cc1nc(N[C@@H]2CNCC[C@H]2c2cccc(F)c2)c2cccc(C(N)=O)c2n1]

trans, racemic 4-((4-(3-fluorophenyl)piperidin-3-yl)amino)-2-methylquinazoline-8-carboxamide (37)

$IC_{50}$p70S6K [nM]: 2.5

The compound was synthesized according to the procedure described for the preparation of example 27 using trans, racemic tert-butyl 3-amino-4-(3-fluorophenyl)piperidine-1-carboxylate and 4-chloro-2-methylquinazoline-8-carboxamide. LC-MS (M+H=380, obsd=380).

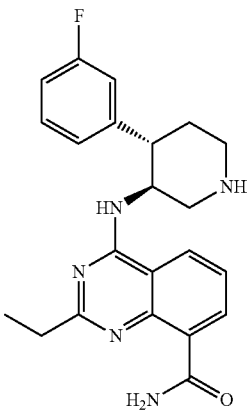 [SMILES: CCc1nc(N[C@@H]2CNCC[C@H]2c2cccc(F)c2)c2cccc(C(N)=O)c2n1]

trans, racemic 2-ethyl-4-((4-(3-fluorophenyl)piperidin-3-yl)amino)quinazoline-8-carboxamide (38)

$IC_{50}$p70S6K [uM]: 0.0017

The compound was synthesized according to the procedure described for the preparation of example 27 using trans, racemic tert-butyl 3-amino-4-(3-fluorophenyl)piperidine-1-carboxylate and 4-chloro-2-ethylquinazoline-8-carboxamide. LC-MS (M+H=394, obsd=394).

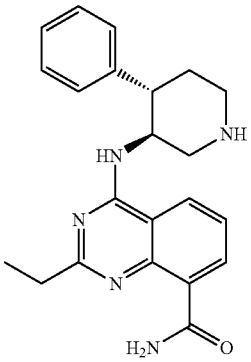 [SMILES: CCc1nc(N[C@@H]2CNCC[C@H]2c2ccccc2)c2cccc(C(N)=O)c2n1]

trans, racemic 2-ethyl-4-((4-phenylpiperidin-3-yl)
amino)quinazoline-8-carboxamide (39)

IC$_{50}$p70S6K [uM]: 0.0048

The compound was synthesized according to the procedure described for the preparation of example 27 using trans, racemic tert-butyl 3-amino-4-phenylpiperidine-1-carboxylate and 4-chloro-2-ethylquinazoline-8-carboxamide. LC-MS (M+H=376, obsd=376).

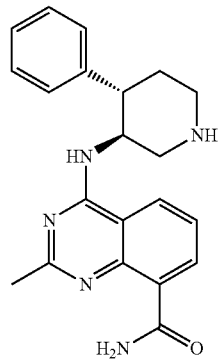 [SMILES: Cc1nc(N[C@@H]2CNCC[C@H]2c2ccccc2)c2cccc(C(N)=O)c2n1]

trans, racemic 2-methyl-4-((4-phenylpiperidin-3-yl)
amino)quinazoline-8-carboxamide (40)

IC$_{50}$p70S6K [uM]: 0.0064

The compound was synthesized according to the procedure described for the preparation of example 27 using trans, racemic tert-butyl 3-amino-4-phenylpiperidine-1-carboxylate and 4-chloro-2-methylquinazoline-8-carboxamide.
LC-MS (M+H=362, obsd=362).

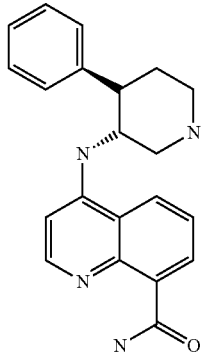

trans, racemic 4-((4-phenylpiperidin-3-yl)amino)
quinoline-8-carboxamide (41)

The compound was synthesized according to the procedure described for the preparation of example 19 using trans, racemic tert-butyl 3-amino-4-phenylpiperidine-1-carboxylate and ethyl 4-chloro-8-cyanoquinoline-3-carboxylate.
LC-MS (M+H=347, obsd=347).

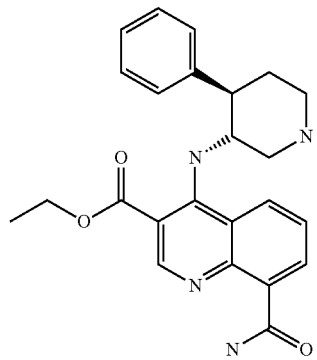

trans, racemic Ethyl 8-carbamoyl-4-(4-phenylpiperidin-3-yl)amino)quinoline-3-carboxylate (42)

The compound was synthesized according to the procedure described for the preparation of example 19 using trans, racemic tert-butyl 3-amino-4-phenylpiperidine-1-carboxylate and 4-chloro-8-cyanoquinoline-3-ethyl ester.
LC-MS (M+H=419, obsd=419).

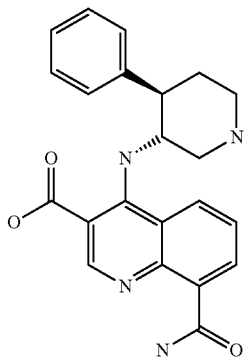

trans, racemic 8-carbamoyl-4-((4-phenylpiperidin-3-yl)amino)quinoline-3-carboxylic acid (43)

The compound was synthesized according to the procedure described for the preparation of example 19 using trans, racemic tert-butyl 3-amino-4-phenylpiperidine-1-carboxylate and 4-chloro-8-cyanoquinoline-3-carboxylic acid. LC-MS (M+H=391, obsd=391).

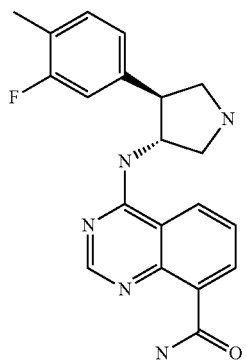 [SMILES: Cc1ccc([C@H]2CNC[C@@H]2Nc2ncnc3c(C(N)=O)cccc23)cc1F]

trans, racemic 4-(3-fluoro-4-methylphenyl)pyrrolidin-3-yl)amino)quinazoline-8-carboxamide (44)

The compound was synthesized according to the procedure described for the preparation of example 2 using tert-butyl 3-amino-4-(3-fluoro-4-methylphenyl)pyrrolidine-1-carboxylate (racemic-trans) and methyl 4-chloroquinazoline-8-carboxylate. LC-MS (M+1=365, obsd=365).

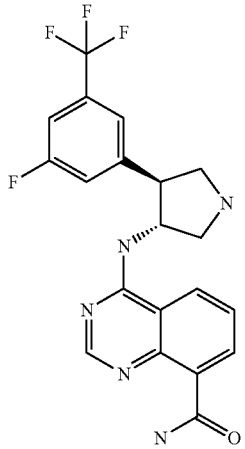

trans, racemic 4-(3-fluoro-5-(trifluoromethyl)phenyl)pyrrolidin-3-yl)amino)quinazoline-8-carboxamide (45)

$IC_{50}$p70S6K [nM]: 1.9

The compound was synthesized according to the procedure described for the preparation of example 2 using tert-butyl 3-amino-4-(3-fluoro-5-(trifluoromethyl)phenyl)pyrrolidine-1-carboxylate (racemic-trans) and methyl 4-chloroquinazoline-8-carboxylate. LC-MS (M+1=419, obsd=419).

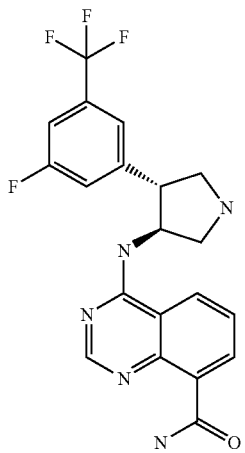

4-(((3S,4R)-4-(3-fluoro-5-(trifluoromethyl)phenyl)pyrrolidin-3-yl)amino)quinazoline-8-carboxamide (46)

$IC_{50}$p70S6K [nM]: 2.6

The compound was isolated by chiral chromatography from 4-(3-fluoro-5-(trifluoromethyl)phenyl)pyrrolidin-3-yl)amino)quinazoline-8-carboxamide. (trans_racemic). LC-MS (M+1=419, obsd=419).

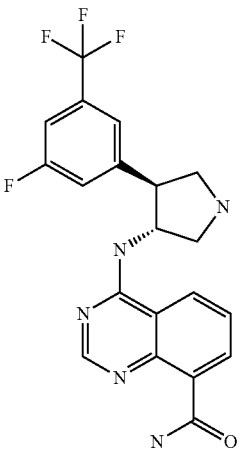 [SMILES: NC(=O)c1cccc2c(N[C@H]3CNC[C@@H]3c3cc(F)cc(C(F)(F)F)c3)ncnc12]

4-(((3R,4S)-4-(3-fluoro-5-(trifluoromethyl)phenyl)pyrrolidin-3-yl)amino)quinazoline-8-carboxamide (47)

$IC_{50}$p70S6K [nM]: 160

The compound was isolated by chiral chromatography from 4-(3-fluoro-5-(trifluoromethyl)phenyl)pyrrolidin-3-yl)amino)quinazoline-8-carboxamide. (trans_racemic). LC-MS (M+1=419, obsd=419).

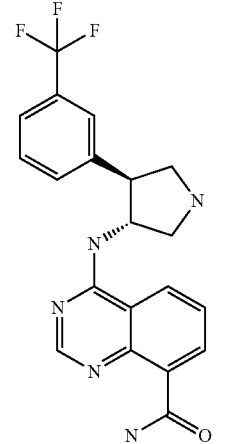 [SMILES: NC(=O)c1cccc2c(N[C@H]3CNC[C@@H]3c3cccc(C(F)(F)F)c3)ncnc12]

trans, racemic 4-(3-(trifluoromethyl)phenyl)pyrrolidin-3-yl)amino)quinazoline-8-carboxamide (48)

$IC_{50}$p70S6K [nM]: 1.7

The compound was synthesized according to the procedure described for the preparation of example 2 using tert-butyl 3-amino-4-(3-(trifluoromethyl)phenyl)pyrrolidine-1-carboxylate (racemic-trans) and methyl 4-chloroquinazoline-8-carboxylate. LC-MS (M+1=402, obsd=402).

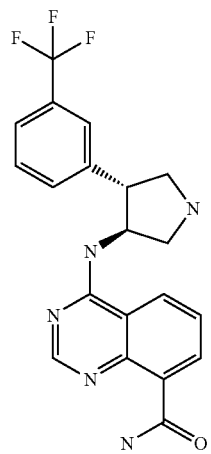 [SMILES: NC(=O)c1cccc2c(N[C@@H]3CNC[C@H]3c3cccc(C(F)(F)F)c3)ncnc12]

4-(((3S,4R)-4-(3-(trifluoromethyl)phenyl)pyrrolidin-3-yl)amino)quinazoline-8-carboxamide (49)

$IC_{50}$ p70S6K [nM]: 60

The compound was isolated by chiral chromatography from 4-(3-(trifluoromethyl)phenyl)pyrrolidin-3-yl)amino)quinazoline-8-carboxamide (trans_racemic) LC-MS (M+1=402, obsd=402).

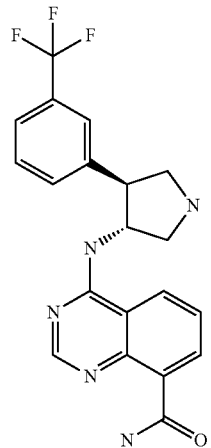 [SMILES: NC(=O)c1cccc2c(N[C@H]3CNC[C@@H]3c3cccc(C(F)(F)F)c3)ncnc12]

4-(((3R,4S)-4-(3-(trifluoromethyl)phenyl)pyrrolidin-3-yl)amino)quinazoline-8-carboxamide (50)

$IC_{50}$ p70S6K [nM]: 3

The compound was isolated by chiral chromatography 4-(3-(trifluoromethyl)phenyl)pyrrolidin-3-yl)amino)quinazoline-8-carboxamide (trans_racemic). LC-MS (M+1=402, obsd=402).

cis, racemic 4-(3-(trifluoromethyl)phenyl)pyrrolidin-3-yl)amino)quinazoline-8-carboxamide (51)

The compound was synthesized according to the procedure described for the preparation of example 2 using tert-butyl 3-amino-4-(3-(trifluoromethyl)phenyl)pyrrolidine-1-carboxylate (Cis_racemic) and methyl 4-chloroquinazoline-8-carboxylate. LC-MS (M+1=402, obsd=402).

trans, racemic 4-(4-(trifluoromethyl)phenyl)pyrrolidin-3-yl)amino)quinazoline-8-carboxamide. (52)

$IC_{50}$ p70S6K [nM]: 6.5

The compound was synthesized according to the procedure described for the preparation of example 2 using tert-butyl 3-amino-4-(4-(trifluoromethyl)phenyl)pyrrolidine-1-carboxylate (racemic-trans) and methyl 4-chloroquinazoline-8-carboxylate. LC-MS (M+1=402, obsd=402).

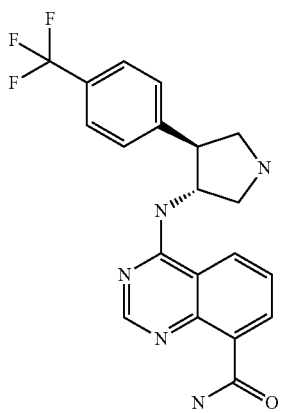 [SMILES: NC(=O)c1cccc2c(N[C@H]3CNC[C@@H]3c3ccc(C(F)(F)F)cc3)ncnc12]

4-(((3R,4S)-4-(4-(trifluoromethyl)phenyl)pyrrolidin-3-yl)amino)quinazoline-8-carboxamide (53)

IC$_{50}$p70S6K [nM]: 66

The compound was isolated by chiral chromatography from 4-(4-(trifluoromethyl)phenyl)pyrrolidin-3-yl)amino)quinazoline-8-carboxamide (trans_racemic). LC-MS (M+1=402, obsd=402).

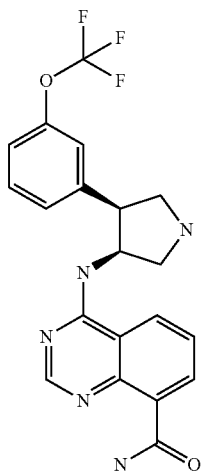 [SMILES: NC(=O)c1cccc2c(N[C@@H]3CNC[C@@H]3c3cccc(OC(F)(F)F)c3)ncnc12]

cis, racemic 4-(3-(trifluoromethoxy)phenyl)pyrrolidin-3-yl)amino)quinazoline-8-carboxamide (55)

IC$_{50}$p70S6K [nM]: 9.0

The compound was synthesized according to the procedure described for the preparation of example 2 using tert-butyl 3-amino-4-(3-(trifluoromethoxy)phenyl)pyrrolidine-1-carboxylate (cis-trans) and methyl 4-chloroquinazoline-8-carboxylate. LC-MS (M+1=418, obsd=418).

4-(((3R,4R)-4-(4-(trifluoromethyl)phenyl)pyrrolidin-3-yl)amino)quinazoline-8-carboxamide (54)

IC$_{50}$p70S6K [nM]: 1.3

The compound was isolated by chiral chromatography from 4-(4-(trifluoromethyl)phenyl)pyrrolidin-3-yl)amino) quinazoline-8-carboxamide. (trans_racemic). LC-MS (M+1=402, obsd=402).

trans, racemic 4-(3-(trifluoromethoxy)phenyl)pyrrolidin-3-yl)amino)quinazoline-8-carboxamide (56)

The IC$_{50}$p70S6K [nM]: 2.4

The compound was synthesized according to the procedure described for the preparation of example 2 using tert-butyl 3-amino-4-(3-(trifluoromethoxy)phenyl)pyrrolidine-1-carboxylate (racemic-trans) and methyl 4-chloroquinazoline-8-carboxylate. LC-MS (M+1=418, obsd=418).

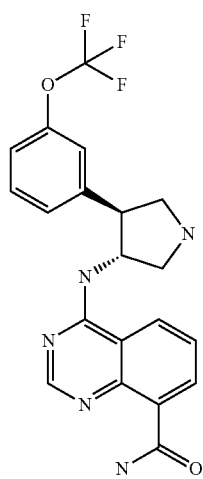 [SMILES: NC(=O)c1cccc2c(N[C@H]3CNC[C@@H]3c3cccc(OC(F)(F)F)c3)ncnc12]

4-(((3R,4S)-4-(3-(trifluoromethoxy)phenyl)pyrrolidin-3-yl)amino)quinazoline-8-carboxamide) (57)

IC$_{50}$p70S6K [nM]: 2.1

The compound was isolated by chiral chromatography from 4-(3-(trifluoromethoxy)phenyl)pyrrolidin-3-yl)amino) quinazoline-8-carboxamide. (trans_racemic). LC-MS (M+1=418, obsd=418).

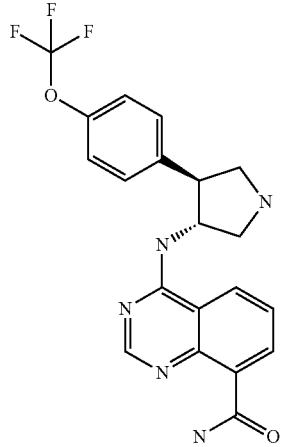

trans, racemic 4-(4-(trifluoromethoxy)phenyl)pyrrolidin-3-yl)amino)quinazoline-8-carboxamide (59)

IC$_{50}$p70S6K [nM]: 1.7

The compound was synthesized according to the procedure described for the preparation of example 2 using tert-butyl 3-amino-4-(4-(trifluoromethoxy)phenyl)pyrrolidine-1-carboxylate (racemic-trans) and methyl 4-chloroquinazoline-8-carboxylate. LC-MS (M+1=418, obsd=418).

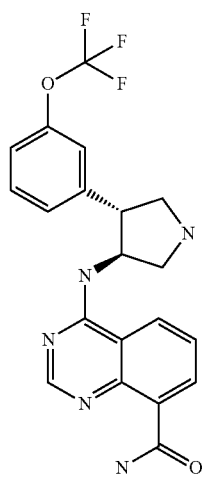 [SMILES: NC(=O)c1cccc2c(N[C@@H]3CNC[C@H]3c3cccc(OC(F)(F)F)c3)ncnc12]

4-(((3R,4R)-4-(3-(trifluoromethoxy)phenyl)pyrrolidin-3-yl)amino)quinazoline-8-carboxamide (58)

IC$_{50}$p70S6K [nM]: 0.98

The compound was isolated by chiral chromatography from 4-(3-(trifluoromethoxy)phenyl)pyrrolidin-3-yl)amino) quinazoline-8-carboxamide (trans_racemic) LC-MS (M+1=418, obsd=418).

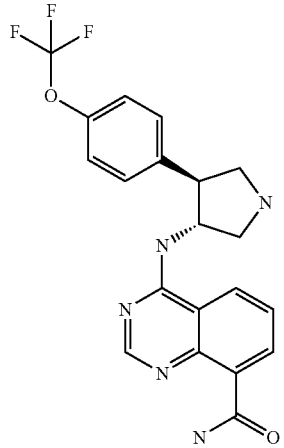 [SMILES: NC(=O)c1cccc2c(N[C@H]3CNC[C@@H]3c3ccc(OC(F)(F)F)cc3)ncnc12]

4-(((3R,4S)-4-(4-(trifluoromethoxy)phenyl)pyrrolidin-3-yl)amino)quinazoline-8-carboxamide (60)

IC$_{50}$p70S6K [nM]: 120

The compound was isolated by chiral chromatography from 4-(4-(trifluoromethoxy)phenyl)pyrrolidin-3-yl)amino) quinazoline-8-carboxamide. (trans_racemic). LC-MS (M+1=418, obsd=418).

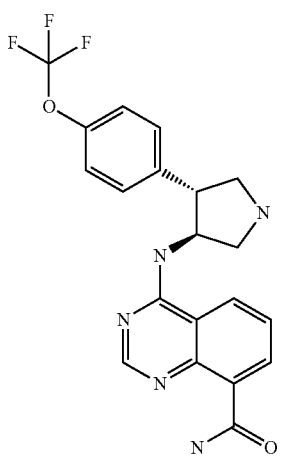 [SMILES: NC(=O)c1cccc2c(N[C@@H]3CNC[C@H]3c3ccc(OC(F)(F)F)cc3)ncnc12]

4-(((3S,4R)-4-(4-(trifluoromethoxy)phenyl)pyrrolidin-3-yl)amino)quinazoline-8-carboxamide (61)

IC$_{50}$p70S6K [nM]: 1.5

The compound was isolated by chiral chromatography from 4-(4-(trifluoromethoxy)phenyl)pyrrolidin-3-yl)amino)quinazoline-8-carboxamide. (trans_racemic). LC-MS (M+1=418, obsd=418).

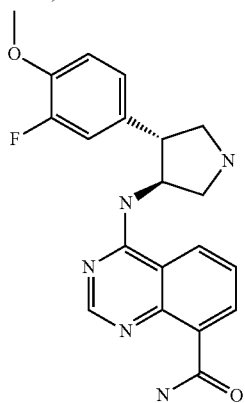

4-(((3S,4R)-4-(3-fluoro-4-methoxyphenyl)pyrrolidin-3-yl)amino)quinazoline-8-carboxamide (62)

IC$_{50}$p70S6K [nM]: 1.5

The compound was isolated by chiral chromatography from 4-(3-fluoro-4-methoxyphenyl)pyrrolidin-3-yl)amino) quinazoline-8-carboxamide. (trans_racemic). LC-MS (M+1=382, obsd=382)

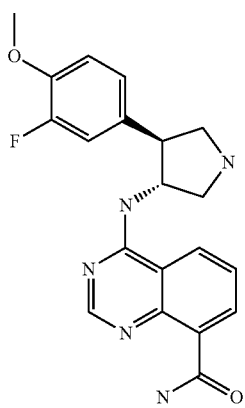 [SMILES: COc1ccc([C@H]2CNC[C@@H]2Nc2ncnc3c(C(N)=O)cccc23)cc1F]

4-(((3R,4S)-4-(3-fluoro-4-methoxyphenyl)pyrrolidin-3-yl)amino)quinazoline-8-carboxamide (63)

IC$_{50}$p70S6K [nM]: 810

The compound was isolated by chiral chromatography from 4-(3-fluoro-4-methoxyphenyl)pyrrolidin-3-yl)amino) quinazoline-8-carboxamide. (trans_racemic). LC-MS (M+1=382, obsd=382).

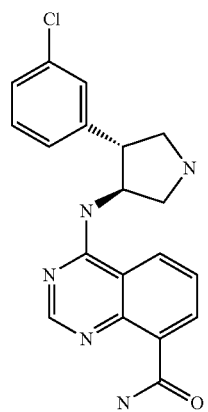 [SMILES: NC(=O)c1cccc2c(N[C@@H]3CNC[C@H]3c3cccc(Cl)c3)ncnc12]

4-(((3R,4S)-4-(3-chlorophenyl)pyrrolidin-3-yl) amino)quinazoline-8-carboxamide (64)

The compound was isolated by chiral chromatography from 4-(3-chlorophenyl)pyrrolidin-3-yl)amino)quinazoline-8-carboxamide(trans_racemic). LC-MS (M+1=367, obsd=367).

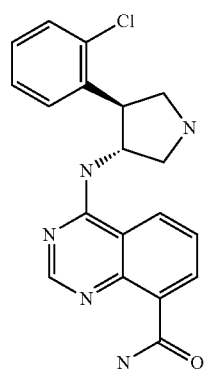 [SMILES: NC(=O)c1cccc2c(N[C@H]3CNC[C@@H]3c3ccccc3Cl)ncnc12]

4-(((3R,4S)-4-(2-chlorophenyl)pyrrolidin-3-yl) amino)quinazoline-8-carboxamide (65)

IC$_{50}$p70S6K [nM]: 340

The compound was isolated by chiral chromatography from 4-(2-chlorophenyl)pyrrolidin-3-yl)amino)quinazoline-8-carboxamide (trans_racemic). LC-MS (M+1=367, obsd=367)

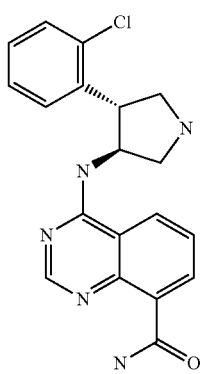 [SMILES: NC(=O)c1cccc2c(N[C@@H]3CNC[C@H]3c3ccccc3Cl)ncnc12]

4-(((3S,4R)-4-(2-chlorophenyl)pyrrolidin-3-yl)amino)quinazoline-8-carboxamide (66)

IC$_{50}$p70S6K [nM]: 1.4

The compound was isolated by chiral chromatography from 4-(2-chlorophenyl)pyrrolidin-3-yl)amino)quinazoline-8-carboxamide (trans_racemic). LC-MS (M+1=367, obsd=367)

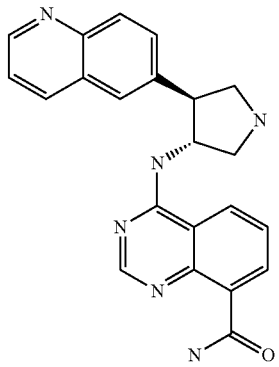

4-(((3S,4R)-4-(3-fluorophenyl)pyrrolidin-3-yl)amino)quinazoline-8-carboxamide (67)

IC$_{50}$p70S6K [nM]: 1.54

The compound was isolated by chiral chromatography from 4-(3-fluorophenyl)pyrrolidin-3-yl)amino)quinazoline-8-carboxamide. (trans_racemic). LC-MS (M+1=352, obsd=352).

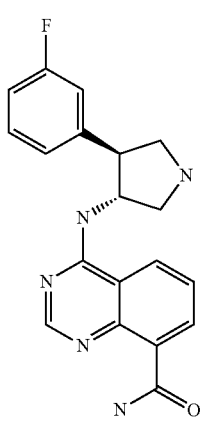 [SMILES: NC(=O)c1cccc2c(N[C@H]3CNC[C@@H]3c3cccc(F)c3)ncnc12]

4-(((3R,4S)-4-(3-fluorophenyl)pyrrolidin-3-yl)amino)quinazoline-8-carboxamide (68)

IC$_{50}$p70S6K [nM]: 48

The compound was isolated by chiral chromatography from 4-(3-fluorophenyl)pyrrolidin-3-yl)amino)quinazoline-8-carboxamide. (trans_racemic). LC-MS (M+1=352, obsd=352).

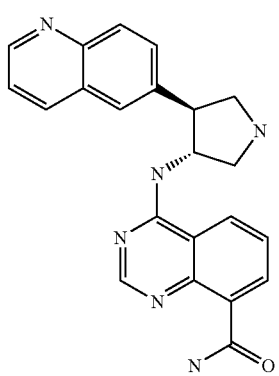 [SMILES: NC(=O)c1cccc2c(N[C@H]3CNC[C@@H]3c3ccc4ncccc4c3)ncnc12]

trans, racemic 4-(quinolin-6-yl)pyrrolidin-3-yl)amino)quinazoline-8-carboxamide (69)

IC$_{50}$p70S6K [nM]: 3.2

The compound was synthesized according to the procedure described for the preparation of example 2 using tert-butyl 3-amino-4-(quinolin-6-yl)pyrrolidine-1-carboxylate (racemic-trans) and methyl 4-chloroquinazoline-8-carboxylate. LC-MS (M+1=385, obsd=385).

4-(((3R,4S)-4-(quinolin-6-yl)pyrrolidin-3-yl)amino)quinazoline-8-carboxamide (70)

IC$_{50}$p70S6K [nM]: 3.3

The compound was isolated by chiral chromatography from 4-(quinolin-6-yl)pyrrolidin-3-yl)amino)quinazoline-8-carboxamide (trans_racemic). LC-MS (M+1=385, obsd=385).

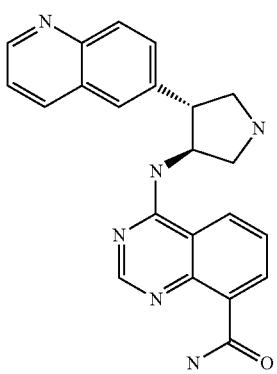 [SMILES: NC(=O)c1cccc2c(N[C@@H]3CNC[C@H]3c3ccc4ncccc4c3)ncnc12]

4-(((3S,4R)-4-(quinolin-6-yl)pyrrolidin-3-yl)amino)quinazoline-8-carboxamide (71)

IC$_{50}$p70S6K [nM]: 62

The compound was isolated by chiral chromatography from 4-(quinolin-6-yl)pyrrolidin-3-yl)amino)quinazoline-8-carboxamide. LC-MS (M+1=385, obsd=385).

4-(((3R,4S)-4-(3-methoxyphenyl)pyrrolidin-3-yl)amino)quinazoline-8-carboxamide (72)

IC$_{50}$p70S6K [nM]: 360

The compound was isolated by chiral chromatography from compound trans racemic 4-(3-methoxyphenyl)pyrrolidin-3-yl)amino)quinazoline-8-carboxamide. LC-MS (M+1=364, obsd=364).

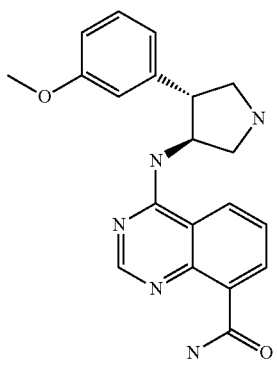 [SMILES: COc1cccc([C@@H]2CNC[C@H]2Nc2ncnc3c(C(N)=O)cccc23)c1]

4-(((3S,4R)-4-(3-methoxyphenyl)pyrrolidin-3-yl)amino)quinazoline-8-carboxamide (73)

IC$_{50}$p70S6K [nM]: 6.4

The compound was isolated by chiral chromatography from compound trans racemic 4-(3-methoxyphenyl)pyrrolidin-3-yl)amino)quinazoline-8-carboxamide. LC-MS (M+1=364, obsd=364).

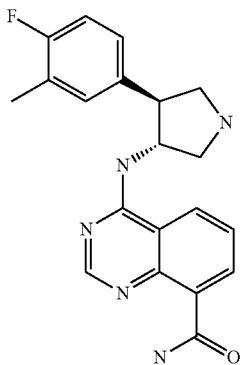

trans, racemic 4-(4-fluoro-3-methylphenyl)pyrrolidin-3-yl)amino)quinazoline-8-carboxamide (74)

IC$_{50}$p70S6K [nM]: 8.8

The compound was synthesized according to the procedure described for the preparation of example 2 using tert-butyl 3-amino-4-(4-fluoro-3-methylphenyl)pyrrolidine-1-carboxylate (racemic-trans) and methyl 4-chloroquinazoline-8-carboxylate. LC-MS (M+1=366, obsd=366).

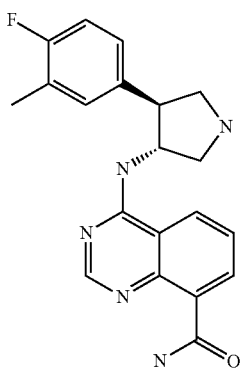 [SMILES: Cc1cc([C@H]2CNC[C@@H]2Nc2ncnc3c(C(N)=O)cccc23)ccc1F]

4-(((3R,4S)-4-(4-fluoro-3-methylphenyl)pyrrolidin-3-yl)amino)quinazoline-8-carboxamide (75)

IC$_{50}$p70S6K [nM]: 64

The compound was isolated by chiral chromatography from trans racemic 4-(4-fluoro-3-methylphenyl)pyrrolidin-3-yl)amino)quinazoline-8-carboxamide. LC-MS (M+1=366, obsd=366).

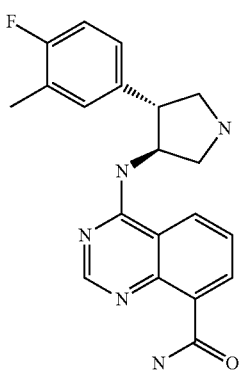

4-(((3S,4R)-4-(4-fluoro-3-methylphenyl)pyrrolidin-3-yl)amino)quinazoline-8-carboxamide (76)

IC$_{50}$p70S6K [nM]: 3.4

The compound was isolated by chiral chromatography from trans racemic 4-(4-fluoro-3-methylphenyl)pyrrolidin-3-yl)amino)quinazoline-8-carboxamide. LC-MS (M+1=366, obsd=366).

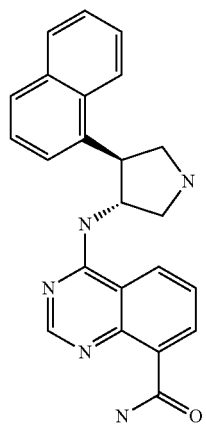 [SMILES: NC(=O)c1cccc2c(N[C@H]3CNC[C@@H]3c3cccc4ccccc34)ncnc12]

trans, racemic 4-(naphthalen-1-yl)pyrrolidin-3-yl)amino)quinazoline-8-carboxamide (77)

The compound was synthesized according to the procedure described for the preparation of example 2 using tert-butyl 3-amino-4-(naphthalen-1-yl)pyrrolidine-1-carboxylate (racemic-trans) and methyl 4-chloroquinazoline-8-carboxylate. LC-MS (M+1=384, obsd=384).

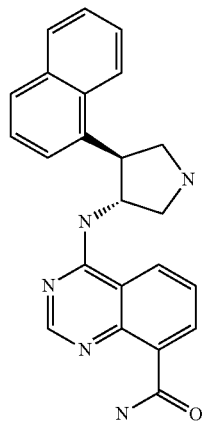 [SMILES: NC(=O)c1cccc2c(N[C@H]3CNC[C@@H]3c3cccc4ccccc34)ncnc12]

4-(((3R,4S)-4-(naphthalen-1-yl)pyrrolidin-3-yl)amino)quinazoline-8-carboxamide (78)

The compound was isolated by chiral chromatography from trans racemic 4-(naphthalen-1-yl)pyrrolidin-3-yl)amino)quinazoline-8-carboxamide. LC-MS (M+1=384, obsd=384).

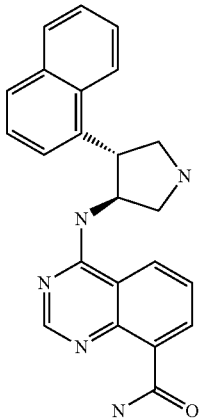 [SMILES: NC(=O)c1cccc2c(N[C@@H]3CNC[C@H]3c3cccc4ccccc34)ncnc12]

4-(((3S,4R)-4-(naphthalen-1-yl)pyrrolidin-3-yl)amino)quinazoline-8-carboxamide (79)

IC$_{50}$p70S6K [nM]: 1.2

The compound was isolated by chiral chromatography from trans racemic 4-(naphthalen-1-yl)pyrrolidin-3-yl)amino)quinazoline-8-carboxamide. LC-MS (M+1=384, obsd=384).

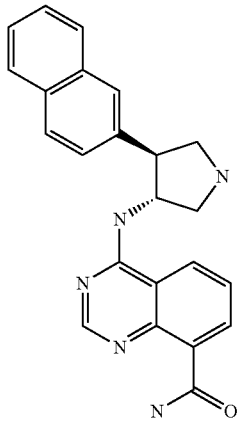 [SMILES: NC(=O)c1cccc2c(N[C@H]3CNC[C@@H]3c3ccc4ccccc4c3)ncnc12]

4-(((3R,4S)-4-(naphthalen-2-yl)pyrrolidin-3-yl)amino)quinazoline-8-carboxamide (80)

IC$_{50}$p70S6K [nM]: 24

The compound was isolated by chiral chromatography from trans racemic 4-(naphthalen-2-yl)pyrrolidin-3-yl)amino)quinazoline-8-carboxamide. LC-MS (M+1=384, obsd=384).

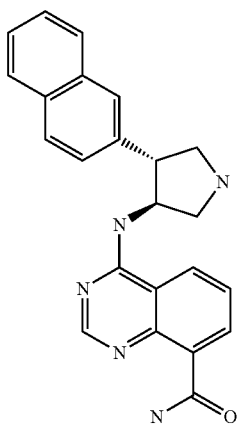 [SMILES: NC(=O)c1cccc2c(N[C@@H]3CNC[C@H]3c3ccc4ccccc4c3)ncnc12]

4-(((3S,4R)-4-(naphthalen-2-yl)pyrrolidin-3-yl)amino)quinazoline-8-carboxamide (81)

The compound was isolated by chiral chromatography from its trans racemic compound 4-(naphthalen-2-yl)pyrrolidin-3-yl)amino)quinazoline-8-carboxamide. LC-MS (M+1=384, obsd=384).

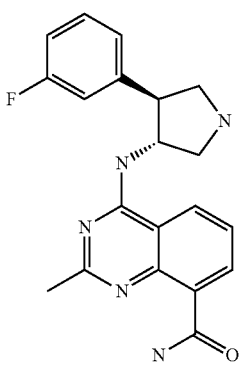 [SMILES: Cc1nc(N[C@H]2CNC[C@@H]2c2cccc(F)c2)c2cccc(C(N)=O)c2n1]

trans, racemic 4-(3-fluorophenyl)pyrrolidin-3-yl)amino)-2-methylquinazoline-8-carboxamide (82)

The compound was synthesized according to the procedure described for the preparation of example 2 using tert-butyl 3-amino-4-(3-fluorophenyl)pyrrolidine-1-carboxylate (racemic-trans) and methyl 4-chloro-2-methylquinazoline-8-carboxylate. LC-MS (M+1=366, obsd=366).

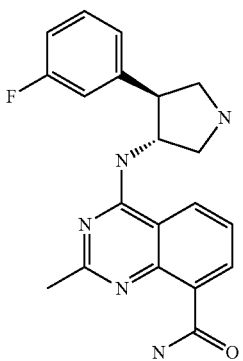

4-(((3R,4S)-4-(3-fluorophenyl)pyrrolidin-3-yl)amino)-2-methylquinazoline-8-carboxamide (83)

$IC_{50}$ p70S6K [nM]: 160

The compound was isolated by chiral chromatography from trans racemic 4-(3-fluorophenyl)pyrrolidin-3-yl)amino)-2-methylquinazoline-8-carboxamide. LC-MS (M+1=366, obsd=366).

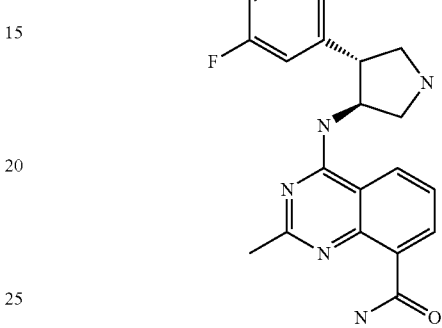

4-(((3S,4R)-4-(3-fluorophenyl)pyrrolidin-3-yl)amino)-2-methylquinazoline-8-carboxamide (84)

$IC_{50}$ p70S6K [nM]: 1.7

The compound was isolated by chiral chromatography from trans racemic 4-(3-fluorophenyl)pyrrolidin-3-yl)amino)-2-methylquinazoline-8-carboxamide. LC-MS (M+1=366, obsd=366).

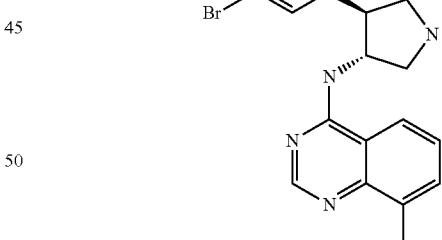

trans, racemic 4-(3-bromophenyl)pyrrolidin-3-yl)amino)quinazoline-8-carboxamide (85)

$IC_{50}$ p70S6K [nM]: 1.8

The compound was synthesized according to the procedure described for the preparation of example 2 using tert-butyl 3-amino-4-(3-bromophenyl)pyrrolidine-1-carboxylate (racemic-trans) and methyl 4-chloroquinazoline-8-carboxylate. LC-MS (M+1=411/413, obsd=411/413).

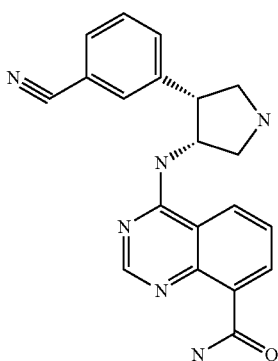 [SMILES: N#Cc1cccc([C@@H]2CNC[C@@H]2Nc2ncnc3c(C(N)=O)cccc23)c1]

cis, racemic 4-(3-cyanophenyl)pyrrolidin-3-yl)
amino)quinazoline-8-carboxamide (86)

$IC_{50}$p70S6K [nM]: 14

The compound was synthesized according to the procedure described for the preparation of example 2 using tert-butyl 3-amino-4-(3-cyanophenyl)pyrrolidine-1-carboxylate (Cis_racemic) and methyl 4-chloroquinazoline-8-carboxylate. LC-MS (M+1=359, obsd=359).

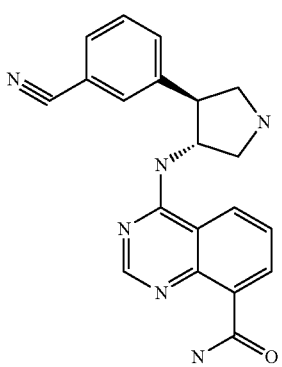 [SMILES: N#Cc1cccc([C@H]2CNC[C@@H]2Nc2ncnc3c(C(N)=O)cccc23)c1]

4-(((3R,4S)-4-(3-cyanophenyl)pyrrolidin-3-yl)
amino)quinazoline-8-carboxamide (87)

$IC_{50}$p70S6K [nM]: 81

The compound was isolated by chiral chromatography from trans racemic 4-(3-cyanophenyl)pyrrolidin-3-yl) amino)quinazoline-8-carboxamide.
LC-MS (M+1=359, obsd=359).

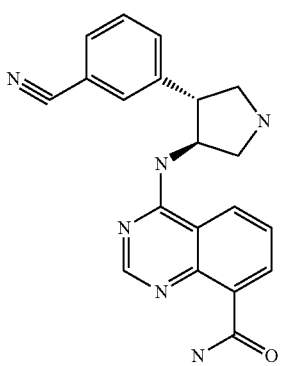 [SMILES: N#Cc1cccc([C@@H]2CNC[C@H]2Nc2ncnc3c(C(N)=O)cccc23)c1]

4-(((3S,4R)-4-(3-cyanophenyl)pyrrolidin-3-yl)
amino)quinazoline-8-carboxamide (88)

$IC_{50}$p70S6K [nM]: 2.4

The compound was isolated by chiral chromatography from trans racemic 4-(3-cyanophenyl)pyrrolidin-3-yl) amino)quinazoline-8-carboxamide.
LC-MS (M+1=359, obsd=359).

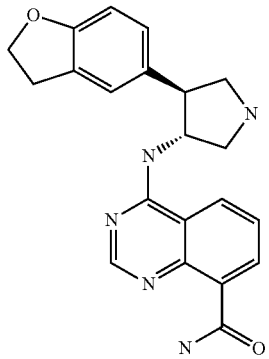 [SMILES: NC(=O)c1cccc2c(N[C@H]3CNC[C@@H]3c3ccc4c(c3)CCO4)ncnc12]

trans, racemic 4-(2,3-dihydrobenzofuran-5-yl)pyrrolidin-3-yl)amino)quinazoline-8-carboxamide (89)

$IC_{50}$p70S6K [nM]: 3.2

The compound was synthesized according to the procedure described for the preparation of example 2 using tert-butyl 3-amino-4-(2,3-dihydrobenzofuran-5-yl)pyrrolidine-1-carboxylate and methyl 4-chloroquinazoline-8-carboxylate. LC-MS (M+1=376, obsd=376).

4-(((3R,4S)-4-(2,3-dihydrobenzofuran-5-yl)pyrrolidin-3-yl)amino)quinazoline-8-carboxamide (90)

$IC_{50}$p70S6K [nM]: 4

The compound was isolated by chiral chromatography from its trans racemic compound 4-(2,3-dihydrobenzofuran-5-yl)pyrrolidin-3-yl)amino)quinazoline-8-carboxamide.
LC-MS (M+1=376, obsd=376).

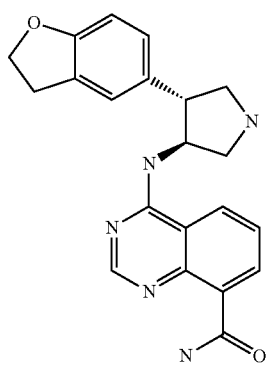 [SMILES: NC(=O)c1cccc2c(N[C@@H]3CNC[C@H]3c3ccc4c(c3)CCO4)ncnc12]

4-(((3S,4R)-4-(2,3-dihydrobenzofuran-5-yl)pyrrolidin-3-yl)amino)quinazoline-8-carboxamide (91)

IC$_{50}$p70S6K [nM]: 53
The compound was isolated by chiral chromatography from its trans racemic compound 4-(2,3-dihydrobenzofuran-5-yl)pyrrolidin-3-yl)amino)quinazoline-8-carboxamide.
LC-MS (M+1=376, obsd=376).

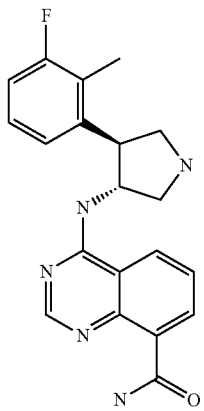 [SMILES: Cc1c(F)cccc1[C@H]1CNC[C@@H]1Nc1ncnc2c(C(N)=O)cccc12]

trans, racemic 4-(3-fluoro-2-methylphenyl)pyrrolidin-3-yl)amino)quinazoline-8-carboxamide (92)

IC$_{50}$p70S6K [nM]: 2
The compound was synthesized according to the procedure described for the preparation of example 2 using tert-butyl 3-amino-4-(3-fluoro-2-methylphenyl)pyrrolidine-1-carboxylate (racemic-trans) and methyl 4-chloroquinazoline-8-carboxylate. LC-MS (M+1=366, obsd=366).

4-(((3R,4S)-4-(3-fluoro-2-methylphenyl)pyrrolidin-3-yl)amino)quinazoline-8-carboxamide (93)

IC$_{50}$p70S6K [nM]: 1.2
The compound was isolated by chiral chromatography from trans racemic 4-(3-fluoro-2-methylphenyl)pyrrolidin-3-yl)amino)quinazoline-8-carboxamide.
LC-MS (M+1=366, obsd=366).

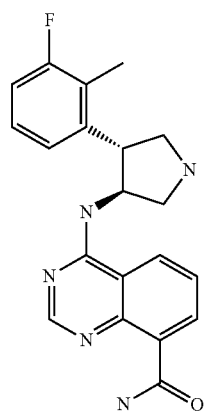

4-(((3S,4R)-4-(3-fluoro-2-methylphenyl)pyrrolidin-3-yl)amino)quinazoline-8-carboxamide (94)

IC$_{50}$p70S6K [nM]: 52
The compound was isolated by chiral chromatography from trans racemic 4-(3-fluoro-2-methylphenyl)pyrrolidin-3-yl)amino)quinazoline-8-carboxamide.
LC-MS (M+1=366, obsd=366).

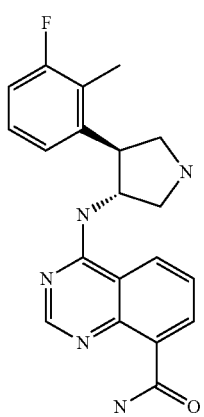 [SMILES: Cc1c(F)cccc1[C@H]1CNC[C@@H]1Nc1ncnc2c(C(N)=O)cccc12]

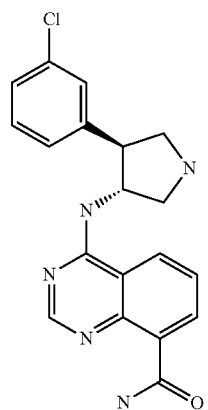 [SMILES: NC(=O)c1cccc2c(N[C@H]3CNC[C@@H]3c3cccc(Cl)c3)ncnc12]

4-(((3R,4S)-4-(3-chlorophenyl)pyrrolidin-3-yl) amino)quinazoline-8-carboxamide (95)

IC$_{50}$p70S6K [nM]: 48

The compound was isolated by chiral chromatography from trans racemic 4-(3-chlorophenyl)pyrrolidin-3-yl) amino)quinazoline-8-carboxamide.

LC-MS (M+1=367, obsd=367).

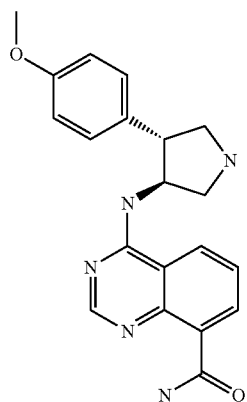 [SMILES: COc1ccc([C@@H]2CNC[C@H]2Nc2ncnc3c(C(N)=O)cccc23)cc1]

4-(((3S,4R)-4-(4-methoxyphenyl)pyrrolidin-3-yl) amino)quinazoline-8-carboxamide (96)

IC$_{50}$p70S6K [nM]: 4.1

The compound was isolated by chiral chromatography from trans racemic 4-(4-methoxyphenyl)pyrrolidin-3-yl) amino)quinazoline-8-carboxamide.

LC-MS (M+1=364, obsd=364).

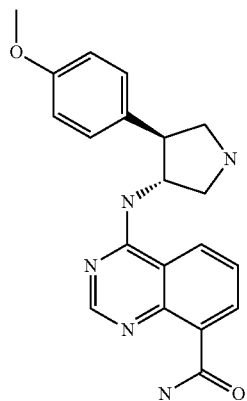 [SMILES: COc1ccc([C@H]2CNC[C@@H]2Nc2ncnc3c(C(N)=O)cccc23)cc1]

4-(((3R,4S)-4-(4-methoxyphenyl)pyrrolidin-3-yl) amino)quinazoline-8-carboxamide (97)

IC$_{50}$p70S6K [nM]: 81

The compound was isolated by chiral chromatography from trans racemic 4-(4-methoxyphenyl)pyrrolidin-3-yl) amino)quinazoline-8-carboxamide.

LC-MS (M+1=364, obsd=364).

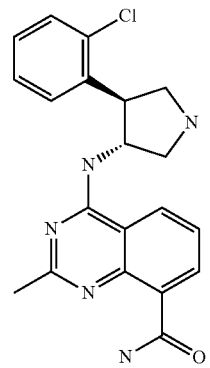 [SMILES: Cc1nc(N[C@H]2CNC[C@@H]2c2ccccc2Cl)c2cccc(C(N)=O)c2n1]

trans, racemic 2-chlorophenyl)pyrrolidin-3-yl) amino)-2-methylquinazoline-8-carboxamide (98)

IC$_{50}$p70S6K [nM]: 2.7

The compound was synthesized according to the procedure described for the preparation of example 2 using tert-butyl 3-amino-4-(2-chlorophenyl)pyrrolidine-1-carboxylate and methyl 4-chloro-2-methylquinazoline-8-carboxylate. LC-MS (M+1=381, obsd=381).

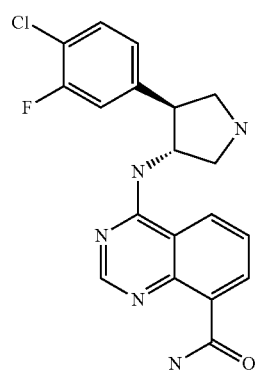 [SMILES: NC(=O)c1cccc2c(N[C@H]3CNC[C@@H]3c3ccc(Cl)c(F)c3)ncnc12]

trans, racemic 4-(4-chloro-3-fluorophenyl)pyrrolidin-3-yl)amino)quinazoline-8-carboxamide (99)

IC$_{50}$p70S6K [nM]: 0.088

The compound was synthesized according to the procedure described for the preparation of example 2 using tert-butyl 3-amino-4-(4-chloro-3-fluorophenyl)pyrrolidine-1-carboxylate and methyl 4-chloroquinazoline-8-carboxylate. LC-MS (M+1=314, obsd=314).

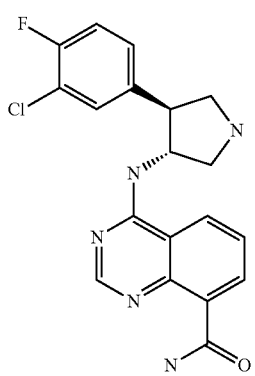

trans, racemic 4-(3-chloro-4-fluorophenyl)pyrrolidin-3-yl)amino)quinazoline-8-carboxamide (100)

IC$_{50}$p70S6K [nM]: 1.4
The compound was synthesized according to the procedure described for the preparation of example 2 using tert-butyl 3-amino-4-(3-chloro-4-fluorophenyl)pyrrolidine-1-carboxylate and methyl 4-chloroquinazoline-8-carboxylate. LC-MS (M+1=314, obsd=314).

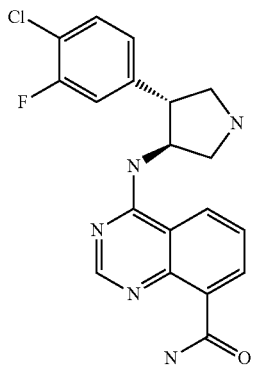 [SMILES: NC(=O)c1cccc2c(N[C@@H]3CNC[C@H]3c3ccc(Cl)c(F)c3)ncnc12]

4-(((3S,4R)-4-(4-chloro-3-fluorophenyl)pyrrolidin-3-yl)amino)quinazoline-8-carboxamide (101)

IC$_{50}$p70S6K [nM]: 1.1
The compound was isolated by chiral chromatography from trans racemic 4-(4-chloro-3-fluorophenyl)pyrrolidin-3-yl)amino)quinazoline-8-carboxamide. LC-MS (M+1=314, obsd=314).

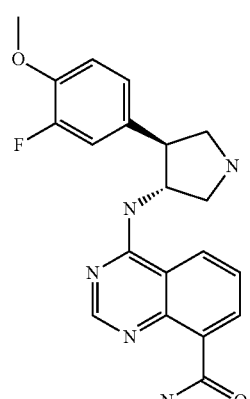

trans, racemic 4-(3-fluoro-4-methoxyphenyl)pyrrolidin-3-yl)amino)quinazoline-8-carboxamide (102)

IC$_{50}$p70S6K [nM]: 2.9
The compound was synthesized according to the procedure described for the preparation of example 2 using tert-butyl 3-amino-4-(3-fluoro-4-methoxyphenyl)pyrrolidine-1-carboxylate and methyl 4-chloroquinazoline-8-carboxylate. LC-MS (M+1=311, obsd=311).

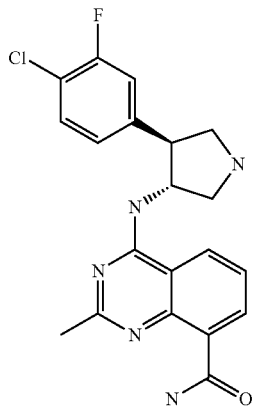 [SMILES: Cc1nc(N[C@H]2CNC[C@@H]2c2ccc(Cl)c(F)c2)c2cccc(C(N)=O)c2n1]

trans, racemic 4-(4-chloro-3-fluorophenyl)pyrrolidin-3-yl)amino)-2-methylquinazoline-8-carboxamide (103)

IC$_{50}$p70S6K [nM]: 1.8
The compound was synthesized according to the procedure described for the preparation of example 2 using tert-butyl 3-amino-4-(4-chloro-3-fluorophenyl)pyrrolidine-1-carboxylate and methyl 4-chloro-2-methylquinazoline-8-carboxylate. LC-MS (M+1=401, obsd=401).

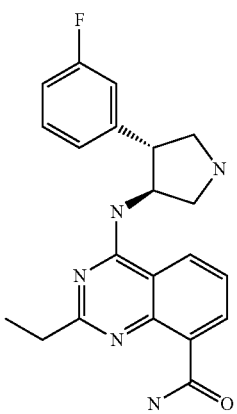 [SMILES: CCc1nc(N[C@@H]2CNC[C@H]2c2cccc(F)c2)c2cccc(C(N)=O)c2n1]

trans, racemic 2-ethyl-4-(((3S,4R)-4-(3-fluorophenyl)pyrrolidin-3-yl)amino)quinazoline-8-carboxamide (104)

The compound was isolated by chiral chromatography from trans racemic 4-(4-chloro-3-fluorophenyl)pyrrolidin-3-yl)amino)-2-ethylquinazoline-8-carboxamide. LC-MS (M+1=380, obsd=380).

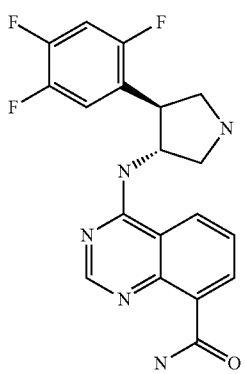 [SMILES: NC(=O)c1cccc2c(N[C@H]3CNC[C@@H]3c3cc(F)c(F)cc3F)ncnc12]

trans, racemic 4-(((3R,4S)-4-(2,4,5-trifluorophenyl)
pyrrolidin-3-yl)amino)quinazoline-8-carboxamide
(105)

IC$_{50}$p70S6K [nM]: 420

The compound was isolated by chiral chromatography from its trans racemic compound 4-(2,4,5-trifluorophenyl)pyrrolidin-3-yl)amino)quinazoline-8-carboxamide. LC-MS (M+1=388, obsd=388).

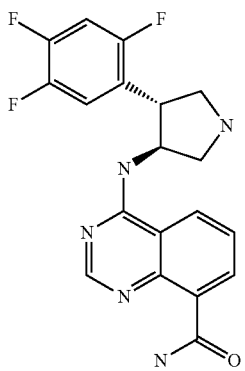

4-(((3S,4R)-4-(2,4,5-trifluorophenyl)pyrrolidin-3-yl)
amino)quinazoline-8-carboxamide (106)

IC$_{50}$p70S6K [nM]: 2.8

The compound was isolated by chiral chromatography from its trans racemic compound 4-(2,4,5-trifluorophenyl)pyrrolidin-3-yl)amino)quinazoline-8-carboxamide. LC-MS (M+1=388, obsd=388).

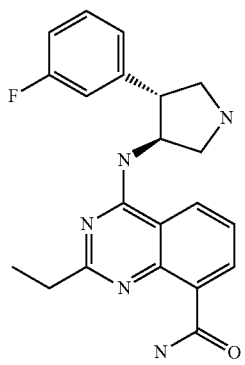

trans, racemic 2-ethyl-4-(3-fluorophenyl)pyrrolidin-
3-yl)amino)quinazoline-8-carboxamide (107)

IC$_{50}$p70S6K [nM]: 5.5

The compound was synthesized according to the procedure described for the preparation of example 2 using tert-butyl 3-amino-4-(3-fluorophenyl)pyrrolidine-1-carboxylate and methyl 4-chloro-2-ethylquinazoline-8-carboxylate. LC-MS (M+1=380, obsd=380).

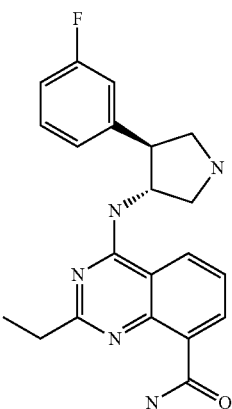 [SMILES: CCc1nc(N[C@H]2CNC[C@@H]2c2cccc(F)c2)c2cccc(C(N)=O)c2n1]

2-ethyl-4-(((3R,4S)-4-(3-fluorophenyl)pyrrolidin-3-
yl)amino)quinazoline-8-carboxamide (108)

The compound was isolated by chiral chromatography from trans racemic 2-ethyl-4-(3-fluorophenyl)pyrrolidin-3-yl)amino)quinazoline-8-carboxamide. LC-MS (M+1=380, obsd=380).

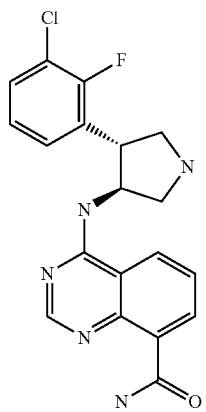 [SMILES: NC(=O)c1cccc2c(N[C@@H]3CNC[C@H]3c3cccc(Cl)c3F)ncnc12]

trans, racemic 4-(3-chloro-2-fluorophenyl)pyrroli-
din-3-yl)amino)quinazoline-8-carboxamide (109)

IC$_{50}$p70S6K [nM]: 2.1

The compound was synthesized according to the procedure described for the preparation of example 2 using tert-butyl 3-amino-4-(3-chloro-2-fluorophenyl)pyrrolidine-1-carboxylate and methyl 4-chloroquinazoline-8-carboxylate. LC-MS (M+1=385, obsd=385).

83

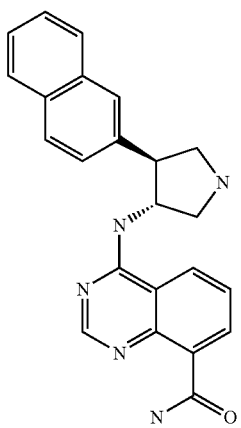 [SMILES: NC(=O)c1cccc2c(N[C@H]3CNC[C@@H]3c3ccc4ccccc4c3)ncnc12]

trans, racemic 4-(naphthalen-2-yl)pyrrolidin-3-yl)
amino)quinazoline-8-carboxamide (110)

$IC_{50}$p70S6K [nM]: 1.54

The compound was synthesized according to the procedure described for the preparation of example 2 using tert-butyl 3-amino-4-(naphthalen-2-yl)pyrrolidine-1-carboxylate and methyl 4-chloroquinazoline-8-carboxylate. LC-MS (M+1=384, obsd=384).

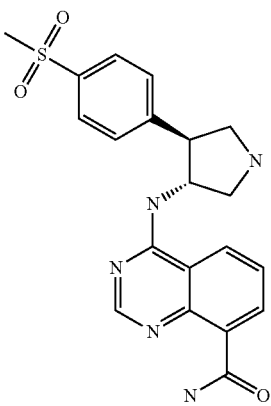 [SMILES: CS(=O)(=O)c1ccc([C@H]2CNC[C@@H]2Nc2ncnc3c(C(N)=O)cccc23)cc1]

trans, racemic 4-(4-(methylsulfonyl)phenyl)pyrrolidin-3-yl)amino)quinazoline-8-carboxamide (111)

$IC_{50}$p70S6K [nM]: 7.5

The compound was synthesized according to the procedure described for the preparation of example 2 using tert-butyl 3-amino-4-(4-(methylsulfonyl)phenyl)pyrrolidine-1-carboxylate and methyl 4-chloroquinazoline-8-carboxylate. LC-MS (M+1=412, obsd=412).

84

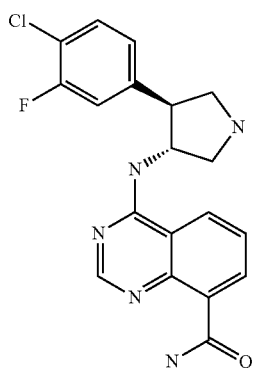 [SMILES: NC(=O)c1cccc2c(N[C@H]3CNC[C@@H]3c3ccc(Cl)c(F)c3)ncnc12]

4-(((3R,4S)-4-(4-chloro-3-fluorophenyl)pyrrolidin-3-yl)amino)quinazoline-8-carboxamide (112)

$IC_{50}$p70S6K [nM]: 330

The compound was isolated by chiral chromatography from trans racemic compound 4-(4-chloro-3-fluorophenyl)pyrrolidin-3-yl)amino)quinazoline-8-carboxamide. LC-MS (M+1=385, obsd=385).

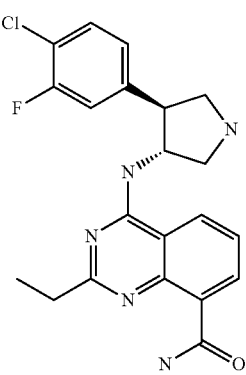 [SMILES: CCc1nc(N[C@H]2CNC[C@@H]2c2ccc(Cl)c(F)c2)c2cccc(C(N)=O)c2n1]

trans, racemic 4-(4-chloro-3-fluorophenyl)pyrrolidin-3-yl)amino)-2-ethylquinazoline-8-carboxamide (113)

The compound was synthesized according to the procedure described for the preparation of example 2 using butyl 3-amino-4-(4-chloro-3-fluorophenyl)pyrrolidine-1-carboxylate and methyl 4-chloro-2-ethylquinazoline-8-carboxylate. LC-MS (M+1=413, obsd=413).

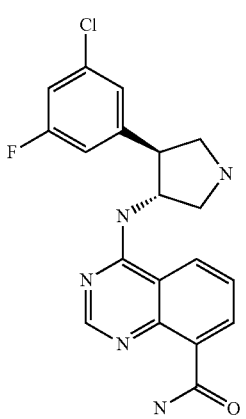 [SMILES: NC(=O)c1cccc2c(N[C@H]3CNC[C@@H]3c3cc(F)cc(Cl)c3)ncnc12]

trans, racemic 4-(3-chloro-5-fluorophenyl)pyrrolidin-3-yl)amino)quinazoline-8-carboxamide (114)

IC$_{50}$p70S6K [nM]: 1.5

The compound was synthesized according to the procedure described for the preparation of example 2 using tert-butyl 3-amino-4-(3-chloro-5-fluorophenyl)pyrrolidine-1-carboxylate and methyl 4-chloroquinazoline-8-carboxylate. LC-MS (M+1=385, obsd=385).

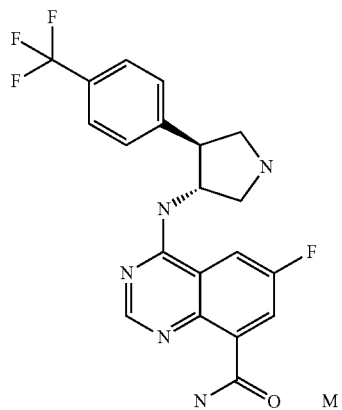

trans, racemic 6-fluoro-4-(((3R,4S)-4-(4-(trifluoromethyl)phenyl)pyrrolidin-3-yl)amino)quinazoline-8-carboxamide (115)

The compound was synthesized according to the procedure described for the preparation of example 2 using tert-butyl 3-amino-4-(3-chloro-5-fluorophenyl)pyrrolidine-1-carboxylate and methyl 4-chloro-6-fluoroquinazoline-8-carboxylate. LC-MS (M+1=420, obsd=420).

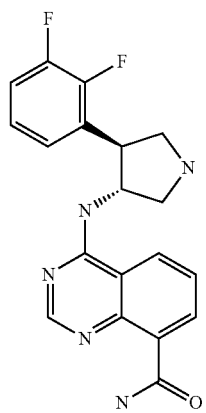 [SMILES: NC(=O)c1cccc2c(N[C@H]3CNC[C@@H]3c3cccc(F)c3F)ncnc12]

trans, racemic 4-(2,3-difluorophenyl)pyrrolidin-3-yl)amino)quinazoline-8-carboxamide (116)

IC$_{50}$p70S6K [nM]: 4.1

The compound was synthesized according to the procedure described for the preparation of example 2 using tert-butyl 3-amino-4-(2,3-difluorophenyl)pyrrolidine-1-carboxylate and methyl 4-chloroquinazoline-8-carboxylate. LC-MS (M+1=370, obsd=370).

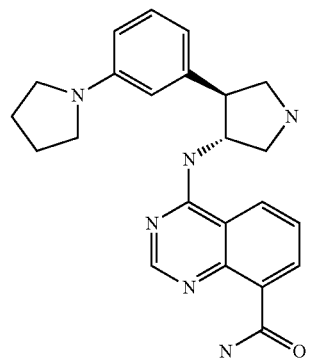 [SMILES: NC(=O)c1cccc2c(N[C@H]3CNC[C@@H]3c3cccc(N4CCCC4)c3)ncnc12]

trans, racemic 4-(((3R,4S)-4-(3-(pyrrolidin-1-yl)phenyl)pyrrolidin-3-yl)amino)quinazoline-8-carboxamide (117)

IC$_{50}$p70S6K [nM]: 5.9

The compound was synthesized according to the procedure described for the preparation of example 2 using tert-butyl 3-amino-4-(3-(pyrrolidin-1-yl)phenyl)pyrrolidine-1-carboxylate and methyl 4-chloroquinazoline-8-carboxylate. LC-MS (M+1=403, obsd=403).

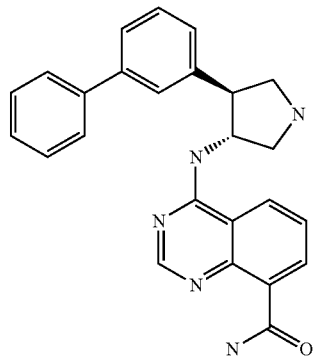 [SMILES: NC(=O)c1cccc2c(N[C@H]3CNC[C@@H]3c3cccc(-c4ccccc4)c3)ncnc12]

trans, racemic 4-([1,1'-biphenyl]-3-yl)pyrrolidin-3-yl)amino)quinazoline-8-carboxamide (118)

A reaction mixture of 3-[8-(aminocarbonyl)quinazolin-4-yl]amino-4-(3-bromophenyl)pyrrolidine-1-carboxylate (trans-racemic) (15.00 mg; 0.03 mmol; 1.00 eq.), phenylboronic acid (10.71 mg; 0.09 mmol; 3.00 eq.), palladium (2+) diacetate (3.94 mg; 0.02 mmol; 0.60 eq.), dicyclohexyl (2',6'-dimethoxybiphenyl-2-yl)phosphine (12.02 mg; 0.03 mmol; 1.00 eq.) and dipotassium carbonate (12.14 mg; 0.09 mmol; 3.00 eq.) in dioxane 1 ml and water 0.1 ml in 5 ml microwave tube, was placed in microwave at 120° C. for 20 mins.

LC-MS showed conversion was completed.

Filtered, the filtrated was removed off solvent, and the residue was added methanol 1 ml, then hydrogen chloride (1.00 ml; 4.00 M; 4.00 mmol; 136.64 eq.) 1 ml, stirred for 2 h. lc-MS showed desired.

Purified by HPLC, collected desired product.

LC-MS (M+1=411, obsd=411).

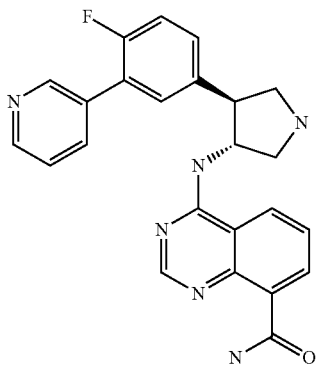 [SMILES: NC(=O)c1cccc2c(N[C@H]3CNC[C@@H]3c3ccc(F)c(-c4cccnc4)c3)ncnc12]

trans, racemic 4-(4-fluoro-3-(pyridin-3-yl)phenyl)pyrrolidin-3-yl)amino)quinazoline-8-carboxamide (119)

$IC_{50}$p70S6K [nM]: 15

The compound was synthesized according to the procedure described for the preparation of example 118 using tert-butyl 3-((8-carbamoylquinazolin-4-yl)amino)-4-(3-chloro-4-fluorophenyl)pyrrolidine-1-carboxylate (trans_racemic) coupling with pyridin-3-ylboronic acid, then removed off boc. LC-MS (M+1=429, obsd=429).

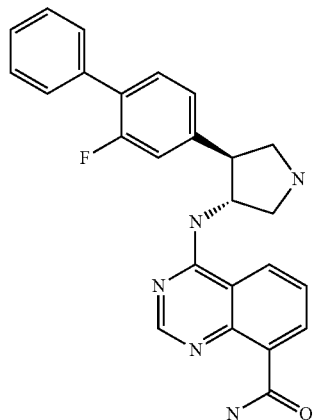 [SMILES: NC(=O)c1cccc2c(N[C@H]3CNC[C@@H]3c3ccc(-c4ccccc4)c(F)c3)ncnc12]

trans, racemic 4-(2-fluoro-[1,1'-biphenyl]-4-yl)pyrrolidin-3-yl)amino)quinazoline-8-carboxamide (120)

$IC_{50}$p70S6K [nM]: 1.4

The compound was synthesized according to the procedure described for the preparation of example 118 using tert-butyl 3-((8-carbamoylquinazolin-4-yl)amino)-4-(4-chloro-3-fluorophenyl)pyrrolidine-1-carboxylate (trans_racemic) coupling with phenylboronic acid, then removed off boc. LC-MS (M+1=428, obsd=428).

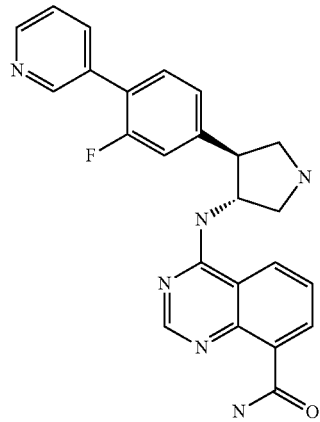

trans, racemic 4-(3-fluoro-4-(pyridin-3-yl)phenyl)pyrrolidin-3-yl)amino)quinazoline-8-carboxamide (121)

$IC_{50}$p70S6K [nM]: 6.0

The compound was synthesized according to the procedure described for the preparation of example 118 using tert-butyl 3-((8-carbamoylquinazolin-4-yl)amino)-4-(4-chloro-3-fluorophenyl)pyrrolidine-1-carboxylate (trans_racemic) coupling with pyridin-3-ylboronic acid, then removed off boc. LC-MS (M+1=429, obsd=429).

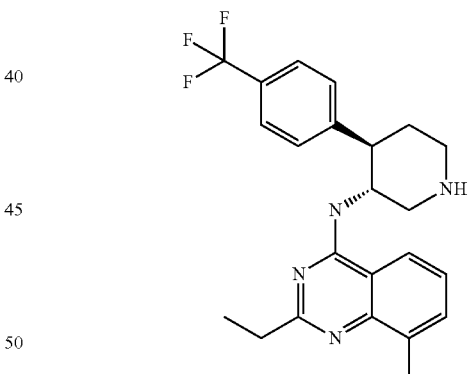

trans, racemic 2-ethyl-4-((4-(trifluoromethyl)phenyl)piperidin-3-yl)amino)quinazoline-8-carboxamide (122)

The compound was synthesized according to the procedure described for the preparation of example 27 using racemic, trans racemic tert-butyl 3-amino-4-(3-(trifluoromethyl)phenyl)piperidine-1-carboxylate and methyl 4-chloro-2-ethylquinazoline-8-carboxylate. LC-MS (M+H=444, obsd=444).

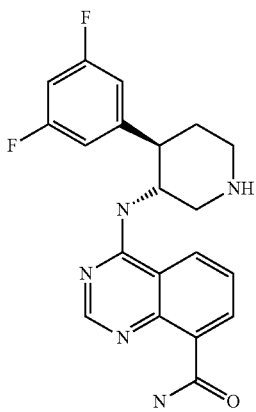

trans, racemic 4-(3,5-difluorophenyl)piperidin-3-yl)
amino)quinazoline-8-carboxamide (123)

IC$_{50}$p70S6K [nM]: 2.3

The compound was synthesized according to the procedure described for the preparation of example 27 using trans racemic tert-butyl 3-amino-4-(3,5-difluorophenyl)piperidine-1-carboxylate and methyl 4-chloro-quinazoline-8-carboxylate. LC-MS (M+H=444, obsd=444).

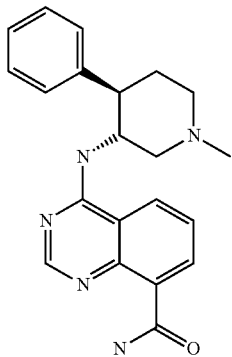

trans, racemic 1-methyl-4-phenylpiperidin-3-yl)
amino)quinazoline-8-carboxamide (124)

IC$_{50}$p70S6K [nM]: 22

A reaction mixture of 4-phenylpiperidin-3-yl]aminoquinazoline-8-carboxamide trifluoroacetate (trans_racemic) (21.00 mg; 0.05 mmol; 1.00 eq.), formic acid (0.01 ml; 0.11 mmol; 2.50 eq.) and formaldehyde (0.00 ml; 0.05 mmol; 1.20 eq.) in ethanol was stirred at 80° C. for 3 hr, LC-MS showed clean desired.

Lyophilized, collected desired product. LC-MS (M+H=408, obsd=408).

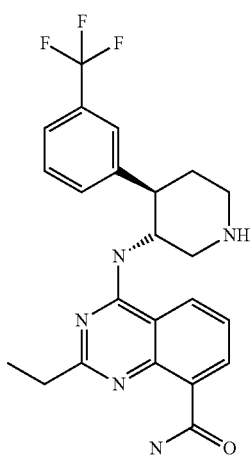

trans, racemic 2-ethyl-4-(3-(trifluoromethyl)phenyl)
piperidin-3-yl)amino)quinazoline-8-carboxamide
(125)

IC$_{50}$p70S6K [nM]: 3.9

The compound was synthesized according to the procedure described for the preparation of example 27 using trans racemic tert-butyl 3-amino-4-(3-(trifluoromethyl)phenyl)piperidine-1-carboxylate and methyl 4-chloro-2-ethylquinazoline-8-carboxylate. LC-MS (M+H=444, obsd=444).

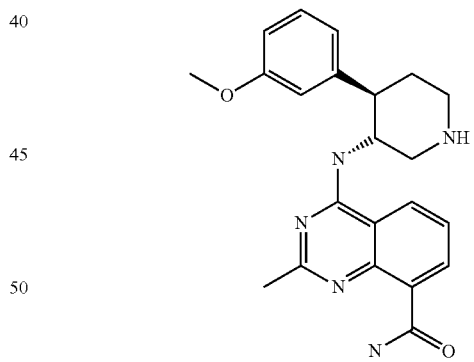

trans, racemic 4-(3-methoxyphenyl)piperidin-3-yl)
amino)-2-methylquinazoline-8-carboxamide (126)

IC$_{50}$p70S6K [nM]: 4.5

The compound was synthesized according to the procedure described for the preparation of example 27 using trans racemic tert-butyl 3-amino-4-(3-methoxyphenyl)piperidine-1-carboxylate and methyl 4-chloro-2-methylquinazoline-8-carboxylate. LC-MS (M+H=392, obsd=392).

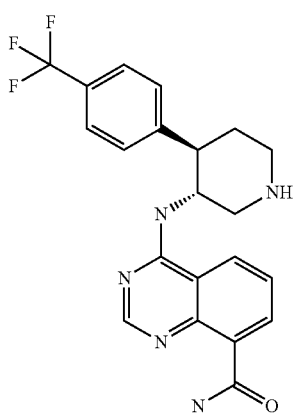 [SMILES: NC(=O)c1cccc2c(N[C@H]3CNCC[C@@H]3c3ccc(C(F)(F)F)cc3)ncnc12]

trans, racemic 4-(4-(trifluoromethyl)phenyl)piperidin-3-yl)amino)quinazoline-8-carboxamide (127)

IC$_{50}$p70S6K [nM]: 2.0

The compound was synthesized according to the procedure described for the preparation of example 27 using trans racemic tert-butyl 3-amino-4-(4-(trifluoromethyl)phenyl)piperidine-1-carboxylate and methyl 4-chloro-quinazoline-8-carboxylate. LC-MS (M+H=416, obsd=416).

4-(((3S,4S)-4-(4-(trifluoromethyl)phenyl)piperidin-3-yl)amino)quinazoline-8-carboxamide) (128)

IC$_{50}$p70S6K [nM]: 230

The compound was isolated by chiral chromatography from trans racemic 4-(4-(trifluoromethyl)phenyl)piperidin-3-yl)amino)quinazoline-8-carboxamide. LC-MS (M+H=416, obsd=416).

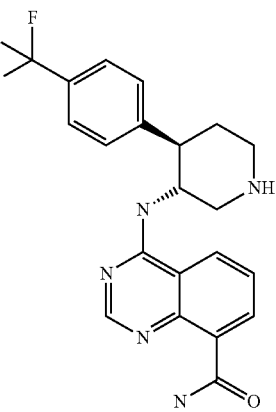
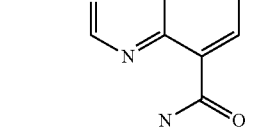

4-(((3R,4R)-4-(4-(trifluoromethyl)phenyl)piperidin-3-yl)amino)quinazoline-8-carboxamide (129)

IC$_{50}$p70S6K [nM]: 1.2

The compound was isolated by chiral chromatography from trans racemic 4-(4-(trifluoromethyl)phenyl)piperidin-3-yl)amino)quinazoline-8-carboxamide. LC-MS (M+H=416, obsd=416).

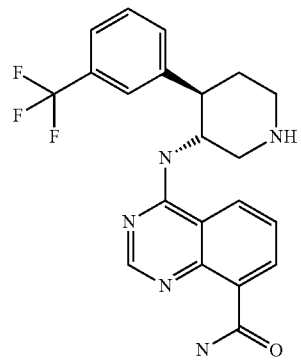

4-(((3R,4R)-4-(3-(trifluoromethyl)phenyl)piperidin-3-yl)amino)quinazoline-8-carboxamide (130)

IC$_{50}$p70S6K [nM]: 1.2

The compound was isolated by chiral chromatography from trans racemic 4-(3-(trifluoromethyl)phenyl)piperidin-3-yl)amino)quinazoline-8-carboxamide. LC-MS (M+H=416, obsd=416).

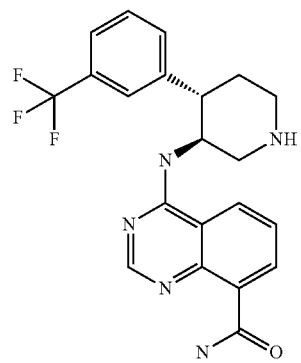 [SMILES: NC(=O)c1cccc2c(N[C@@H]3CNCC[C@H]3c3cccc(C(F)(F)F)c3)ncnc12]

4-(((3S,4S)-4-(3-(trifluoromethyl)phenyl)piperidin-3-yl)amino)quinazoline-8-carboxamide (131)

IC$_{50}$p70S6K [nM]: 160

The compound was isolated by chiral chromatography from trans racemic 4-(3-(trifluoromethyl)phenyl)piperidin-3-yl)amino)quinazoline-8-carboxamide. LC-MS (M+H=416, obsd=416).

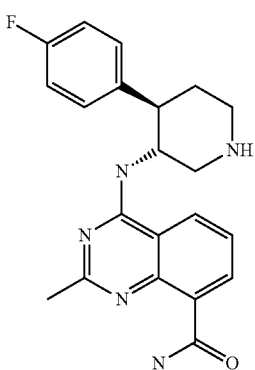

trans, racemic 4-(4-fluorophenyl)piperidin-3-yl)amino)-2-methylquinazoline-8-carboxamide (132)

$IC_{50}$p70S6K [nM]: 5.4

The compound was synthesized according to the procedure described for the preparation of example 27 using trans racemic tert-butyl 3-amino-4-(4-fluorophenyl)piperidine-1-carboxylate and methyl 4-chloro-2 methylquinazoline-8-carboxylate. LC-MS (M+H=380, obsd=380).

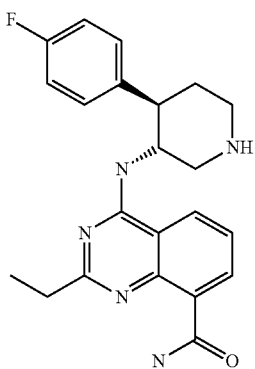

trans, racemic 2-ethyl-4-(4-fluorophenyl)piperidin-3-yl)amino)quinazoline-8-carboxamide (133)

$IC_{50}$p70S6K [nM]: 3.6

The compound was synthesized according to the procedure described for the preparation of example 27 using trans racemic tert-butyl 3-amino-4-(4-fluorophenyl)piperidine-1-carboxylate and methyl 4-chloro-2 ethylquinazoline-8-carboxylate. LC-MS (M+H=394, obsd=394).

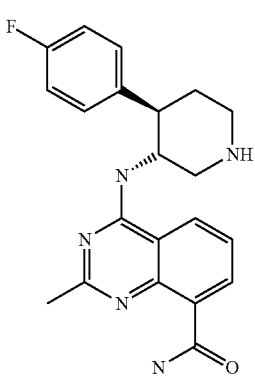

trans, racemic 4-(4-fluorophenyl)piperidin-3-yl)amino)-2-methylquinazoline-8-carboxamide (134)

$IC_{50}$p70S6K [nM]: 4.2

The compound was synthesized according to the procedure described for the preparation of example 27 using trans racemic tert-butyl 3-amino-4-(4-fluorophenyl)piperidine-1-carboxylate and methyl 4-chloro-2 methylquinazoline-8-carboxylate. LC-MS (M+H=380, obsd=380).

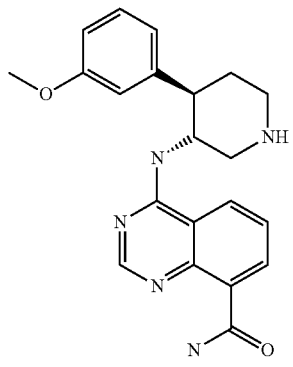

trans, racemic 4-(3-methoxyphenyl)piperidin-3-yl)amino)quinazoline-8-carboxamide (135)

$IC_{50}$p70S6K [nM]: 4.3

The compound was synthesized according to the procedure described for the preparation of example 27 using trans racemic tert-butyl 3-amino-4-(3-methoxyphenyl)piperidine-1-carboxylate and methyl 4-chloro-quinazoline-8-carboxylate. LC-MS (M+H=378, obsd=378).

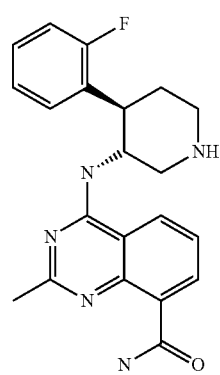

trans, racemic 4-(2-fluorophenyl)piperidin-3-yl)amino)-2-methylquinazoline-8-carboxamide (136)

$IC_{50}$p70S6K [nM]: 210

The compound was synthesized according to the procedure described for the preparation of example 27 using trans racemic tert-butyl 3-amino-4-(2-fluorophenyl)piperidine-1-carboxylate and methyl 4-chloro-2-methylquinazoline-8-carboxylate. LC-MS (M+H=380, obsd=380).

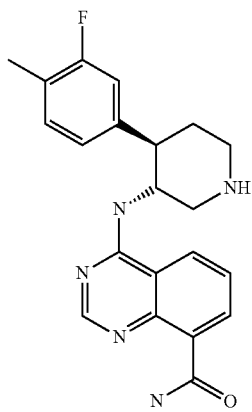

trans, racemic 4-(3-fluoro-4-methylphenyl)piperidin-3-yl)amino)quinazoline-8-carboxamide (137)

The compound was synthesized according to the procedure described for the preparation of example 27 using trans racemic tert-butyl 3-amino-4-(3-fluoro-4-methylphenyl)piperidine-1-carboxylate and methyl 4-chloro-quinazoline-8-carboxylate. LC-MS (M+H=380, obsd=380).

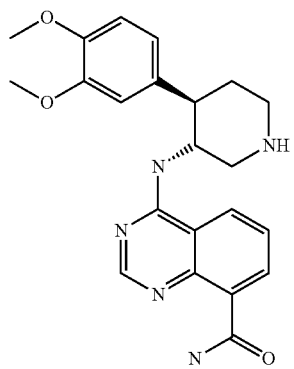

trans, racemic 4-(3,4-dimethoxyphenyl)piperidin-3-yl)amino)quinazoline-8-carboxamide (139)

$IC_{50}$ p70S6K [nM]: 18

The compound was synthesized according to the procedure described for the preparation of example 27 using trans racemic tert-butyl 3-amino-4-(3,4-dimethoxyphenyl)piperidine-1-carboxylate and methyl 4-chloro-quinazoline-8-carboxylate. LC-MS (M+H=408, obsd=408).

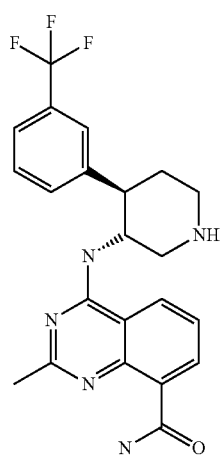

trans, racemic 2-methyl-4-(((3R,4R)-4-(3-(trifluoromethyl)phenyl)piperidin-3-yl)amino)quinazoline-8-(138)

$IC_{50}$ p70S6K [nM]: 2.7

The compound was synthesized according to the procedure described for the preparation of example 27 using trans racemic tert-butyl 3-amino-4-(3-(trifluoromethyl)phenyl)piperidine-1-carboxylate and methyl 4-chloro-2-methylquinazoline-8-carboxylate. LC-MS (M+H=430, obsd=431).

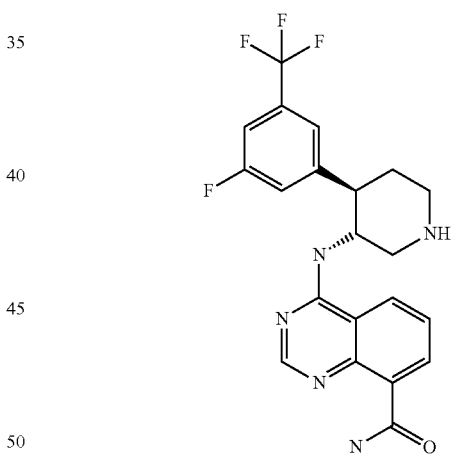

trans, racemic 4-(3-fluoro-5-(trifluoromethyl)phenyl)piperidin-3-yl)amino)quinazoline-8-carboxamide (140)

$IC_{50}$ p70S6K [nM]: 3.1

The compound was synthesized according to the procedure described for the preparation of example 27 using trans racemic tert-butyl 3-amino-4-(3-fluoro-5-(trifluoromethyl)phenyl)piperidine-1-carboxylate and methyl 4-chloro-quinazoline-8-carboxylate. LC-MS (M+H=434, obsd=434).

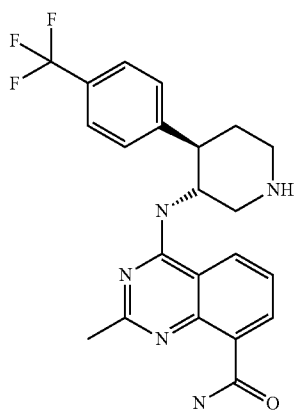

trans, racemic 2-methyl-4-(4-(trifluoromethyl)phenyl)piperidin-3-yl)amino)quinazoline-8-carboxamide (141)

$IC_{50}$p70S6K [nM]: 2.9

The compound was synthesized according to the procedure described for the preparation of example 27 using trans racemic tert-butyl 3-amino-4-(4-(trifluoromethyl)phenyl)piperidine-1-carboxylate and methyl 4-chloro-2-methylquinazoline-8-carboxylate. LC-MS (M+H=430, obsd=430).

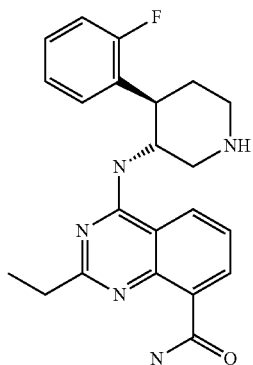

trans, racemic 2-ethyl-4-(2-fluorophenyl)piperidin-3-yl)amino)quinazoline-8-carboxamide (142)

$IC_{50}$p70S6K [nM]: 450

The compound was synthesized according to the procedure described for the preparation of example 27 using trans racemic tert-butyl 3-amino-4-(2-fluorophenyl)piperidine-1-carboxylate and methyl 4-chloro-2-ethylquinazoline-8-carboxylate. LC-MS (M+H=394, obsd=394).

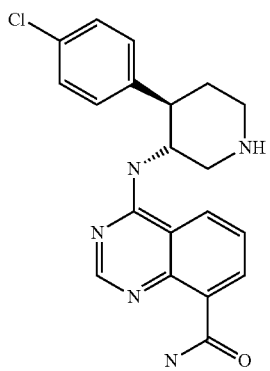

trans, racemic 4-(4-chlorophenyl)piperidin-3-yl)amino)quinazoline-8-carboxamide (143)

The compound was synthesized according to the procedure described for the preparation of example 27 using trans racemic tert-butyl 3-amino-4-(4-chlorophenyl)piperidine-1-carboxylate and methyl 4-chloro-quinazoline-8-carboxylate. LC-MS (M+H=381, obsd=381).

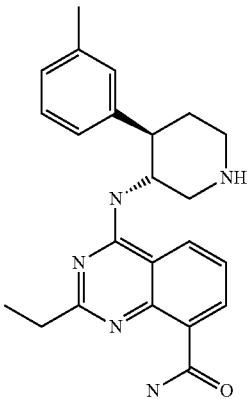

trans, racemic 2-ethyl-4-(m-tolyl)piperidin-3-yl)amino)quinazoline-8-carboxamide (144)

$IC_{50}$p70S6K [nM]: 5.0

The compound was synthesized according to the procedure described for the preparation of example 27 using trans racemic tert-butyl 3-amino-4-(m-tolyl)piperidine-1-carboxylate and methyl 4-chloro-2-ethylquinazoline-8-carboxylate. LC-MS (M+H=390, obsd=390).

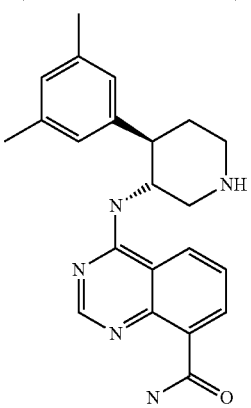

trans, racemic 4-((4-(3,5-dimethylphenyl)piperidin-3-yl)amino)quinazoline-8-carboxamide (145)

IC$_{50}$p70S6K [nM]: 10

The compound was synthesized according to the procedure described for the preparation of example 27 using trans racemic tert-butyl 3-amino-4-(3,5-dimethylphenyl)piperidine-1-carboxylate and methyl 4-chloroquinazoline-8-carboxylate. LC-MS (M+H=376, obsd=376).

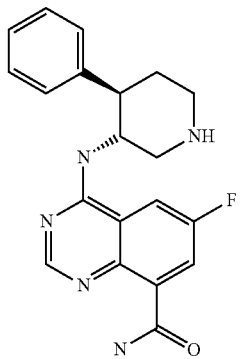

trans, racemic 6-fluoro-4-(((3R,4R)-4-phenylpiperidin-3-yl)amino)quinazoline-8-carboxamide (146)

IC$_{50}$p70S6K [nM]: 7.1

The compound was synthesized according to the procedure described for the preparation of example 27 using trans racemic tert-butyl 3-amino-4-phenylpiperidine-1-carboxylate and methyl 4-chloro-6-fluoroquinazoline-8-carboxylate. LC-MS (M+H=366, obsd=366).

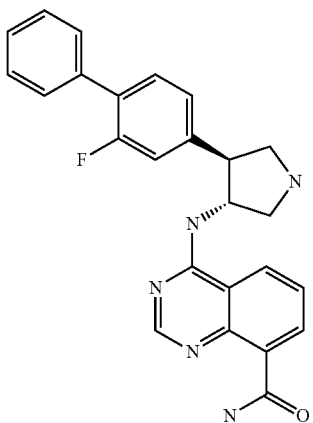 [SMILES: NC(=O)c1cccc2c(N[C@H]3CNC[C@@H]3c3ccc(-c4ccccc4)c(F)c3)ncnc12]

4-(((3R,4S)-4-(2-fluoro-[1,1'-biphenyl]-4-yl)pyrrolidin-3-yl)amino)quinazoline-8-carboxamide (147)

The compound was isolated by chiral chromatography from its trans racemic compound 4-(2-fluoro-[1,1'-biphenyl]-4-yl)pyrrolidin-3-yl)amino)quinazoline-8-carboxamide. LC-MS (M+1=428, obsd=428).

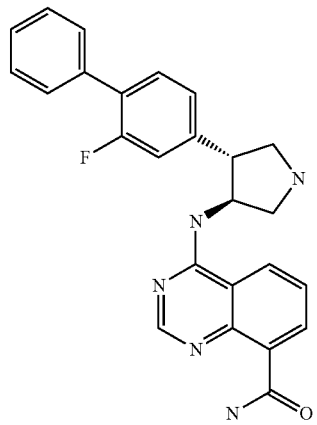 [SMILES: NC(=O)c1cccc2c(N[C@@H]3CNC[C@H]3c3ccc(-c4ccccc4)c(F)c3)ncnc12]

4-(((3S,4R)-4-(2-fluoro-[1,1'-biphenyl]-4-yl)pyrrolidin-3-yl)amino)quinazoline-8-carboxamide (148)

The compound was isolated by chiral chromatography from its trans racemic compound 4-(2-fluoro-[1,1'-biphenyl]-4-yl)pyrrolidin-3-yl)amino)quinazoline-8-carboxamide. LC-MS (M+1=428, obsd=428).

Biological Activity

P70S6K Enzyme Assay

P70S6K inhibitor compounds are diluted and plated in 96 well plates. A reaction mixture including the following components is then added to the compound plate to initiate the enzyme reaction; P70S6K (3 nM, T412E mutant, Millipore) is mixed with 24 µM ATP in an assay buffer containing 100 mM Hepes (pH 7.5), 5 mM MgCl2, 1 mM DTT, 0.015% Brij and 1 µM of the substrate peptide FITC-AHA-AKRRRLSSLRA-OH (derived from the S6 ribosomal protein sequence, FITC=fluorescein isothiocyanate, AHA=6-aminohexanoic acid). The reaction is incubated for 90 min at 25° C., before the addition of 10 mM EDTA to stop the reaction. The proportion of substrate and product (phosphorylated) peptide is analyzed on a Caliper Life Sciences Lab Chip 3000, using a pressure of −1.4 psi, and upstream and downstream voltages of −3000 and −700 respectively. Product peaks are resolved before substrate peaks on the resulting chromatograms.

To assess the inhibitory potential of the compounds, IC50-values were determined, as shown in Chemical Synthesis section above.

The present invention having been described by the description of the invention and the non-limiting examples above, is now defined by the spirit and scope of the following claims.

The invention claimed is:

1. A compound of Formula (I)

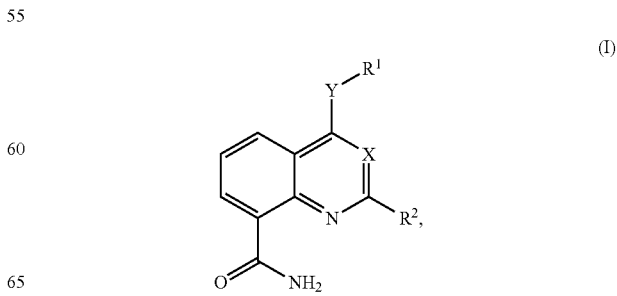

(I)

and pharmaceutically acceptable salts, solvates, or solvates of salts thereof,
wherein:
X is N,
Y is NH or is absent,
R¹ is

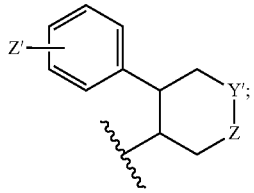

each Y' is independently CH2 or NH such that when Y' is NH, Z is CH2 or absent and when Y' is CH2, Z is NH,
each Z is independently CH2, NH or is absent such that when Z is CH2 or absent, Y' is NH and when Z is NH, Y' is CH2, and
each Z' is independently Ar, alkyl, halogen, OMe, CF3, CN, OCF3, SO₂Me, H (mono, di, or tri-substituted with any above combination)
R² is A, or H,
Ar is a mono- or bicyclic aromatic homo- or heterocycle having 0, 1, 2, 3 or 4 N, O and/or S atoms and 5, 6, 7, 8, 9, or 10 skeleton atoms, which may be unsubstituted or, independently of one another, mono-, di- or trisubstituted by Hal, A, OH, SH, OA, NH₂, NHA, NA₂, NO₂, CN, OCN, SCN, COOH, COOA, CONH₂, CONHA, CONA₂, NHCOA, NHCONHA, NHCONH₂, NHSO₂A, CHO, COA, SO₂NH₂, SO₂A and/or SO₂Hal, and in which a ring N-atom may be substituted by an O-atom to form an N-oxide group, and in which in the case of a bicyclic aromatic cycle on of the two rings may be partly saturated,
A is unbranched or branched linear or cyclic alkyl having 1, 2, 3, 4, 5, 6, 7 or 8 C atoms, in which one or two CH2 groups may be replaced by an O or S atom and/or by an —NH—, —CO—, —NHCOO—, —NHCONH—, —N(LA)-, —CONH—, —NHCO— or —CH═CH— group, and in which 1-3 H atoms may be replaced by Hal, and in which one or two CH₃ groups may be replaced by OH, SH, NH₂, NH(LA), N(LA)₂, NHCOOH, NHCONH₂ or CN,
LA is unbranched or branched, linear alkyl having 1, 2, 3 or 4 C atoms, wherein 1, 2 or 3 H atoms may be replaced by Hal and
Hal is F, Cl, Br or I.

2. The compound according to claim 1 and pharmaceutically acceptable salts, solvates, or solvates of salts thereof, wherein:
X is N,
Y is NH,
R²' is A or H,
A is unbranched or branched linear or cyclic alkyl having 1, 2, 3, 4, 5, 6, 7 or 8 C atoms, in which one or two CH₂ groups may be replaced by an O or S atom and/or by an —NH—, —CO—, —NHCOO—, —NHCONH—, —N(LA)-, —CONH—, —NHCO— or —CH═CH— group, and in which 1-3 H atoms may be replaced by Hal, and in which one or two CH₃ groups may be replaced by OH, SH, NH₂, NH(LA), N(LA)₂, NHCOOH, NHCONH₂ or CN,
LA is unbranched or branched, linear alkyl having 1, 2, 3 or 4 C atoms, wherein 1, 2 or 3 H atoms may be replaced by Hal and
Hal is F, Cl, Br or I.

3. The compound of claim 1 of Formula (II)

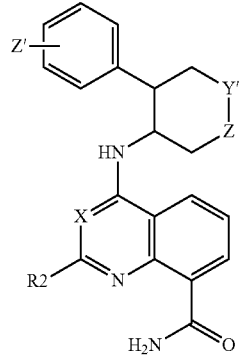

and pharmaceutically acceptable salts, solvates, or solvates of salts,
wherein:
X is N,
R² is A or H,
Y' is CH2 or NH such that when Y' is NH, Z is CH2 or absent and when Y' is CH2, Z is NH,
Z is CH2, NH or is absent such that when Z is CH2 or absent, Y is NH and when Z is NH, Y is CH2, and
Z' Ar, alkyl, halogen, OMe, CF3, CN, OCF3, SO₂Me, H (mono, di, or tri-substituted with any above combination).

4. A compound selected from the group consisting of:
trans racemic 4-((4-(3-fluorophenyl)pyrrolidin-3-yl)amino)quinazoline-8-carboxamide;
trans racemic 4-((4-phenylpyrrolidin-3-yl)amino)quinazoline-8-carboxamide;
4-((4-(2-fluorophenyl)pyrrolidin-3-yl)amino)quinazoline-8-carboxamide;
4-((4-(4-fluorophenyl)pyrrolidin-3-yl)amino)quinazoline-8-carboxamide;
4-((4-(4-methoxyphenyl)pyrrolidin-3-yl)amino)quinazoline-8-carboxamide;
4-((4-(3-methoxyphenyl)pyrrolidin-3-yl)amino)quinazoline-8-carboxamide,
4-((4-(2-methoxyphenyl)pyrrolidin-3-yl)amino)quinazoline-8-carboxamide;
trans, racemic 4-((4-(3-chlorophenyl)pyrrolidin-3-yl)amino)quinazoline-8-carboxamide;
trans, racemic 4-((4-(2-chloro-6-fluorophenyl)pyrrolidin-3-yl)amino)-quinazoline-8-carboxamide;
trans, racemic 4-((4-(3-bromophenyl)pyrrolidin-3-yl)amino)quinazoline-8-carboxamide;
trans, racemic 4-((4-(3-fluorophenyl)-1-methylpyrrolidin-3-yl)amino)quinazoline-8-carboxamide;
trans, racemic 4-((-4-(naphthalen-2-yl)pyrrolidin-3-yl)amino)quinazoline-8-carboxamide;
trans, racemic 4-((4-(naphthalen-1-yl)pyrrolidin-3-yl)amino)quinazoline-8-carboxamide;
6-methyl-4-((4-phenylpyrrolidin-3-yl)amino)quinazoline-8-carboxamide,
2-methyl-4-((4-phenylpyrrolidin-3-yl)amino)quinazoline-8-carboxamide;
4-((4-(4-fluorophenyl)pyrrolidin-3-yl)amino)-2-methylquinazoline-8-carboxamide;
4-((4-(4-methoxyphenyl)pyrrolidin-3-yl)amino)-2-methylquinazoline-8-carboxamide;
4-((4-(4-fluorophenyl)-1-methylpyrrolidin-3-yl)amino) quinoline-8-carboxamide;

4-((4-phenylpyrrolidin-3-yl)amino)quinoline-8-carboxamide;
4-((4-(3-fluorophenyl)pyrrolidin-3-yl)amino)quinoline-8-carboxamide;
4-((4-(2-fluorophenyl)pyrrolidin-3-yl)amino)quinoline-8-carboxamide;
4-((4-(2-methoxyphenyl)pyrrolidin-3-yl)amino)quinoline-8-carboxamide;
4-((4-(3-methoxyphenyl)pyrrolidin-3-yl)amino)quinoline-8-carboxamide;
4-((4-(4-methoxyphenyl)pyrrolidin-3-yl)amino)quinoline-8-carboxamide;
trans-4-(4-Phenylcarbamoyl-pyrrolidin-3-ylamino)-quinazoline-8-carboxylic acid amide;
trans, racemic 4-((4-phenylpiperidin-3-yl)amino)quinazoline-8-carboxamide;
racemic, trans 4-((4-(3-fluorophenyl)piperidin-3-yl)amino)quinazoline-8-carboxamide;
cis, racemic 4-((4-phenylpiperidin-3-yl)amino)quinazoline-8-carboxamide;
trans, racemic 4-((4-(3-(trifluoromethyl)phenyl)piperidin-3-yl)amino)quinazoline-8-carboxamide;
trans, racemic 4-((4-(m-tolyl)piperidin-3-yl)amino)quinazoline-8-carboxamide;
trans, racemic 4-((4-(4-fluorophenyl)piperidin-3-yl)amino)quinazoline-8-carboxamide;
trans, racemic Benzyl 3-((8-carbamoylquinazolin-4-yl)amino)-4-(3-fluoro-4-methylphenyl)piperidine-1-carboxylate;
racemic, trans 4-((4-(3-fluoro-4-methylphenyl)piperidin-3-yl)amino)quinazoline-8-carboxamide;
trans, racemic 4-((4-(3-fluorophenyl)piperidin-3-yl)amino)-2-methylquinazoline-8-carboxamide;
trans, racemic 2-ethyl-4-((4-(3-fluorophenyl)piperidin-3-yl)amino)quinazoline-8-carboxamide;
trans, racemic 2-ethyl-4-((4-phenylpiperidin-3-yl)amino)quinazoline-8-carboxamide;
trans, racemic 2-methyl-4-((4-phenylpiperidin-3-yl)amino)quinazoline-8-carboxamide;
trans, racemic 4-((4-phenylpiperidin-3-yl)amino)quinoline-8-carboxamide;
trans, racemic Ethyl 8-carbamoyl-4-(4-phenylpiperidin-3-yl)amino)quinoline-3-carboxylate;
trans, racemic 8-carbamoyl-4-((4-phenylpiperidin-3-yl)amino)quinoline-3-carboxylic acid;
4-(3-fluoro-4-methylphenyl)pyrrolidin-3-yl)amino)quinazoline-8-carboxamide;
4-(3-fluoro-5-(trifluoromethyl)phenyl)pyrrolidin-3-yl)amino)quinazoline-8-carboxamide;
4-(((3S,4R)-4-(3-fluoro-5-(trifluoromethyl)phenyl)pyrrolidin-3-yl)amino)quinazoline-8-carboxamide;
4-(((3R,4S)-4-(3-fluoro-5-(trifluoromethyl)phenyl)pyrrolidin-3-yl)amino)quinazoline-8-carboxamide;
4-(3-(trifluoromethyl)phenyl)pyrrolidin-3-yl)amino)quinazoline-8-carboxamide;
4-(((3S,4R)-4-(3-(trifluoromethyl)phenyl)pyrrolidin-3-yl)amino)quinazoline-8-carboxamide;
4-(((3R,4S)-4-(3-(trifluoromethyl)phenyl)pyrrolidin-3-yl)amino)quinazoline-8-carboxamide;
4-(3-(trifluoromethyl)phenyl)pyrrolidin-3-yl)amino)quinazoline-8-carboxamide;
4-(4-(trifluoromethyl)phenyl)pyrrolidin-3-yl)amino)quinazoline-8-carboxamide;
4-(((3R,4S)-4-(4-(trifluoromethyl)phenyl)pyrrolidin-3-yl)amino)quinazoline-8-carboxamide;
4-(((3R,4R)-4-(4-(trifluoromethyl)phenyl)pyrrolidin-3-yl)amino)quinazoline-8-carboxamide;
4-(3-(trifluoromethoxy)phenyl)pyrrolidin-3-yl)amino)quinazoline-8-carboxamide;
4-(3-(trifluoromethoxy)phenyl)pyrrolidin-3-yl)amino)quinazoline-8-carboxamide;
4-(((3R,4S)-4-(3-(trifluoromethoxy)phenyl)pyrrolidin-3-yl)amino)quinazoline-8-carboxamide;
4-(((3R,4R)-4-(3-(trifluoromethoxy)phenyl)pyrrolidin-3-yl)amino)quinazoline-8-carboxamide;
4-(4-(trifluoromethoxy)phenyl)pyrrolidin-3-yl)amino)quinazoline-8-carboxamide;
4-(((3R,4S)-4-(4-(trifluoromethoxy)phenyl)pyrrolidin-3-yl)amino)quinazoline-8-carboxamide;
4-(((3S,4R)-4-(4-(trifluoromethoxy)phenyl)pyrrolidin-3-yl)amino)quinazoline-8-carboxamide;
4-(((3S,4R)-4-(3-fluoro-4-methoxyphenyl)pyrrolidin-3-yl)amino)quinazoline-8-carboxamide;
4-(((3R,4S)-4-(3-fluoro-4-methoxyphenyl)pyrrolidin-3-yl)amino)quinazoline-8-carboxamide;
4-(((3R,4S)-4-(3-chlorophenyl)pyrrolidin-3-yl)amino)quinazoline-8-carboxamide;
4-(((3R,4S)-4-(2-chlorophenyl)pyrrolidin-3-yl)amino)quinazoline-8-carboxamide;
4-(((3S,4R)-4-(2-chlorophenyl)pyrrolidin-3-yl)amino)quinazoline-8-carboxamide;
4-(((3S,4R)-4-(3-fluorophenyl)pyrrolidin-3-yl)amino)quinazoline-8-carboxamide;
4-(((3R,4S)-4-(3-fluorophenyl)pyrrolidin-3-yl)amino)quinazoline-8-carboxamide;
4-(quinolin-6-yl)pyrrolidin-3-yl)amino)quinazoline-8-carboxamide;
4-(((3R,4S)-4-(quinolin-6-yl)pyrrolidin-3-yl)amino)quinazoline-8-carboxamide;
4-(((3S,4R)-4-(quinolin-6-yl)pyrrolidin-3-yl)amino)quinazoline-8-carboxamide;
4-(((3R,4S)-4-(3-methoxyphenyl)pyrrolidin-3-yl)amino)quinazoline-8-carboxamide;
4-(((3S,4R)-4-(3-methoxyphenyl)pyrrolidin-3-yl)amino)quinazoline-8-carboxamide;
4-(4-fluoro-3-methylphenyl)pyrrolidin-3-yl)amino)quinazoline-8-carboxamide;
4-(((3R,4S)-4-(4-fluoro-3-methylphenyl)pyrrolidin-3-yl)amino)quinazoline-8-carboxamide;
4-(((3S,4R)-4-(4-fluoro-3-methylphenyl)pyrrolidin-3-yl)amino)quinazoline-8-carboxamide;
4-(naphthalen-1-yl)pyrrolidin-3-yl)amino)quinazoline-8-carboxamide;
4-(((3R,4S)-4-(naphthalen-1-yl)pyrrolidin-3-yl)amino)quinazoline-8-carboxamide;
4-(((3S,4R)-4-(naphthalen-1-yl)pyrrolidin-3-yl)amino)quinazoline-8-carboxamide;
4-(((3R,4S)-4-(naphthalen-2-yl)pyrrolidin-3-yl)amino)quinazoline-8-carboxamide;
4-(((3S,4R)-4-(naphthalen-2-yl)pyrrolidin-3-yl)amino)quinazoline-8-carboxamide;
4-(3-fluorophenyl)pyrrolidin-3-yl)amino)-2-methylquinazoline-8-carboxamide;
4-(((3R,4S)-4-(3-fluorophenyl)pyrrolidin-3-yl)amino)-2-methylquinazoline-8-carboxamide;
4-(((3S,4R)-4-(3-fluorophenyl)pyrrolidin-3-yl)amino)-2-methylquinazoline-8-carboxamide;
4-(3-bromophenyl)pyrrolidin-3-yl)amino)quinazoline-8-carboxamide;
4-(3-cyanophenyl)pyrrolidin-3-yl)amino)quinazoline-8-carboxamide;
4-(((3R,4S)-4-(3-cyanophenyl)pyrrolidin-3-yl)amino)quinazoline-8-carboxamide;

4-(((3S,4R)-4-(3-cyanophenyl)pyrrolidin-3-yl)amino)
quinazoline-8-carboxamide;
4-(2,3-dihydrobenzofuran-5-yl)pyrrolidin-3-yl)amino)
quinazoline-8-carboxamide;
4-(((3R,4S)-4-(2,3-dihydrobenzofuran-5-yl)pyrrolidin-3-yl)amino)quinazoline-8-carboxamide;
4-(((3S,4R)-4-(2,3-dihydrobenzofuran-5-yl)pyrrolidin-3-yl)amino)quinazoline-8-carboxamide;
4-(3-fluoro-2-methylphenyl)pyrrolidin-3-yl)amino)quinazoline-8-carboxamide;
4-(((3R,4S)-4-(3-fluoro-2-methylphenyl)pyrrolidin-3-yl)amino)quinazoline-8-carboxamide;
4-(((3S,4R)-4-(3-fluoro-2-methylphenyl)pyrrolidin-3-yl)amino)quinazoline-8-carboxamide;
4-(((3R,4S)-4-(3-chlorophenyl)pyrrolidin-3-yl)amino)
quinazoline-8-carboxamide;
4-(((3S,4R)-4-(4-methoxyphenyl)pyrrolidin-3-yl)amino)
quinazoline-8-carboxamide;
4-(((3R,4S)-4-(4-methoxyphenyl)pyrrolidin-3-yl)amino)
quinazoline-8-carboxamide;
2-chlorophenyl)pyrrolidin-3-yl)amino)-2-methylquinazoline-8-carboxamide;
4-(4-chloro-3-fluorophenyl)pyrrolidin-3-yl)amino)quinazoline-8-carboxamide;
4-(3-chloro-4-fluorophenyl)pyrrolidin-3-yl)amino)quinazoline-8-carboxamide;
4-(((3S,4R)-4-(4-chloro-3-fluorophenyl)pyrrolidin-3-yl)amino)quinazoline-8-carboxamide;
4-(3-fluoro-4-methoxyphenyl)pyrrolidin-3-yl)amino)quinazoline-8-carboxamide;
4-(4-chloro-3-fluorophenyl)pyrrolidin-3-yl)amino)-2-methylquinazoline-8-carboxamide;
2-ethyl-4-(((3S,4R)-4-(3-fluorophenyl)pyrrolidin-3-yl)amino)quinazoline-8-carboxamide;
4-(((3R,4S)-4-(2,4,5-trifluorophenyl)pyrrolidin-3-yl)amino)quinazoline-8-carboxamide;
4-(((3S,4R)-4-(2,4,5-trifluorophenyl)pyrrolidin-3-yl)amino)quinazoline-8-carboxamide;
2-ethyl-4-(3-fluorophenyl)pyrrolidin-3-yl)amino)quinazoline-8-carboxamide;
2-ethyl-4-(((3R,4S)-4-(3-fluorophenyl)pyrrolidin-3-yl)amino)quinazoline-8-carboxamide;
4-(3-chloro-2-fluorophenyl)pyrrolidin-3-yl)amino)quinazoline-8-carboxamide;
4-(naphthalen-2-yl)pyrrolidin-3-yl)amino)quinazoline-8-carboxamide;
4-(4-(methylsulfonyl)phenyl)pyrrolidin-3-yl)amino)quinazoline-8-carboxamide;
4-(((3R,4S)-4-(4-chloro-3-fluorophenyl)pyrrolidin-3-yl)amino)quinazoline-8-carboxamide;
4-(4-chloro-3-fluorophenyl)pyrrolidin-3-yl)amino)-2-ethylquinazoline-8-carboxamide;
4-(3-chloro-5-fluorophenyl)pyrrolidin-3-yl)amino)quinazoline-8-carboxamide;
6-fluoro-4-(((3R,4S)-4-(4-(trifluoromethyl)phenyl)pyrrolidin-3-yl)amino)quinazoline-8-carboxamide;
4-(2,3-difluorophenyl)pyrrolidin-3-yl)amino)quinazoline-8-carboxamide;
4-(((3R,4S)-4-(3-(pyrrolidin-1-yl)phenyl)pyrrolidin-3-yl)amino)quinazoline-8-carboxamide;
4-([1,1'-biphenyl]-3-yl)pyrrolidin-3-yl)amino)quinazoline-8-carboxamide;
4-(4-fluoro-3-(pyridin-3-yl)phenyl)pyrrolidin-3-yl)amino)quinazoline-8-carboxamide;
4-(2-fluoro-[1,1'-biphenyl]-4-yl)pyrrolidin-3-yl)amino)
quinazoline-8-carboxamide;
4-(3-fluoro-4-(pyridin-3-yl)phenyl)pyrrolidin-3-yl)
amino)quinazoline-8-carboxamide;
2-ethyl-4-((4-(trifluoromethyl)phenyl)piperidin-3-yl)
amino)quinazoline-8-carboxamide;
4-(3,5-difluorophenyl)piperidin-3-yl)amino)quinazoline-8-carboxamide;
1-methyl-4-phenylpiperidin-3-yl)amino)quinazoline-8-carboxamide;
2-ethyl-4-(3-(trifluoromethyl)phenyl)piperidin-3-yl)
amino)quinazoline-8-carboxamide;
4-(3-methoxyphenyl)piperidin-3-yl)amino)-2-methylquinazoline-8-carboxamide;
4-(4-(trifluoromethyl)phenyl)piperidin-3-yl)amino)quinazoline-8-carboxamide;
4-(((3S,4S)-4-(4-(trifluoromethyl)phenyl)piperidin-3-yl)
amino)quinazoline-8-carboxamide;
4-(((3R,4R)-4-(4-(trifluoromethyl)phenyl)piperidin-3-yl)
amino)quinazoline-8-carboxamide;
4-(((3R,4R)-4-(3-(trifluoromethyl)phenyl)piperidin-3-yl)
amino)quinazoline-8-carboxamide;
4-(((3S,4S)-4-(3-(trifluoromethyl)phenyl)piperidin-3-yl)
amino)quinazoline-8-carboxamide;
4-(4-fluorophenyl)piperidin-3-yl)amino)-2-methylquinazoline-8-carboxamide;
2-ethyl-4-(4-fluorophenyl)piperidin-3-yl)amino)quinazoline-8-carboxamide;
4-(4-fluorophenyl)piperidin-3-yl)amino)-2-methylquinazoline-8-carboxamide;
4-(3-methoxyphenyl)piperidin-3-yl)amino)quinazoline-8-carboxamide;
4-(2-fluorophenyl)piperidin-3-yl)amino)-2-methylquinazoline-8-carboxamide;
4-(3-fluoro-4-methylphenyl)piperidin-3-yl)amino)quinazoline-8-carboxamide;
2-methyl-4-(((3R,4R)-4-(3-(trifluoromethyl)phenyl)piperidin-3-yl)amino)quinazoline-8-carboxamide;
4-(3,4-dimethoxyphenyl)piperidin-3-yl)amino)quinazoline-8-carboxamide;
4-(3-fluoro-5-(trifluoromethyl)phenyl)piperidin-3-yl)
amino)quinazoline-8-carboxamide;
2-methyl-4-(4-(trifluoromethyl)phenyl)piperidin-3-yl)
amino)quinazoline-8-carboxamide;
2-ethyl-4-(2-fluorophenyl)piperidin-3-yl)amino)quinazoline-8-carboxamide;
4-(4-chlorophenyl)piperidin-3-yl)amino)quinazoline-8-carboxamide;
2-ethyl-4-(m-tolyl)piperidin-3-yl)amino)quinazoline-8-carboxamide;
4-((4-(3,5-dimethylphenyl)piperidin-3-yl)amino)quinazoline-8-carboxamide;
6-fluoro-4-(((3R,4R)-4-phenylpiperidin-3-yl)amino)quinazoline-8-carboxamide;
4-(((3R,4S)-4-(2-fluoro-[1,1'-biphenyl]-4-yl)pyrrolidin-3-yl)amino)quinazoline-8-carboxamide;
4-(((3S,4R)-4-(2-fluoro-[1,1'-biphenyl]-4-yl)pyrrolidin-3-yl)amino)quinazoline-8-carboxamide and pharmaceutically acceptable salts, solvates, or solvates of salts, thereof.

5. A pharmaceutical composition comprising a compound according to claim 1, or a pharmaceutically acceptable salt, solvate, or solvate of a salt, thereof, as active ingredient, together with a pharmaceutically acceptable carrier.

\* \* \* \* \*